US008153376B2

(12) United States Patent
Pinto et al.

(10) Patent No.: US 8,153,376 B2
(45) Date of Patent: Apr. 10, 2012

(54) MEANS AND METHODS FOR DIAGNOSING AND/OR TREATING A SUBJECT AT RISK OF DEVELOPING HEART FAILURE

(75) Inventors: Yigal M. Pinto, Amstelveen (NL); Esther E. Creemers, Maastricht (NL); Joost L. Leenders, Maastricht (NL)

(73) Assignee: Universiteit Maastricht, Maastricht (NL)

( * ) Notice: Subject to any disclaimer, the term of this patent is extended or adjusted under 35 U.S.C. 154(b) by 51 days.

(21) Appl. No.: 12/440,226

(22) PCT Filed: Sep. 25, 2007

(86) PCT No.: PCT/EP2007/060173
§ 371 (c)(1), (2), (4) Date: Aug. 25, 2009

(87) PCT Pub. No.: WO2008/037720
PCT Pub. Date: Apr. 3, 2008

(65) Prior Publication Data
US 2009/0325170 A1    Dec. 31, 2009

(30) Foreign Application Priority Data

Sep. 25, 2006 (EP) .................................... 06121196
Sep. 29, 2006 (EP) .................................... 06121525

(51) Int. Cl.
*C12Q 1/68* (2006.01)

(52) U.S. Cl. ..................................................... 435/6.12

(58) Field of Classification Search .................... None
See application file for complete search history.

(56) References Cited

FOREIGN PATENT DOCUMENTS

| EP | 1522857 | 4/2005 |
|----|---------|--------|
| WO | 03084469 | 10/2003 |
| WO | 2004087056 | 10/2004 |
| WO | 2004112710 | 12/2004 |
| WO | 2006034356 | 3/2006 |

OTHER PUBLICATIONS

Fisch S. et al., "KLF15 is a novel regulator of cardiomyocyte gene expression" Circulation, vol. 110, No. 17, Suppl. S, pp. 262-263 (2004); 77th Scientific Meetings of the American-Heart Association; New Orleans, LA.
Fisch S. et al., "Kruppel-like factor 15 is a regulator of cardiomyocyte hypertrophy"; Proceedings of the National Academy of Sciences of the United States of America 24; vol. 104, No. 17 (2007) pp. 7074-7079.
Gray S. et al., "The Kruppel-like factor KLK15 regulates the insulin-sensitive glucose transporter GLUT4"; The Journal of Biological Chemistry (2002) vol. 277, No. 37, pp. 34322-34328.
LaFramboise W. et al., "Molecular dynamics of the compensatory response to myocardial infarct"l Journal of Molecular and Cellular Cardiology (2005) vol. 38, No. 1, pp. 103-117.
Okada et al., "Postinfarction gene therapy against transforming growth factor-beta signal modulates infarct tissue dynamics and attenuates left ventricular remodeling and heart failure" Circulation vol. 111, No. 19 (2005) pp. 2430-2437.
Schroen, B. et al., "Lysosomal integral membrane protein 2 is a novel component of the cardiac intercalated disc and vital for load-induced cardiac myocyte hypertrophy" Journal of Experimental Medicine (2007) vol. 204, No. 5, pp. 1227-1235.
Uchida S. et al., "Transcriptional regulation of the CLC-K1 promoter by myc-associated zinc finger protein and kidney-enriched Kruppel-like factor, a novel zinc finger repressor"; Molecular and Cellular Biology (2000) vol. 20, No. 19, pp. 7319-7331.

*Primary Examiner* — Teresa E Strzelecka
*Assistant Examiner* — Suchira Pande
(74) *Attorney, Agent, or Firm* — Bozicevic, Field & Francis LLP; Bret E. Field

(57) ABSTRACT

The present invention relates to a method for identifying a subject at risk of developing heart failure, comprising: (a) determining the level of one or more biological markers in a biological sample of said subject; (b) comparing the level of said biological marker to a standard level of the same biological marker; and (C) determining whether the level of the marker is indicative of a risk for developing heart failure, wherein the biological marker is Krüppel Like Factor 15 (KLF-15) and/or lysosomal integral membrane protein-2 (LIMP-2) and/or fragments and/or variants thereof, and/or wherein the biological marker is a gene coding for KLF15 and/or LIMP-2, and/or fragments and/or variants thereof. The invention further relates to use of the KLF15 and/or LIMP-2 protein, and/or the gene coding for KLF15 and/or LIMP2, and/or fragments, and/or variants of said genes and/or proteins, for the preparation of a medicament for a prophylactic and/or a therapeutic medicament for prevention and/or treatment of heart failure.

5 Claims, 16 Drawing Sheets

Figure 1A:
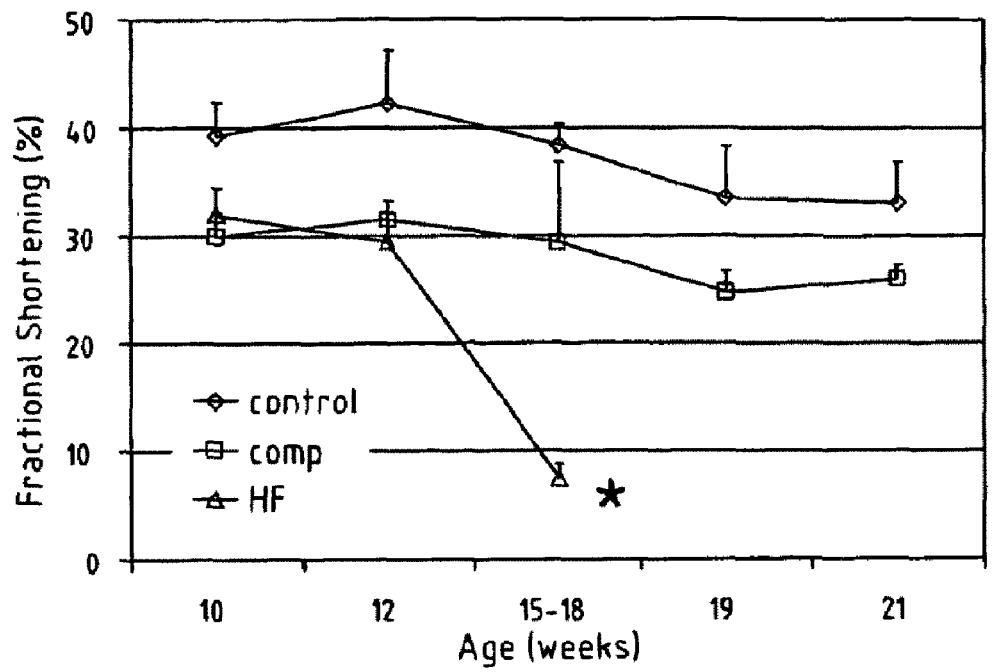

SEQUENCE LISTING

```
<160> NUMBER OF SEQ ID NOS: 30

<210> SEQ ID NO 1
<211> LENGTH: 19
<212> TYPE: DNA
<213> ORGANISM: Artificial
<220> FEATURE:
<223> OTHER INFORMATION: shKLF-15 sense oligonucleotide

<400> SEQUENCE: 1
gatgtacacc aagagcagc                                                  19

<210> SEQ ID NO 2
<211> LENGTH: 18
<212> TYPE: DNA
<213> ORGANISM: Artificial
<220> FEATURE:
<223> OTHER INFORMATION: shKLF-15 antisense oligonucleotide

<400> SEQUENCE: 2
gctgctcttg gtgtacat                                                   18

<210> SEQ ID NO 3
<211> LENGTH: 22
<212> TYPE: DNA
<213> ORGANISM: Artificial
<220> FEATURE:
<223> OTHER INFORMATION: FLF15 or BNP primer forward

<400> SEQUENCE: 3
gctgctttgg gcagaagata ga                                              22

<210> SEQ ID NO 4
<211> LENGTH: 22
<212> TYPE: DNA
<213> ORGANISM: Artificial
<220> FEATURE:
<223> OTHER INFORMATION: FLF15 or BNP primer backward

<400> SEQUENCE: 4
```
gccaggaggt cttcctaaaa ca                                          22

<210> SEQ ID NO 5
<211> LENGTH: 21
<212> TYPE: DNA
<213> ORGANISM: Artificial
<220> FEATURE:
<223> OTHER INFORMATION: PCR primer to assess the genotype of TbetaRI
      flox

<400> SEQUENCE: 5
atgagttatt agaagttgtt t                                           21

<210> SEQ ID NO 6
<211> LENGTH: 21
<212> TYPE: DNA
<213> ORGANISM: Artificial
<220> FEATURE:
<223> OTHER INFORMATION: PCR primer to assess the genotype of TbetaRI
      flox

<400> SEQUENCE: 6
accctctcac tcttcctgag t                                           21

<210> SEQ ID NO 7
<211> LENGTH: 21
<212> TYPE: DNA
<213> ORGANISM: Artificial
<220> FEATURE:
<223> OTHER INFORMATION: PCR primer to assess the genotype of TbetaRI
      flox

<400> SEQUENCE: 7
ggaactggga aaggagataa c                                           21

<210> SEQ ID NO 8
<211> LENGTH: 21
<212> TYPE: DNA
<213> ORGANISM: Artificial
<220> FEATURE:
<223> OTHER INFORMATION: Mouse BNP forward primer

<400> SEQUENCE: 8
gtttgggctg taacgcactg a                                           21

<210> SEQ ID NO 9
<211> LENGTH: 22
<212> TYPE: DNA
<213> ORGANISM: Artificial
<220> FEATURE:
<223> OTHER INFORMATION: Mouse BNP backward primer

<400> SEQUENCE: 9
gaaagagacc caggcagagt ca                                          22

<210> SEQ ID NO 10
<211> LENGTH: 24
<212> TYPE: DNA
<213> ORGANISM: Artificial
<220> FEATURE:
<223> OTHER INFORMATION: Mouse ANF forward primer

<400> SEQUENCE: 10
attgacagga ttggagccca gagt                                        24

<210> SEQ ID NO 11
<211> LENGTH: 24

```
<212> TYPE: DNA
<213> ORGANISM: Artificial
<220> FEATURE:
<223> OTHER INFORMATION: Mouse ANF backward primer

<400> SEQUENCE: 11
tgacacacca caagggctta ggat                                              24

<210> SEQ ID NO 12
<211> LENGTH: 20
<212> TYPE: DNA
<213> ORGANISM: Artificial
<220> FEATURE:
<223> OTHER INFORMATION: Mouse aska forward primer

<400> SEQUENCE: 12
tgagaccacc tacaacagca                                                   20

<210> SEQ ID NO 13
<211> LENGTH: 20
<212> TYPE: DNA
<213> ORGANISM: Artificial
<220> FEATURE:
<223> OTHER INFORMATION: Mouse aska backward primer

<400> SEQUENCE: 13
ccagagctgt gatctccttc                                                   20

<210> SEQ ID NO 14
<211> LENGTH: 21
<212> TYPE: DNA
<213> ORGANISM: Artificial
<220> FEATURE:
<223> OTHER INFORMATION: Mouse PPIA forward primer

<400> SEQUENCE: 14
caaatgctgg accaaacaca a                                                 21

<210> SEQ ID NO 15
<211> LENGTH: 20
<212> TYPE: DNA
<213> ORGANISM: Artificial
<220> FEATURE:
<223> OTHER INFORMATION: Mouse PPIA backward primer

<400> SEQUENCE: 15
gccatccagc cattcagtct                                                   20

<210> SEQ ID NO 16
<211> LENGTH: 21
<212> TYPE: DNA
<213> ORGANISM: Artificial
<220> FEATURE:
<223> OTHER INFORMATION: Human LIMP-2 forward primer

<400> SEQUENCE: 16
gtttgggctg taacgcactg a                                                 21

<210> SEQ ID NO 17
<211> LENGTH: 22
<212> TYPE: DNA
<213> ORGANISM: Artificial
<220> FEATURE:
<223> OTHER INFORMATION: Human LIMP-2 backward primer

<400> SEQUENCE: 17
gaaagagacc caggcagagt ca                                                22
```

<210> SEQ ID NO 18
<211> LENGTH: 21
<212> TYPE: DNA
<213> ORGANISM: Artificial
<220> FEATURE:
<223> OTHER INFORMATION: Human GAPDH forward primer

<400> SEQUENCE: 18
acccactcct ccacctttga c         21

<210> SEQ ID NO 19
<211> LENGTH: 22
<212> TYPE: DNA
<213> ORGANISM: Artificial
<220> FEATURE:
<223> OTHER INFORMATION: Human LIMP-2 backward primer

<400> SEQUENCE: 19
accctgttgc tgtagccaaa tt        22

<210> SEQ ID NO 20
<211> LENGTH: 21
<212> TYPE: DNA
<213> ORGANISM: Artificial
<220> FEATURE:
<223> OTHER INFORMATION: Rat LIMP-2 forward primer

<400> SEQUENCE: 20
tgcgtccaaa caaggaagaa c         21

<210> SEQ ID NO 21
<211> LENGTH: 25
<212> TYPE: DNA
<213> ORGANISM: Artificial
<220> FEATURE:
<223> OTHER INFORMATION: Rat LIMP-2 backward primer

<400> SEQUENCE: 21
aatctcttgg cccctcttaa aataa     25

<210> SEQ ID NO 22
<211> LENGTH: 18
<212> TYPE: DNA
<213> ORGANISM: Artificial
<220> FEATURE:
<223> OTHER INFORMATION: Rat PGK-1 forward primer

<400> SEQUENCE: 22
cggagacacc gccacttg             18

<210> SEQ ID NO 23
<211> LENGTH: 25
<212> TYPE: DNA
<213> ORGANISM: Artificial
<220> FEATURE:
<223> OTHER INFORMATION: Rat PGK-1 backward primer

<400> SEQUENCE: 23
aaggcaggaa aatactaaac attgc     25

<210> SEQ ID NO 24
<211> LENGTH: 53
<212> TYPE: DNA
<213> ORGANISM: Artificial
<220> FEATURE:
<223> OTHER INFORMATION: Rat shLIMP-2 sense

<400> SEQUENCE: 24
ggaagaacat gagtcatttg tcaagagaaa atgactcatg ttcttccttt ttc    53

<210> SEQ ID NO 25
<211> LENGTH: 57
<212> TYPE: DNA
<213> ORGANISM: Artificial
<220> FEATURE:
<223> OTHER INFORMATION: Rat shLIMP-2 antisense

<400> SEQUENCE: 25
tcgagaaaaa ggaagaacat gagtcatttt ctcttgacaa atgactcatg ttcttcc    57

<210> SEQ ID NO 26
<211> LENGTH: 2543
<212> TYPE: DNA
<213> ORGANISM: Homo sapiens

<400> SEQUENCE: 26
ccacgcgtcc ggcgacccgc gggccggcgg gcgatcgagc cagcgcagga cccgcggctc    60
ggcccccggc cgccgccgga ccgagagtct agccgccgcc cccagcccag cccgcccggc    120
cgcaggaccg ccggggcctg gccgccggtc cggcgtgcgc caagttcagc cgccaccggc    180
acggccaggc cagcatggtg gaccacttac ttccagtgga cgagaacttc tcgtcgccaa    240
aatgcccagt tgggtatctg ggtgataggc tggttggccg gcgggcatat cacatgctgc    300
cctcacccgt ctctgaagat gacagcgatg cctccagccc ctgctcctgt tccagtcccg    360
actctcaagc cctctgctcc tgctatggtg gaggcctggg caccgagagc caggacagca    420
tcttggactt cctattgtcc caggccacgc tgggcagtgg cggggcagc ggcagtagca    480
ttggggccag cagtggcccc gtggcctggg ggccctggcg aagggcagcg gcccctgtga    540
aggggggagca tttctgcttg cccgagtttc ctttgggtga tcctgatgac gtcccacggc    600
ccttccagcc taccctggag gagattgaag agtttctgga ggagaacatg gagcctggag    660
tcaaggaggt ccctgagggc aacagcaagg acttggatgc ctgcagccag ctctcagctg    720
ggccacacaa gagccacctc catcctgggt ccagcgggag agagcgctgt tcccctccac    780
caggtggtgc cagtgcagga ggtgcccagg gccaggtggg ggcccccacg cctgatggcc    840
ccatcccagt gttgctgcag atccagcccg tgcctgtgaa gcaggaatcg ggcacagggc    900
ctgcctcccc tggcaagcc ccagagaatg tcaaggttgc ccagctcctg gtcaacatcc    960
aggggcagac cttcgcactc gtgccccagg tggtaccctc ctccaacttg aacctgccct    1020
ccaagtttgt gcgcattgcc cctgtgccca ttgccgccaa gctgttggat tcgggacccc    1080
tggggcctgg ccctgccggt ctcctcatgg gccagaagtt ccccaagaac ccagccgcag    1140
aactcatcaa aatgcacaaa tgtacttttcc ctgctgcag caagatgtac accaaaagca    1200
gccacctcaa ggcccacctg cgccggcaca cgggtgagaa gcccttcgcc tgcacctggc    1260
caggctgcgg ctggaggttc tcgcgctctg acgagctgtc gcggcacagg cgctcgcact    1320
caggtgtgaa gccgtaccag tgtcctgtgt gcgagaagaa gttcgcgcgg agcgaccacc    1380
tctccaagca catcaaggtg cacgcttcc cgcggagcag ccgctccgtg cgctccgtga    1440
actgaaagcg ccctgaaccc cagcctgtcc gtcaccccgg atccccaccc catcccatt    1500
tttttaagca ataatttatt tgcctcctcc agagggacat ggcaatgtta ccagcccacc    1560
ttctgaagcc tggaggtgt gaaccagggg cccgccaacc gctgcctttc tcgggagtac    1620
ttagagcctc gaacccgcgt ccctgggggc tgggcccag gcgcacgggg ctggaggcag    1680

-continued

```
gccttcgtgc cttcgtgcct tcgtgccttc ccgcggtggc caggcctctg ctgcagccgc    1740
tggttgcagg cagagttttg gggacctggc ccttctccca ctgggctccc ccatcctggg    1800
ccaaggccag aactttagtg ctaggggaag atgaaatgtg cagttttgaa atgttgggtt    1860
tccagagaga gtcatgctgg aggagaagga agtaggccag aagtccaggg ctgcactgtg    1920
gtgtgagggt ggctttgtct aagatgcctg ctcagcatga tcaccagagg gtgtgggcag    1980
gtccctggag cggggggggg ggggggggg ggcggaccgg gccgctgggc cctcatgtgg     2040
gagagaggtg aaaagcgtcc cccactaggg ggctggcagt gcatgtgctt gagttaaatg    2100
tgcagggcag acagagccag aagggcctgt acccaggggc tcgtcccctc ctccggtttc    2160
ccagacaaat ccagacacca gcctttaggg tggccttggg aggagagggc caggctgtcc    2220
tgggtgtgag agaactagat agagcctccc aaccctgatt tagaaatgca ttccttattt    2280
tgtctagaaa ttaataaatg aactagcttg ttttgacagg tttatttcac atcctatgaa    2340
tgtatgtaaa taaactgtac ataggtccat ccacataaaa tatcttttaa taacatatca    2400
acatttgtgt aaatttgaaa tttaaaaaaa tctatgaagc tggtgtacat atgttacaat    2460
tacgtatatt ttctttggtc cttcataaaa atatatttac tttgccaata aaagaaaaa    2520 gaactcacaa aaaaaaaaaa aaa                                            2543
```

<210> SEQ ID NO 27
<211> LENGTH: 416
<212> TYPE: PRT
<213> ORGANISM: Homo sapiens

<400> SEQUENCE: 27

```
Met Val Asp His Leu Leu Pro Val Asp Glu Asn Phe Ser Ser Pro Lys
1               5                   10                  15

Cys Pro Val Gly Tyr Leu Gly Asp Arg Leu Val Gly Arg Arg Ala Tyr
                20                  25                  30

His Met Leu Pro Ser Pro Val Ser Glu Asp Asp Ser Asp Ala Ser Ser
            35                  40                  45

Pro Cys Ser Cys Ser Ser Pro Asp Ser Gln Ala Leu Cys Ser Cys Tyr
        50                  55                  60

Gly Gly Gly Leu Gly Thr Glu Ser Gln Asp Ser Ile Leu Asp Phe Leu
65                  70                  75                  80

Leu Ser Gln Ala Thr Leu Gly Ser Gly Gly Ser Gly Ser Ser Ile
                85                  90                  95

Gly Ala Ser Ser Gly Pro Val Ala Trp Gly Pro Trp Arg Arg Ala Ala
                100                 105                 110

Ala Pro Val Lys Gly Glu His Phe Cys Leu Pro Glu Phe Pro Leu Gly
            115                 120                 125

Asp Pro Asp Asp Val Pro Arg Pro Phe Gln Pro Thr Leu Glu Glu Ile
        130                 135                 140

Glu Glu Phe Leu Glu Glu Asn Met Glu Pro Gly Val Lys Glu Val Pro
145                 150                 155                 160

Glu Gly Asn Ser Lys Asp Leu Asp Ala Cys Ser Gln Leu Ser Ala Gly
                165                 170                 175

Pro His Lys Ser His Leu His Pro Gly Ser Gly Arg Glu Arg Cys
            180                 185                 190

Ser Pro Pro Gly Gly Ala Ser Ala Gly Gly Ala Gln Gly Pro Gly
        195                 200                 205

Gly Gly Pro Thr Pro Asp Gly Pro Ile Pro Val Leu Leu Gln Ile Gln
    210                 215                 220
```

```
Pro Val Pro Val Lys Gln Glu Ser Gly Thr Gly Pro Ala Ser Pro Gly
225                 230                 235                 240

Gln Ala Pro Glu Asn Val Lys Val Ala Gln Leu Leu Val Asn Ile Gln
            245                 250                 255

Gly Gln Thr Phe Ala Leu Val Pro Gln Val Val Pro Ser Ser Asn Leu
        260                 265                 270

Asn Leu Pro Ser Lys Phe Val Arg Ile Ala Pro Val Pro Ile Ala Ala
    275                 280                 285

Lys Pro Val Gly Ser Gly Pro Leu Gly Pro Gly Pro Ala Gly Leu Leu
290                 295                 300

Met Gly Gln Lys Phe Pro Lys Asn Pro Ala Ala Glu Leu Ile Lys Met
305                 310                 315                 320

His Lys Cys Thr Phe Pro Gly Cys Ser Lys Met Tyr Thr Lys Ser Ser
                325                 330                 335

His Leu Lys Ala His Leu Arg Arg His Thr Gly Glu Lys Pro Phe Ala
            340                 345                 350

Cys Thr Trp Pro Gly Cys Gly Trp Arg Phe Ser Arg Ser Asp Glu Leu
        355                 360                 365

Ser Arg His Arg Arg Ser His Ser Gly Val Lys Pro Tyr Gln Cys Pro
    370                 375                 380

Val Cys Glu Lys Lys Phe Ala Arg Ser Asp His Leu Ser Lys His Ile
385                 390                 395                 400

Lys Val His Arg Phe Pro Arg Ser Ser Arg Ser Val Arg Ser Val Asn
                405                 410                 415

<210> SEQ ID NO 28
<211> LENGTH: 55142
<212> TYPE: DNA
<213> ORGANISM: Homo sapiens

<400> SEQUENCE: 28
cctcgcgggg ttgcggcgag cccggcccgc gaacgtcacg tccctgcgcg ctccctgcac      60
tctcccgagc tgcgctaggc gggcgccacg gctgcccggc gaaggaaacc gaaaccgagt     120
ccgggcccgt ccctccgcgg ccccatccgc ccggtgcacc cggggccgcg ctcgccaggc     180
cgcggagccc agagctgcgc gcacgaaccg tgcgccggga gggcgtgggc gtggcgccga     240
agggtcccgg gtcttcgacg cctctgcggc ggctcctccc tccttgcagt tggatccctg     300
gcgggtgcgg cccggcccgg cccgtgagcg cgcacagaa tgggccgatg ctgcttctac      360
acggcgggga cgttgtccct gctcctgctg gtgaccagcg tcacgctgct ggtggcccgg     420
gtcttccaga aggctgtaga ccagagtatc gagaaggtga ggcggggcgg gctgtgtgtg     480
tgttgtggag tcgtccagct caccctccca tccctgctgc tacatcttgt atgggaaaga     540
ccagcactca ggcagaccct ccgcgctaga gctcttcttg cgtccctgtc ttccagggct     600
tggtaggcga gggttaaaga aggatgagga aggatggagc cgactctgtt cccttttacag    660 tgataagtaa ggctatggat cctgactttt aaaaaggcct tcggttgtgt tctgtcgttt     720
gcatctctcc ccactccttc cgtctacacc ccaatctcag gtgggcccaa acttgtttcc     780
ttcccacttc atgaagaaac agaactgaat gaaagacacc gcagaagagg caggttatgt     840
tgtctgcttg ctgtagcctt tgaagtggtg tgcgcctggg gatgagacgt gggtgtgcgg     900
tctattgtgt tcttgccctc ttgggctggg caggggcagt tggtagctgg gccagtcctt     960
taggctgggt gacaattcat ccatcagtct ttgctgaacg ctgacttagt ggctttgtat    1020
cttgtaccaa cagtctgtgt tgctttgtct caccatgaat tcttgttttt ctcaaacggc    1080
```

```
cataattttc aggcacagat gcatttagat accctacaag aatctgaact tgtctcttcc    1140
tctagatgat tgggctggag agccagtcct ttaagaagac ttcatctttt gatttcactg    1200
gtcatttcat ctgccctttc ccccacatcc accaagctgt gtcaaaagag aacaaaaga    1260 gaattactgg gatcattttt tccttaaaaa agaaaaataa tcactggagc agcagccttt    1320
cttgttagca tccataactg cacgcttcat ttctcccact ggtctgcact tgctgcggcc    1380
agataaaaaa gcccaggcct agtctacttt gaatcactgc actctccagt cagtaaagct    1440
attttattcc aggtggcaat ggatatcttc ctttaactga gtttccaaaa gtaattaagt    1500
gagtacctga aatctggcag ttaaaggcag ttttcaaaa agcaccatgg caaagcataa    1560
tgtaattttt aaagttcaca ttgccaaggg aagacaaggc ccactgtctg agcgtctcga    1620
gggtcagttt cctttgagca atcatgttca aggaaaaaag aaactgaatc ctttctccac    1680
tcctgtccat gtccaaatcc atggtgagct gtgtttgagg atgtaaactc ttgctttggg    1740
tgactagagt aaagcaatcc aattatagta aatatgtgag ttttcttata tggccttgaa    1800
aggctgtttc aaggagccct ataggatgag tgatcttccc cgtggttccc atatagccag    1860
cccttagatt ctctgtgtgt ctccatttct ctgggtgagg gggtggctgt aaggcaactt    1920
ggctggggcc tgagtttgtg ttgatatttc caagtgtttt tctccatgag gaatggactc    1980
tgttctgata agtaatagta cagggaagtg gactttcaga gctgctcaat cccagctaag    2040
gaggactgca cggtgtattg tatgaaacta aaggacaggg ctagtttcag tgggcaggtg    2100
tggaaatact gttgtcatta gaggtaagtc acacatcgct attctgcttt ttcctggatt    2160
acctgtaggg tggtaggtag catgggacag tgggaaagat tgaggatgtt acactcctgg    2220
gcatgaaacc tagcttccac tatgtcccag ctcggtgacc gtgggctgtt taatcttact    2280
tgattcatgt tttccccatc tgtaaatagg gataataagg actaacgatc acatctgctt    2340
tgtcaaataa ttcttataac cttaaggtgt gatctttctg ggatatagtt agtgcttaat    2400
aggtgatagc aactttattt ttattagaag ccacacaaag aaaatacgtg agatttggag    2460
tcagattcca tatgttcaaa tcctatcctt gccagtataa gctttatgac ttacgtcaaa    2520
taacttactt ggtcctcaat ttcattgctt gtaaaactgg ggatatgagc tgttagctaa    2580
cttgggcaca gtgatgcatt taccatgaaa ctcgcaaagt taagctttgg gtctctcact    2640
tgcacagacc cttgcgaagc cctgtacctc attctatatc ccaaattttc tttttttctta    2700 agaaggaccc ttcaaattgt ataagcttca ggacccacaa aacctggatt tgtctctgca    2760
tgtgtattat tgtaggacca agtataaagc acttagcata gtatcaggca cagaataggt    2820
aatcaatatg tggcagtcat ctttattgcc actagtatta ctatgggaga attcattcat    2880
aacttgattc taatgtagtt ataatataat ctactctgat atttccagtt ctttgttttt    2940
tcatttgaag attgtctatg ccccgacttg tctatgtcaa aaaggaagaa gggaaaaggg    3000
atgaaattca aatgagtagg tgtgggaagc ttagtaagag aattcctatc caaaaagttg    3060
tctcaaatga taattgtcct tgaaccctgc agtgaccaga ggtaactgaa gagagacttt    3120
taattttggc cagtgaatat cgtggaagga accaagacaa ttttgtttca tttttggcct    3180
cagtggtgac tgcctcgtat tgggcaaggc ctgtaattgt ttctgcttca attttctcat    3240
ttgcaagaga ggcataatag tacttctctt ttttcccacac cctcttccta ggggatattg    3300
tgagcattaa taaggcattt ccttacaagc gtttgggcct tcatgaagag agagctttgc    3360
agagacccag cagttccttt tcctcccctta ggcctgaaaa ggcaggagtt tacgttacat    3420
ttcatctggt atcccagtga actgccttga cacctagcac agtgcctgag atacatatta    3480
```

```
aatgcctctt cactcgcctg tgatcatttt aatagaaaga agagtgtcct gagaatcagc    3540
agaactgaat caaacatttt ttttctgtcc ctaaggattt cttggactaa gctgaacaag    3600
cacagtggca agttatttaa tccctcaaat cctaaggatc ctcattttga aaataggaac    3660
aataaggata agaatactta actcagagtt gtcacaagaa tgaaataata tgatatctat    3720
aaagcaccca gcacaatgcc tcgcacaatg cctgaacgtt aacagttgtt atgtctttag    3780
ctatatttgt catctgtgaa ttgaaactta ttatacaagc tatggttcct cttagctcca    3840
aacttctgag atcccatgac ctttaagagc agctatgcag ttcagaatat taagtttgcg    3900
ctcctaatct ctgcagacgt gctggcaggt tgactgtctc ccagtaatag ggatgcagaa    3960
ctggccacag tcagggctgg ccaacaaggg atgggatggc aagggaacca gtgggagact    4020
gtttacacct ttgacttcct cttcacaggt caaggcagga ctgtagcatt aggtctcaga    4080
gatgcaatga acaggacaaa tacacttccc cttcatctgg acctgaggct ctgggcaagt    4140
cagtaccagc tggtttcttt tgggagccat agaaactctg gagctgttct accgattcct    4200
caagaagtaa aatataggcc aggcgtggtg gctcacgcct gttatcctaa cactttggga    4260
ggctgaatcg ggtggatcac aaggtcggga gttcgagacc agcctggcca atatggtgaa    4320
accctgtctc tactaaaaat acagaaatta gctaggcatg gtggcaggtg cctgtagtcc    4380
cagctactcg ggaggctgag gcaggagaat cgcttgaatc cgggaggcgg aggttgcagt    4440
gagccaagat ggctcccttg aactccagcc tgggcgacag agcaagactc tgtctcaaaa    4500
aaaataaaaa taaaaataaa aaagaagta aaatgtaatc actgataacc agattgcttt    4560
gattggtgac tatgggatct tgttttttaa agtcaaatca gcaaaacatc tttattgatg    4620
tgtatgtaaa ggcattcagc tatatatcat ttaaaaggc tccttcttgc atatctacct    4680
catctcctga gttgcctcta ttcaaagaag acttatctta gtctgagatt tttcttgatc    4740
agaaaaaaac ctgtaaagat atcttaaatc tgttatctta cggtcaagga aattgaggct    4800
cttggaatag aagtgactta tctaaagtca aatggagagg gaaggagaga gcgtgccagc    4860
tagccttctg atcctgaacc cacttttccc atctcaagga tgaccataca tcccatttgc    4920
ctggaatagt cctacatggt ttctgtgtac ctgttgtgct ggtgtaatca ctaacacccc    4980 cttttcctcca aaagatttct gctttggaca ataaattcta tggccatccc tcacctctca    5040
tgctacattg tccttacaga ccacaatgta tcccgcttct tggctctctt aaggagttga    5100
ggcctactca aactagctct ggcaagagag gattctttt tttgtttctg taaatctgga    5160
aggggaagct catagaaatc aaagggcaag aaccacggca cagtaaggcc tcctgagagg    5220
acaaccgaaa gtggaaagtc agcaggaagc aggcacactc tgcctcccac ttttcctct    5280 gctttctcca ccaacaggct tcctctgttt actcagcctg gctctgtact catccgggct    5340
tgctcagccc cgcctcagtg tgactttcca gctgttgacc tctcatagac atgcttcatc    5400
tcctagtttc tcttttccaa gtttataacg gagcaatgtg attggctcag cacaggaaga    5460
aactatagca ctgtaaacgg aggcagtgtc gttaatttcc ttgcaagatt ctctaactcc    5520
taagcaaaat tatccaaatt ctttcctggc ttttagaaac acgatcttgt gatatcaaaa    5580
tcatattaag tttattttag tgtcttacta attcatgttg actatgagtg cattccttat    5640
taatgattaa gacaatatag taggctaaca gttgtcagca tagcccctag actctaggag    5700
atgcatctaa atcacttaca aagatttaga aaataccaga ccccatccca gacttgctga    5760
atcagactca ttaggaacag aactcaggtt aaagtgctta tcataaaatc cattactgga    5820
ggcaggttgc tgtgggatcg taatctgcaa ttttgggaat atgcattttt aaaaaaggtg    5880
```

```
tttatatttg tatagtgatt attttagacc atgtcttcat tccttaagat ggtaattctg      5940
actgaggaga ttactactta taattactat taatctgcaa gtttacatta aaggaaatat      6000
tatttggtga ggaggggaag attcctgcct gtggaaacta ctttgcttta ttgttaaata      6060
aatccaagat ttcattctgt caggccacag cagagggcc atctgttctg ccagacattt       6120
gcttatttcc caggaagaat caggaggtgg aattataagc tcattgatga aaacatagga      6180
tgttggccaa gttactagac attcctggcc atatcatcaa gatatgcact atctatacac      6240
tatacactaa ggaagggacc attttttaatc caagctggta actggaaaaa acaaccaagg     6300
aaaaataaag accactttag gtgtttgctt tctatatcta aatgcacttt tgggtacatg      6360
ctttggcagt cattctttca tttgacaaat atttactgag tgtgtaccat ttgcaaggca      6420
gtgtgctaag agctatggat ataacactaa acaagaggca gtctctaccc ttgcagattt      6480
tataatccaa tttaaactcc tgggcccctc atattcttaa aaattattga ggaccccaaa     6540
gaacttatgt ttccataccct attgatagtt acaatattag aaattgaaac tgatatgtat     6600
ttttgagaaa tgtttaaaac agaagactac acaagcacat attccaatat gacatcatta    6660
tatatcacgt aacctctgga agactccact ctacactcag agaaataata gaattaaaaa    6720
cgcaaatgat accttagtat taaaatagtt ttgaccttgt gggcgcctcc taagaaggtc   6780
ttcgggctcc ccaggggtcc tgagatcaca ctttgagaac tgttgatcta gttttcattt    6840 aattatttt ttagaatatt tttaaaaata cataatatcc ctgtttttata ttcctgtaag   6900 gccagtttgg aagctatctt gttaatgttt tcaaacaacc aggattttgc ttggtgtgtc   6960
tttgatttac tgtgtccttt tggctttcct gtgagtccag tgttaaaaat aggagtttgg    7020
gccatcagta attccagttc cacaatctct tgtctttccc cgagtgctga tcaaagtaga   7080
caagagcatt catatctcca taattgaatt actcagtaat tcccttctgg cctcagccct    7140
gcggggattt tcaacccata tgacgtaatt tggtatttta atctagtatg aaagctctct    7200
ttgaaggtag atgtcctgtc gtatttagtt ttgtgtcttt tcttactgcc aaatgcaatg    7260
tcttattcaa aatagatggt cagtaagtgt tacttggatg aatagagaaa ataatttctt    7320
tggaaatgat tttgtttgca ttttgttgtt tagtctcaca ttttgcctca ctctgtaggc    7380
cagtggtcac atgtttgtct catgaatgat ttataccttt aaaatctgga aacttcacgt    7440
attggtccag atttccagct tctcttgaaa catgtggatg ttctttggta ctcgtcatac    7500
caagttctgt gtggtagctg tctcggcaga aaagaggctg accccttagaa gagacctgcc   7560 ttccctgttt cccactgtct tagtccattc aggctgctgt cacaaaatag catagactgg    7620
gtggcttata aacaacagaa atttatttct tacagttctg gaggctagga agtccaagat    7680
caaggccccg gcagatttgg ggtatggtga gggtccactg cctcatagat tatggtcttc    7740
tcactctaac ctcacatggc aaatgagctc tctggggtac cttttatgag aactaatccc    7800
attcgagagg gttctacgct cgtgacctaa tcacctccaa aggccccacc tcctaatctc    7860
accaccttgg gggtaaggat atcaacaaag gagttttgag gggacataaa cattcagacc    7920
acagcaccca ccgtcctttg cgcccttatt ggctcccaag gcccagtgaa ggtatccgtt    7980
gttgtgcatg tgctgttgtg tttcttagag tagagaaatg tttctctata tctgacactc    8040
cttaccaaaa gaaggaaaat gaaagatagc ttgagggat catgtgttta acagaaatgg     8100
gggagggcat gtttctctgt agaaatgaat attgctgctg gggtttgaca tgcaaacaaa   8160
tgtacaaacc catggcctgt gtcactcatt tgccctagcc atctggcccc ttcagcatct    8220
gaattttaca cactttccag agacagtgtg aggcagagtg ccattgttac actaatgtaa    8280
```

```
tcactcatca caagtcccat tttttaaaat tcattttta attgacaagt caaaattgta    8340
catatttagg gcatgcaaca tgatgttttg agagagatat acatatagat atacatagtg    8400
aaatggctaa atcaagctgt ttaacataca ccttacctca attacttatc tttgttttgt    8460
ggtaagaaca caaaatctaa tctcagcatt tttcaaatat acaatatttt ggggttttat    8520
tttatttat ttttgttttt gttttgtttt ttgttttgag atagggcttc tctctgtcac    8580
ccaggctgga gtacagtgcc actaccatgg ctcactgcag ccttgacctc ctgggttcaa    8640
gccatcctcc tgccttaaac tctaaagttg ctggaactac aggtgtgcac catgccaggc    8700
taatttttaa atattttttt gtagagatgg ggtcttgctg tgttgcccag gctggtctca    8760
aattcctgag cttaagcaat cctcccacct ttgcctccta aagtgctggg attacaggcg    8820
tgagccactg tgcctggccc aatatattgt tatccactgt gatcaccatg atgtacatta    8880
gatctcttga atttgtttat atcaaactga aattttgtgt cctttgacta acatctcacc    8940
agtcctccca gcgcccacaa ttcccatttt aaggatattt tctttttaaca ctgtacttct    9000
gataatcaac agtagtggaa gaggagacat agaaataggt aggtaatgaa aatattactt    9060
atttcaattt tgagagatat aatcacaacc aaacaggttg caaaataatg agactggctg    9120
tgcaagttac acacagaatg tgggccttgt ttccgtggcc ttatttctta tttattcaca    9180
tctgaaactc ctctttctca cccgcctccc cactccccat atatgtatat atatattccc    9240
ctcccgctcc caattttcac ctggttctat gtttaagttt ctatcggtag ctgctttttt    9300
tcccttagg tcatcagttc tcaaacttgg ctgtacattt gtaatcacct agaaactttc    9360
aaaaataagt tagtgggtat tttgtagcag gaggtttttt gggattgtca ttccaccata    9420
ttgtcctgta tgtaatttat aaacaaagta cagttcaccc atgagctaca tttgaatctg    9480
aactatcaga gctcattagt taaaattatg acagttgcaa aatgaaaatg agttaagcaa    9540
cagtgacata aataaatgaa tgccaataca ttttactga gttaaaataa ggtcagggaa    9600
taagagtaga atgttaatgg cagtttcttt ctttatgta aacagtggaa attacttaaa    9660
ttactgcatg agtctgggtt gggtttgctt cgtttcaggg agcaattta aaaaacaaag    9720
caaatcaatt ggtgttttgc catttgatga gttttattaa tctggagtcc agtatacaat    9780
taggccaata taccatccat acacaattag ggcaagttct ccaagttggt ctgcattatc    9840
tctggatgaa tttagactgt gcagatggca acatggatgc ttaagttgtg tttaattatg    9900
aagtagcact ttactgacct taaagaacaa ccagtagtgc tctcgaatcc cgaaactttc    9960
cttaaaggta ttactgattc ccgtgaaagc ctaatggatt ccctgagtgc ttattttat   10020
cacttggaag tggcttacat caggacagct ggtttcacca ctctcatggt gttgccttcc   10080
caaaagattg ctgttaggct gacttgggtt gtggctgtat taagtcatgt cagtgttcag   10140
cagtcaagct aatccagcct gcatctgttc cttcatctgc aggtcaggtg tcagcctggc   10200
cagcgactcc atgttcacta cacacagctc agagaggttg ttctcagttc tgtctctgac   10260
cagccttctg tgtacccaaa tggaagctta tgctggttga agattctttt acttttgttt   10320
taaaacagtc tcacttcata catggtaaaa actgttatgc ttctccagta attcaagaaa   10380
tgcaagttca aacaagaaga tgctattttg ccactactga ggaagcaaag attctgaaa   10440
accttaaaca ccaatattgg gatggatatg ctgaaatggt tgctcataca ctgctttctg   10500
gagcaacttg ttgatatttta aaggctgatg agttcatgaa aacttttgt ctctagaccc   10560
aataatccca atctaggagt ctattctaag aaattattca ctgatttggg ccaggtgtgg   10620
tgcctcatgc ctgtagtccc agcactttgg gaggccgagg taggtggatc acttgaggcc   10680
```

```
aggagttaga gaccagcctg gcccacatgg ttaaacccca tctctactaa aaatacaaaa   10740
agtagctggg tgtagtggtg tgcacctgta atcccagcta ctccagtggc tgaggcatga   10800
cagtcaaaag ttgcagtgag ccaagattgc accactgcat tccagcctga gtgacaaaag   10860
caagactctg tctcaaaaaa agaaaacaaa attattcact aatttggaca aatatattca   10920
agaacattta cttcagcatg aaagcaacac aaatgtccta tagtaaaaga atgattaaat   10980
aaactgattt agtatatttt tttaaatata ctaatacagt ggattagtat acagacatta   11040
aaataacagt ttcaaaacct atttaataac aaggataatc gtttataaaa gatgagtcaa   11100
aaaatgatac aatacatatg atctcaattt tgtttaaaat acacatatat atgactagac   11160
cagagggaaa taaacccata tgttaacagc gatagtgtgg attacagggg atttaaattt   11220
tgttcctttt actttcttca ttgtccaaat tttctgtgac aaatataatg gaatgggtag   11280
ggaatggatg gagtagcatt tacctgattt aaagtaacaa caggctgggc acggtggctc   11340
acacctgtaa tctcaacact tgggaggct gaggtgggca gatcacctga gatcaggagt    11400
tcaagatcag cctgactaac atggtgaagc cctttctcta ctaaaaatac aaaattagcc   11460
aggtgtggtc atgtgtgcct gtaatcccag ctactcgaga ggctgaggca ggagaatcgc   11520
ttgaacccgg gaggcggagg ttgtggtgag ccgagtcatg ccactgcact ccagcctggg   11580
caacagaatg agactccctc tcaaaaaata aataagtaac tgaataaata aaaataaag    11640 taacaacaat cagtagcatc atttgtgaat agaaattgga ggcaacacat gactttttct   11700
gcacatttgt agtaatgtta tctgctactt taaacatctc ttctaatatg aatatagaaa   11760
tttctgtaga ttgataattt atcataatat ctaggtattt ttcccttaga taaatgtgat   11820
gttttattgc ttacaagtct agtttgttcc ttgttatatc aaggagtttt tagaattcac   11880
caataaaatg agaaggtagg agatcttgtc taccattata tctccaatac ctagaacagt   11940
ggcttagcac aaaggaattg ctaagttaat atttgtggaa agaatgaaag agtttcatca   12000
gttttaaggt tgtgaaaatc ctatgctata cttgctatga aaaaggatgt tataaaaaat   12060
tcattaaaac caaaattgct aaagacagat ctaacagact tagaactaat gtttgtgtgc   12120
ctttggcata ttaattatgc ataaaaatag accctgctaa ttccaaacta gtcttaacca   12180
tttatgaaag gaggccaaaa tgtctccttg aaaaataata tttgcagcta agaaagttac   12240
tgtctcttct tgattctgca gtactgaaat tcagactttt tatttattca gatcaccttt   12300
cttacatatt atttagaata tgcggcattt tgccacattg aagattttac caagaagaac   12360
tgggtaaaca gcagaagatg aatgcctggc acagcgttgt gctctacgct gcggtatcat   12420
ctgtttcttc attaattatt tattgtgtcc cttctgtgcc agaaaccatg ttatgtgctg   12480
gggatccatg aaaaagatac agttcttagt atcagaccca atctgacact aaagactaat   12540
gaacacattt tccttataaa acttgtgaag tttcatgaaa gcagagagaa acacatagt    12600 tcagagggc cttctgagag atggcacttc tgaattgagc cctgaagccc aagtagaagt    12660
gaaccaggtg ataagggccc tgcagagact tctgggtgaa gggcggtgag tgactcaggc   12720
caaggcactg gctgagaact tgtgtggtgg gtgctaggta acagtagatg gttgcgtgtt   12780
actggtgcat aaagtgccta ccaggaaaag acagcgacag gtgacgcagt tgcatcagat   12840
cacaacaggt caaggactgt ggactttatc ctttgagcag gggtggagta tctgttccct   12900
taggcacttt tgacaggctt ctctgaagcc tgagatggat gaagcatttg aaaggaaaaa   12960
ggctggagag agggagacca gttaggagcc tacatacagt attgtcacag tccaagccaa   13020
tgatgaaatg tgccttgggg tagaaatggg gaagaggagg aggtgaaatc agcaggactt   13080
```

```
agtgatcaac tagggagaa aatcatgagt ccattttggt catgttgtct tggagcagcc   13140
tgtgagatgt ttagatgggg gaattttatc acagatccat gctactggaa ggatctaaat   13200
aatttcaggc ataagctgtt tgttaggctg aattactgag tcttgcacat aattttccac   13260
tccctgttac atgcatgttg gttttgtgtc cttagctaaa tttcttctta cagacagggc   13320
ctatgcctgt ttgcagggca tagtccgggc acatagaaag ctctcagtag gtacatattg   13380
ggtgattaac tgaaaagtat gttttttagt ccaattatta atttagctgt tgacactgtg   13440
aattcaccat agaacttgat aattttccag tattttgttt tagtggtagt gccacagtat   13500
tgtgcgtgga aaaattcatt atgttcgtct tggttaaaac taataagcaa cagttatatt   13560
gtgactccac agtgccactc ttaatatcca gagtcacact gtaaaactga tttaaggcct   13620
tatgttgctt tttcatttag tgtaactaag aagactcagc tgattacaag gtttgtctgg   13680
tggctgtcat caccacagca gaaccctcgg tgaggaagat cagttgttcc caagccatgg   13740
ctttctgttc agactggcaa agggcgcctt tgaggggac actagctcgt tgtatctggc    13800
ggaatgaata acttcctgtg ccagacagtc cgcggtcttg aggctgaggt tattatttgt   13860
tagtttctca ggccttcctt tgccgagcaa gctcctggga gtgcacactt gaatgccctg   13920
aggatcagaa atagaagggg cagaaattaa agtttaagt caaaacagag ccctctctgg    13980
gccatcttgt ggcaggaggt tgaggtgctt tctttggacc cattagcata ctggggctgc   14040
gcggctgcct ggaaactcta gagttgaact ctcccttttt cggttcctca cctgtgggct   14100
ccttactagg agctgacagt gacctcacgc agctgcccta gtttcctttc ctccagatgg   14160
cacgggtaac actcgaggaa accctgagag ttcagagtcc aacttatggc ttctccatag   14220
tttcactgtc cctctgggct agagttgcca aataaaataa aatacaggac aaccagttaa   14280
atttgaattt cagataacaa ataacatttt agtatgagtc tgtctcgtgt gatatttcgg   14340
ttcagtccga tgtatcagtt gttaatgtcc tgccatattt atctctctga tgcacttttt   14400
cttgaattat ttgaagtaag ttgtagatat cacacacttt gttcctaaat ccttcagcat   14460
gcatctccta tgaataaaaa cattttgat gtagcccatg caatatttgg gacataatta     14520
tattataaaa ttatttgttg tttatctgaa atacaaattt aactgggtat cccaggtttt   14580
atttgctaaa tctggcaact ctaccctcag ggtgccatgg ggtggcagct gctggatggg   14640
tgagtaaatc tgcactcctg gacttggtca gatttgattt catttactgg ctttgtgact   14700
tgggacagcc agtgccacca tttctttgtc tgcaaaatgg ggattttat tttgtagtgt    14760 cagtgtaaaa ctcagagata aggtacatta taaagcccct agcatagcac ctgactttag   14820
cagactcaca gtagattgca gctggcgtgg cagtaatggt aactgaatag taactgccat   14880
tctctgagct gaaagtgaga aaataaaaat aaagacacac tgttttagaa atgttagcag   14940
ctgtatttac aacttccctc tgttctctca ttccccatct ctcttcctac ttagtgcatt   15000
cgcatgagca cacacacaca cacacacaca cacacacaca ctcactcact ctccagcacg   15060
tgatctactc tgggattgac agagggtttc ctgacaaaca tccaacttgt aaggtggagg   15120
aaaagagaca tatgaaagca gcaggaaaag ccaccactct tgagggcaag atttgaaggg   15180
agtaaaaggg gctatgagga tttgtctgag tgctggtgac tcaactaaga agtggccagg   15240
cagagaaggg ctgtgggggt ggaggagac agaggagaag ccccagctgt aacatggtct    15300
gggttggtta tgactctggc atgctgccaa ggacagtttt tattgttctt gttttttcatt   15360 tgctttgttt cattaagaag tcaaatgtac taaatgttta tttctatcct gaaagttgga   15420
ggaacaagtt caagtcacac tgtttacgca tgtcagaaca gccaggttta cccttctttc   15480
```

```
tggtaacccc ttctttctgg aaacccttcc acttgtctt ggatttatgg ttgcctaaaa   15540
gctggatgcc agcccagcaa gataaaccag ggaggttagc catctgttca tttatgtttg   15600
ctgattcttt cagggttcct aattctgagg tgattttctt cacatgaaca aataaatgag   15660
atctcaagtc ctttctcact ggaaacttca cacactatga tgcttgtcag gaaaaattag   15720
gcaggaatac agagtgctca ctcaactgtc ctgacagtaa taggaagaga agtgcggtgg   15780
agtcgagagt gggggcggct gctcctgggc ctttgcagca gagcagaccg cagctgaggc   15840
agcatcaggc tcgcctttgt tttgctagaa cagaggaaag ccaagatgaa gtgagttctc   15900
tttgtgtcca ttccttctcc ttgccttagg gtctatccat aacatgctac agaatctgag   15960
tttcttagat tttcacttaa aaaaaaagat aagggaacat ttttttttct gcttacagaa   16020
gtaatttatt tctggtgtaa aaatccaaac aaaagcaaca gtgagtggaa gactcctcct   16080
aatccggacc tgaattataa ctgatacaaa ttctcgacac tcaaagttca cattttggtt   16140
tgtttatttg cagtctgtgc ttttatatta tttttgtatt tcagccgttt ttacagtaaa   16200
aatacaaggc ttttctccat taacagatag aggactgttg ggaataccag gtgttaggtt   16260
tctgttaacc tcaggcgctg tatttatcag gcctctactg ccacggtgag taacaagtaa   16320
ctccccagtc tcgttgctta taacaataat atgtgggtgt gcagccagct cagctggctc   16380
agtgaaacga ggctggactc caggcttctg gtccgcttta ggactagtct acacatctcc   16440
gttttagaac ctaggctgaa ggatcagcag ctacctgtgg cctgctcttc tcttttccaa   16500
gggtggcaac ttcaaggtgg cagatagaaa cttgccatgc atcttaaggc cttagctcca   16560
aattgataca ttgccattcc acccacatcc tgttggtcaa atctagtcac ttggcctagc   16620
ctgaagtcag tgaggcaggg agaatacttc acccttaggg gagtcatggt gtattaattt   16680
gctagggctt cccgaatgaa tacaacagac tgggtggctt aagcaacaga aatttgtctc   16740
atagttctgg atgctagaag tctgagatca aggtattggc agagttggtt tcttctgagg   16800
cctgtcttct tggcttgtag agggctgtca gttctgcgtg ttttcacgtg gccttccctc   16860
tgtgcttgtc tgtgtcccag tttcctcctc cagttaggac accggtccta ttagcagggc   16920
ctaccctcat gacctcattt aaccttcatc agctctttaa agaccccgac tccaaataca   16980
ggcacattgt gaggtattgg gggttaggac ttcagcttag gaatttagag tatgggggc   17040 attattcatc ctgtaacaca gaacagggt ggaaagtgca ggagggattg tgtgcagagt   17100
gcagtctcca ttgtcagcta acctcagtga ggctaggcct cctggttttt gaacggggga   17160
taggcagttc cattttaggg ttttggga tccaataaga aaatacattt aaagcccctg   17220
gtggtggagg cggtagggat ggatgtggtt tgacttgaaa aaggaccaaa actggccttc   17280 ttgggcccctt cccttgtta ttctctcatc tgggcaaact gggagtgtat ggtgcttttc   17340
agaattgctt aacttctaca gaagatacac catccatgga atcttcaaaa ataacaaagc   17400
cagcaggccc tttaggcact caatctgtgc cctaggtttt ggaaacacta tgcttcatgc   17460
ttctgcccaa gtgctgtctt tagtacccctt cctttacaat tattaattaa ttaactagtt   17520
aatttatttt gagacagagt cttgctctgt aacccaggct ggagtgcagt ggcacgatct   17580
tggctcactg caacctccac ctcccaggtt caagcaagtc tactgcctca gcctcccgac   17640
tagccaggat tacaggcacg caccaccaca cctggctgat ttttgtattt ttagtagaga   17700
cggggtttca ccatgttgac caagcacgaa ctcttgacct caagtgatct gcccgccttg   17760
gcctcccaga gtgttgggcc actgggcccg gcccctttac aaatatttat cgaaggcctt   17820
ctctgactta ttagaactgt gggctctatt ggtgtaagat atggccctgt tctcaggaga   17880
```

```
ctgcagttga atgcctgtga aatgattaaa atagtgatct aggaggtcag aatagggggc   17940
gtcccttcct ctgcttcttg ggtttaaagc caactattgc cttacatttt tgtaaatctc   18000
cttttggttt tttcctagaa aattgtgtta aggaatggta ctgaggcatt tgactcctgg   18060
gagaagcccc ctctgcctgt gtatactcag ttctatttct tcaatgtcac caatccagag   18120
gagatcctca gaggggagac ccctcgggtg gaagaagtgg ggccatacac ctacaggtaa   18180
gtcttgacca cctcctgtct tgaaagaaat acagagtgac cccaatatgg cctgagtcct   18240
tgcctcttcc caggagcaag gctccagggc tgtgtgggag cacactttct gatttcattg   18300
tctgaaacgc tgctgatgtt ttgtatgtgt gtgtgaaacc tcagcagaga atggctttgt   18360
agactgggcc aagtctcagc gtgttgtgtt ttgaagtgca gcggtttcct cctgagttgg   18420
cagactgtga ttattaaacc atgaagggtt actccttacc ctgacccttt taaggttgcc   18480
ccttgatatt cttatttat tttattttat tttttaaga dacaaggtct ggctttgttg   18540
cccaggctgg agtgcagtag agcagtcata gctcactgcc acctccaact cctgggctca   18600
agtgatcctc ctgcctcaac ctccctagta gctgggattg caagtgttca ccaccacacc   18660
cagataattt tttttgtaga gatgaggtct tgctatattg cccaggctgg tcttgaactc   18720
ctgggctcag gtgattctcc cgcctcagcc tcccacagtg ttgggattac aggcgtgagc   18780
accaccatgc ctggctactg cttgatattc ttaagtgact tttagggcct ccctccattt   18840
ccattcccca cataactagt tttaaagcag ttccagaatt tacttttgtc tgagacagat   18900 cttttctgttt cttacccgct cctttttctcc acctatcctg cgtataagca ataagcaagt   18960
agcagaggct gttagagtct ttgctggtga ccaccaattc caaacactgg ggaatcagga   19020 tcccttttaat catttttaaa cgattagtag agggagacgc ttgaatcaga gcattttctc   19080
tgttgcaatg ttccccttt ccctattaca atacctcctc cctctcccat acaataatct   19140
ttccaataaa gtctctcctt accaggttag aaaacaaatt aatagaggaa gcagacaaca   19200
agatctttct ttttcaaaac tgctgaatga taaaaatgcc tgacaattct gttgtaatcg   19260
attgctcaat aaattattgc tgactgattc atgtgctatg aatcagtact attctcagtg   19320
gtgggaattc agagataaaa atcctagttc ctgccttggg tgctcatgct ctgactctgg   19380
agtcagatga cccatttga ttcccgcctc tgcaacttac tagttctctg tgcttccatt   19440
tccttatcta taaaatgggg ataaaaatag gacctcctcc acatggtttt tacaaagatt   19500
gagtcaatga gtcatgtata aagtgcttag actagtgcct agcacataat tagtgatact   19560
taagtgtttg ctcttactat tagttggatt aggctatttt tgcattgcta tgaagaaata   19620
cctgagactg ggtaatttat aaagaaaaga ggtttaattg gctcatggtt ctgcaggctg   19680
tacacacatg gcacactggc tctgctcggc ttctggggaa gcctcaagga gcttttactc   19740
atggcagaag gcaaagcagg agcaggcacg ttacatggtg aaagcaggag caaggggtga   19800
ggaggtgcca cacttttaca acaacaagat ctcgtgagaa gtcacccact gttgtgagga   19860
cagcaccaaa ccttgaggga tcctcccta tgacccaaac agctcccacc tggccctacc   19920
tccaacactg aagattacag ttcaacatga gatttggagg ggacatccaa actatatcat   19980 tccaccctg gcctccaaat ttcatgtcct tctcacatgt aaaatataa tcatcccttc   20040 tcaatagtcc cccaaagtct taactcattc cagcattaac tcaaagtcc taagtcccag   20100 gtctcatcta gaaatgaatt ccttctacct ataagcctgt aaaatcaaac aagttatttc   20160 cttttcaagat acaatgggtg tatcagcatt gggcaaacat tcccatttga gaagggagaa   20220
attggccata agaaaggggc tacaggcccc aagcaagtct gaaacccaac agggcagtta   20280
```

```
ttaaatcata aagctccaaa atcatcttct ttgactccgt gtctcacatc cagagcacac   20340
tggtgcaagg ggtgggctcc caaggcctta ggcagctccg cctcagtagc ttttttatgc   20400
tgagattgca agctgatggt ggctctacca ttctggtgtc tcaaggacgg tggccttctt   20460
cccacagctc cactaggcag tgcctcagtg gggactcttt gtggagcctt cagctccgca   20520
tttcccctcc tcactgccct agtagagttt ctcttgaggg ctctgccctt ggagcaggct   20580
tctgctgggg cacttaggct ttctcataca tcatctgaaa tctaggtgga ggatgccaag   20640
cttccttcac tcttgcactc tgtgttcctg caggcttaac atcacatgga agctgccaaa   20700
gcttatggct tgcaccctcc agaggagtgg cctgaactgt acctgagccc ctttgagcca   20760
tgtctggagc tggagtggct gggatgtggg aaacagcaca gggaagtagt gccctggcc    20820
tggtccctga aaccactcag tcctcttagg tctcagggcc tgtgatggaa ggggctgtct   20880
cagagatctc tgaaatgttt tcaaggcctt tacccattg tcttgactct cagcacttgg    20940
cttcttttta gttatgcaaa tcgttttagc aatggttgct ctacagcctg cttgaattta   21000
tctccccaca aaaatatttt gttttgtttt gttttgaga cagggtctct gttgccaggc   21060
tagagtgcgg tggcatgatc atggctcact gcagccttga cctcctgggc tcaagggttc   21120
cccctgcctc agcctcccaa gtatctagga ctacaggcaa gtgccaccat gcctggctaa   21180
tttttaactt tttttttttt tgagacagag tctcccctatg ttgcccagac tgcggaaatg   21240
cttttctttc tctgccacat ggccaggttg caaatttttcc aaacctctat gttctgcttc   21300
cctttttaaaa ataaggtcca actttaagtc atttttttac tcccacatct gagtgtaggc   21360
tgttagaagc agccaggcga catcttgaat gctttgctgc ctagaaatct ctgccagata   21420
tcctaaatca tcactctcaa gttcaaactt ccacagatcc ctggggtgtg aacacaatgc   21480
agccaagatc tttgctaagg cataacacat gtgaactttg ctccagtccc aataagttcc   21540
tcatttccat ctgagacctt ttcagcctga acttcactgt ccatgtcact gtcagcaatt   21600
tggtcacgat catttaatca gtctttaaga cattgcaaac tttccctcat cttcttgtct   21660
tcttctgagc cctccaaact cttcccttct ctgcccatta cccagtttca agctgcttc    21720
cacattttcc agctatcttt atagcaatat ttgactctca gtaccaattt tctaaattag   21780
gttgttctta cattgctata aagaaataac cttcctgggc atggtggctc atacctgtaa   21840
tcctagcact ttgggaggcc aaggtgggtg gatcacttga ggtcaggagt ttgggaccag   21900
tctggctaac acagcaaaac cccacctcta ctaaacatac aaagattagc ctggcatggt   21960
ggtgcccacc tgtattccca gctagtcagg aggctaaggc aggagaattg cttgaacctg   22020
ggaggcagag gttgcagtga ccgagaaca tgccactata ctccagcctg ggtgacagag    22080
caaggccctg tctcaaaaaa aagaagaaa gaaagaaaga cagggaggga gggagggagg    22140
gaggggagag agagagaaag agagagaaga aagaaaagaa agaggagag acctgagact    22200
gggtaatta cttaaaaaag aggtttaatt ggcctatagt tccacaggtt ctacaggaag    22260
catgatgctg gcatctgctt ggcttctggg gaggcctcag gaaacttata atcatggtgg   22320
aagtaagaga gggggagcag gcatgtcaca tggccagagc aggagcaaga gagggagag    22380
gtgccacact ttacaacagc cagatctcgt gagaactcac tatctcgagg acagcactaa   22440
gccatgagga atccttccca tgacccaaac acctaccagg ccccacctac aacattgggg   22500
atcatatttc aacatgagat tttgagggga caccaaaact atattattgg tcttcgtaga   22560
ttaattgttt tagtctgtac aagtcaatat gtagaattat aaagatgaac cctgttgcta   22620
tatgaagaaa tctaagaaaa tacttgggtc ctcatttaa aaagccattt tgtatgtgtt    22680
```

```
ctatgcctga tgaaacactg tgtactgggt agagaaagtt tgtattttaa gctctcccac    22740
tggcaataat tagaagttga accaggatca gtatctaagt gtcccattgt ttgttgttgt    22800
tgttattttt aaatgaaatt ccttaagatg tgatggagac tctgcaaact atccaaaata    22860
gtgtcattcc aacatgttag caatatttag aattattaat gagatacttt acaatctttt    22920
tttatactgt ctttgaaatc ctgtgtgcat tttacactta tagaacattt catttcagac    22980
tagccacatt ttgaatgtgc aatagccaca tgtgtctagt ggctacccta ttagacagca    23040
taattccaac catactccca tgatttttt tttgtttgtt tgtttgtttg tttgttttg     23100 agacagagtc tcattctgtc tcccaggctg gagtgcagtg gcgcgatctt ggctcactgc    23160
aacctttgtc tcccaggttc aagtgattct tctgcctcag cctccccgt agctgggatt    23220 acaggcacgg ccaccacgcc tggctaattt tttgtatttt tagtagagac aaggtttcac    23280
catgttgacc aggctggtct cgaactcctg gtctcaagtg atccaccgc cttggcctcc    23340 caaagtgctg ggactacagg cgtgagccac catgcttggc cactcccatg atttataagc    23400
tccccagaca cactgccttg ccagtattca tgctgttgct tcagtcaaga atgaattcct    23460
cagcgctacc tctcttgacc ttcacatctt acttagtgca aatgctgtct cctcctgaga    23520
cttgcctgac ttcggatact ctccctgtta catcttattt aaaatgtcaa gtagactggg    23580
cacggtggct cacacctata atcccagcat tttgggggt tgaggtgggc agatcacttg    23640
agcttaggag ttcgagacta ggctgggcaa catagcaaaa ctccgtcttt aacaaaaata    23700
caaaaaatta gccaggcgtg gtggcatgtg cctgtggccc cagctacgtg ggaggctgag    23760
gtgggagcat cgcttgaacc tgggaggtgg aggttgcagt gagctgagat tgcaccactg    23820
cactccagcc tgggtaacag ggtaagaccc ccatctcaaa aaaaaaaa aaagtgtcaa    23880 gtataccact ttatagcact tgtaaagtgg tatgttgatg tggtttggtt gtgtccccac    23940
cagccaaatc tcagcttgaa ttgtagtttc cataatcccc acatgtcatg ggagggaccc    24000
aggggggtaa tttaatcacg ggggcagcta ccctcatgct gttctcttga tactgagtta    24060
gttctcacga gatctgatgg ttttataagg gacttttaa aaaaccctt tggttgggtg    24120 tggtggctga tgcctatatt cccagtgctt tgggaagtca aggtaggcag atcacttgag    24180
gtcaggagtt aagaccaat gtggccaaca taatgaaacc ctgtctctac taaaaataca    24240
aaaagaaaaa aaaattagct gggtgtggtg gcacacaccg gctaaggcag gagaatcact    24300 tgaacccgg aggcagaggt tgcagtgagc tgagatcacg ccaccgaatg ccagcctggg    24360
cgaccgagca agactttgtc tcaaacaaca acaacaacaa caacaacaga caaacaaaaa    24420
cccttttgct gggcacttct ccttgctgct gccacgtgaa aaaggacgtg tttgtgtccc    24480
cttctgccat gactgtaagt ttcctgaggc ctccccagcc atgctgagct gtgagtcaat    24540
taaacctctt tccttatataa atgactcagt ctcaggtatg tccttattag cagcatgaga    24600
acagactaat aaatatgtgc atccattatg acagtgacta attgcatttt aataattggc    24660
ttaggtatct gtctttcttc ccaatgtact ggaagctcca tggggtgcag tgaccaagtc    24720
ctttggtctc tgactgtcta ctatttaatg aatatttgtg gaatatgtaa attaaacatc    24780
ttcaactgtg gtttaaattc ataggacaca tggaaaaact aacactatag gacacaatta    24840
ttaaaaagta tttaaaagta atgacaaaaa acgcagttac tttgcaccca cctaatagcc    24900
ggaaccatag gacttagttc aggaaaccca aatataggtt caagaaaggg gaatcaggcc    24960
ctgaaaatga atggctttgt taggaatatg catatgtgca gtgcaggctg ctaagagctc    25020
cttacagggc tgagtgggtc gtgagatctg ggatttgtag aaaaacatgg ctttttaggg    25080
```

```
agctgtccaa accttctatg gggcctgtta gtctctacat gtgccttttg cggtcattca   25140
ctggatttga tttctgtcac ttgtggcttt atgatgctat tgtttaggct ggataagaca   25200
gaacattcca gaagcttctg ctccagtgtt ttctcccaac tgagtcagct gactccatca   25260
attgtatgcc aggggcctg gggcaaagga aggggagggc atgtagcccc tttcgccagt    25320
tagtacagat tggtgtggtg gtgggaaacc tctgagatgg ggaagggcca agcaagactg   25380
tggagggcct aactcatctg acacaggatt tacagtggca catttcccaa acctttcaca   25440
tactggggag ttcagaatag taatgttttt ggaaaaagat gatgggcatt ccaaatgttg   25500
ataacagcca gtcagtctgg tttaaggaat gaagtgtatt atttacatttt ttgtaaagct  25560
gcagattgag cagccctgga atgggtctgt gaatacaagg ctcattggcc tcatgatcct   25620
tttgctcagg gacatatttg tataaaattt gtatcaaagt tgtggtatcc catgcttct    25680
gcagcctttt tgaggtttat ttttatctt gtcagatacc ttttctatt ttgcctacca    25740
tttaacattt caagaattaa aaaagaaaac aatttgtcta agggcacttc caattaattt   25800
gcgtatttct aagaagtatt tactaaattt acagtatccc gtgaaatatc ttattttggg   25860
gtttcttagt tttgctgttt ggattattca tttctatttt aggcttgtat tatttaaaaa   25920
gatgtaaggg ctagatctta agttatttta ttattcattg ataacaagta atactggatt   25980
ttcaaatata atcaacatat ataatatata cagcattatc tttaagagtg tagactatat   26040
tttatattat aaaaattaca catatatatg tgttccatat atataatcac taaagatcaa   26100
cttgaaaatg cagtaaagtt ttgaacaaaa actactaatc catggcttca ctgtctcaaa   26160
aataaccaat gctaactaac attttagtgg atatcttctt ggccattttt ccatggatga   26220
gttttagatg gttatcatac tatgtacata tgcatgtaca tatacaaaat atacatattt   26280
tttattcacc taatgttata gcataggatt tttcaatgtt atattttggt cttcatacaa   26340
atgaattta atgatgatta tatttaatag agtaaatgta ttactacact taactgttcc    26400
tttcctgaac atgtagatcc gttttcattt tctcctctgg ttacctcgtg ggttgaatgt   26460
tctcctcatg tttgccagcc agttgtgttt ccacactttt agttcttgtc ctttgtccat   26520
ttgcttatct gggttctgga gtgttcatgg cactctgtga acctttttatg tttcatttgg  26580
ggcaactgct tttccattgt ttaccttgtc aattttaaa atgtgttgta gtcaagtcta   26640
ttcttttca acatttctat caggtctgag ctttaaaagt cttactccct tcaatggttt    26700
gatgttcaag tcgattttct tatagttctg ttttccaca tttaatttct tcaggatcta   26760
agtgtcttcc ttgcaatta gcaaaggcag gaattttgtt tatactgtct aattctgtcc   26820
tattaaccct ttagttcttt aaccgtgtct gagccaagct gtataagaaa ttttttaac   26880
ataaagagac aacaaaaaat ttaggaacac cgtgatcatt gtttccatta ttataggaga   26940
atgcttctc cttttttcta aacttgcctc gcttttctct gatagtgttt ttagattggt    27000
agctaaaact gtatttgttt tgccaaaata gaaacagatt ttgaaaaaaa aatccttaa    27060
actgctcaga agtaaaaaaa aatagaaaaa gatctctcac accatcttat catgcacaaa   27120
aggttgtgac caggtatgtg tgagttttaa atgcacgtgg tacattaggt gaattgccta   27180
cgtgagccta tgggtcactg cctggggaca gggagaccag ggagatattt ccatcttaag   27240
gagtgaaact gtttcttgca cactgtcaac aagcgggtga gtcttctccc gaccctgctc   27300
ttaccacttc ttctcagtat cctgctttgt atctacaggt tgctgccttc agttacctga   27360
gcgggcagcg tactcaaagt taagggtaga ggctcctcag cctgtgcctt tggctggctc   27420
cccttgcttt ccctcttctc tgtggtcacc ctaggacttc agtactcctt tcacgttgat   27480
```

```
gtgttcatca ccccagcctc gcctggatct gtgatggtct tttaaagcgt gtcctcctcc   27540
tccaggacca cagctttctc actccccaca tgggaatgct ttcatgcttg ctgcccacct   27600
tcgccccacc gctgcctctg ttggaacacc cccttcaccc tcccacctgc agaagcccac   27660
tctttccaga atcaagcaaa agtgtctttt gcaggagtcc ccttccagtt gccatccctc   27720
cctcctctgt atgcccacag tgcgtttact gtgaaggagg tggcctctga aggcagtctc   27780
ccatgctcta ctgtggattc ttggaggacc agaaccagga cttaatgtca caccatctca   27840
agagcttagc acaagccgtt gcacatggta tcagtagcta atccctccta agcagcaggt   27900
gtgccaggta gtgttgtaac tggatttatg tggatttcat tctcacaaca accctacaag   27960
gtgagtacgt tattacctcc attttacaga tgaggaaact gaggcacaga agcagtgagt   28020
aagatgaaac cagggttgaa tgttaaccct accagccaga tctcagtcta gtttgtatcc   28080
agtgtatgcc caatcacttc ttaatagtaa ttctcaacag aggattaggt gaatgaagga   28140
accaatatga ctgaaagata acgatactat gatagtatta tacgcatcca atttatcaaa   28200
cacctctgag gaattagata taccgatgtt aattttccac ctaattaaaa ttattccttt   28260
tgatttccac tccttatctc agtctattgt ttctaaaatt atttctaaaa ccaaccatga   28320
attttcctgc ctgattaaat agttcatgga gcataactga accttgtctt aatgacaagg   28380
accgtcatag taatgcacaa atgttatact atagctgag attcattagc atctactaaa   28440
taccagggac catgccgggc acttttaagt atagttcctt gattaattgc ctaggctgaa   28500
aatttgattt gttttttgtt gttgttttg ttttgttttt tcaaactctt ctttgtattt   28560
ctgaaagttc atttggtctt ctttgatctt gtaggacagt aactgatcaa tatgcccctc   28620
tctgcaggca ccagccttgg cttacacaaa agtttggctt tgaaatttcc tctcctcctc   28680
catattccaa taaattactg tgaattaacc tctgtgtaaa atcaaggaat accctgaatg   28740
agaggtgagg tcaccaggat tctaaacctg gccctgacac tttcgattgg tcctgaatcc   28800
acatatcctt atctataaaa aggtggagtt aatgatttct aagtgaaggg tctttggtta   28860
taagcaaaat aaaactacctc tggctaattt aagtaaaacg ggaatctatt tgaaggctat   28920
aaagtaggtt aacagaatca aggaaagcag cttggaagac aaaagcagga tgcagggcag   28980 cttttaaagat ccaggtcacg agagtgtatt gatcatcaca tcatgtgtct gccactggga   29040
ggaatcctgt cttttactga gtttttcttgt tttaaatta aaatttttt tttttttggt   29100 agagacaaag tcttgctctg ttgctcatgc tggaatgcag tggcatgatc atagctcact   29160
gtaacgtcaa actcctgggc tcaagccatc ctcccacctt agcctcccaa gtagctgaca   29220
ctacaggtac atgtcaccac gcctggttct tttactgtgt tttctatctt gaggcactgt   29280
gctcaggatt cagaggccag aggaaaggaa ttggttgagc tcaggtccca tagcaacctt   29340
gactgatggt cttacacagc tgtacaatac aagagaggaa agcaaatcag ggctattacc   29400
agcagaaagc ggaatggttg tctaacaaat gaaaagtcca ctgcaaacac tgaacttcaa   29460
gctgtgtaag tggtttaaca cggaagtgtc tatcaaattt ttaaatatat tctttgtaaa   29520
ctggaagggc atgtaatta tcattagatt tggcttggt tagaggcatt tgttagaggc   29580
attagctggt ttcatcctac aggcgtttct taggtacctg ttaggagagg ttgtctcata   29640
cagagagagg agcaccttgt gctaatgaga aagacttggg atcaagttct cactcttctg   29700
cctgtgctct gtgtccccag ctgtgaagtg gggcaatact acatgctgta tttgtactac   29760
atacttgtaa ggattaaata aaataaaata atgtgggtta aactctttga agagctatgc   29820
aagggtcagc tatttatagg attagtgggc atagcttggt gcttagtgtg atatgatgtg   29880
```

```
tgatatgtgt atatgtgata ggaagtatgc ttccttctat acacttgaca gagtatagga   29940
tatagacatg tgatatgatg aaatatatat ttagtcttcc tccatttcct ggcatacagc   30000
tcctaagatc cttggaatcg cttaagtgat aagtgtcttt ttgtatgcta gtgaattgac   30060
tgatgactgg cagcctctat ggctcctgga tgggagctgg tcctgaaaga agaggacagg   30120
attagagggt tgggactttc agccccaccc cccaacctcc caggagggga gaggggctga   30180
aagttgggtt gatcacaaat ggccagtgat ttaatcaatc atgcctatgt aatgtagctt   30240
ccataaaaaa ccaaaaggac tgaatttgga gagtttccag agaaccaaac atggggaggt   30300
tcctggagag tagcgagcct gcagagggca tggaagttct gagctccttc ccctacacct   30360
tgcccagtgc atctcttcat ctgtatactt tgtaatatcc tttataataa aatgtaagtg   30420
tttccctgag tactctgggc tgttctagca aattaattga gcccaagcac aggggatgg    30480 gaaccccaat ttatagccat tagttcagaa gcacaggtaa aacagcctgg ggcttttgat   30540
tggcatagga ggtggaaggc agtctcaacc tgtagaatct gatgctatgt ccaagtagaa   30600
agtatcagaa ttgaattgaa ttggaggaca ctgcagaatt attggtgcag agaaaacgcc   30660
acacacttct tggtgaccag aagtctcaga agtcttagaa gtcttctgtg taagttgtta   30720
cagtatgaga gcacagaaaa aaatggtttg ttttttctac tggagaagat acaaagactc   30780
atctatttgt atgcatctat atgaatgcat ttattttctc atctgttttt attttaaagt   30840
ctagaaggga tttaagaggt ataaagagat acaatataca gacagtcctt gacttatgat   30900
ggttcaactt gaatgatgtt ttgacttcgc gattgtgtga aagtgatgta tttggcatgc   30960
ccctccaatg acgatagagt tacatccaga taaacccatt gtaaattgga aagatactaa   31020
gttgttgaat caaaaacaaa cttcaacttt acgatgtttt caacttatga tgggtttact   31080
gggacataac tccatcatca ccgaggcgca ttttacgta  ccagtttcag ccttcagctt   31140
gcttgcagtc tacctgaggc tacatgataa tttcacaatc taaatgatgt cactcagaag   31200
tttctaattg aatgctaaag acatgtacgg acatccacag gtgggtgaga aaaatccctg   31260
tgctgctatg gttgggaaag gcctcagagg aggtgtgggt agcccagctg gccaatgcct   31320
tcctaacctg tgctcttaaa ttagctctgt tcaatagaaa tattacatga accacatgtg   31380
taatttaaga ttttaagatt ttctagtagc cacattttt  aaaaagtaga aggaagcagg   31440
taaaattaat tttgataata tattttaatt ttacccatta taactgaaat agcatcattt   31500
caatatataa tcaatataaa aaaaggttgg cactgttttt gaaattctgt atatatttta   31560
cacttacagc aaatctcaat tccagttagc cacagtttaa gtactcagta gtcacatgtg   31620
actagtggct accatgtcag acataataac cctagctggt ttaggaagaa ggaaagataa   31680
gcaaagggaa agaaacaaaa gtcactggaa tttattgaac acctactatg taccaggcag   31740
ggctagggct agggctagtg tgaggcattt gatgaacaaa agatcagatt ctgtttttat   31800
ttaaaatttt gttcatcata aattttttggc ataaattttg gttttaataa atagtgcatt   31860
aaactattta tcttgattac tacttgttta ggcacctctt acatcactca cactgactct   31920
aggcccagcc ctggcaccag gcgctttcta agaactttct aatgcttcat ttgggggctc   31980
taacttgaac caaactgtgc tgtatatcag aaacagagac cgggtgtggt agctcatgcc   32040
tgtaatgcca gcatttggga aggtcgaggc aggaggatca cttgagtcca ggagttcaag   32100
accagcctgg gtagcatagt aagacctcat ctctacaaaa aaataaaaca attagctggg   32160
tgtggtggca tgcttctgta cttctagcta cttgggaggc tgaggtggga ggattgtttg   32220
agcccaggag gctgaggctg cagtgagctg tagtcatgcc actgcactcc agcctgggca   32280
```

```
acagagcgag accctatctc aaaaaaagaa acaggagtga actcctgtaa tttactaagc    32340
cttgggcatt attttttaaa ataaaatttc aatttaattc aatgtagaaa caagaagaca    32400
ttggtaaaca aattgaaatt caaactaaat ctgtgaacca aactgaaaat tttgaaaata    32460
cttcaggacc aaaccataac ccaggagaga gttcatcggc tttgattccc ggtcaaggtg    32520
accctcaact attgcacctc cctaatcagg aagaaaaga aggaaaacaa agttttgag    32580 aagactctat cctaggcctc gtttccttcc cacattatag cttcgatctc cagcttttta    32640
aggcttagta gctgcagtct ctatataatg ttatattggg aatgttatat tgaaaatata    32700
acttggatgc tgaagaaag gaaagtcttt gcttattaaa gtggtgtcta ttttcaaata    32760
aaaccctttt ctttctttta gggaactcag aaacaaagca atattcaat ttggagataa    32820 tggaacaaca atatctgctg ttagcaacaa ggcctatgtt tttgaacgag accaatctgt    32880
tggagaccct aaaattgact taattagaac attaaatatt cctgtattgg taagtaggca    32940
ttttaatacc attaagttgg attttggaag aaaggaaaaa gctaagttaa tgctctttat    33000
gattttacat ttaggagcca ttaagttatg ttgaaatata catatataaa aagaaaata    33060 cttcttttct tttctttaaa gtacatcttg gactttttc taagatgtat caaataaggt    33120
cttttcaaat gatgacaaaa ttcagatttt aggatttgtt ttcataattt cttcctgggt    33180
gttcaggatt agcaattgtg caaataaata tgccctagg attttttggt agctaataat    33240
tttaaaaatg tttatttgcc cctgttttc attcagaaat tctagcaatg aaatttgtat    33300
accatttctt acttcagatt tttatgttgg attttatact ctcaaaattc ataaattgac    33360
accagaaatc aatagactgg cagcctactg tgatttcagt gggctctgtt tataatggta    33420
attctaccta ataacgacac ctattctaca tctattctat actgagaccc atgagacttt    33480
cttttttttt aaattaaatt aatttattta ttattaattt tttttgagac agggtcttgc    33540
tctgtcgccc aggctggagt gcagtcagtg gctccatcac agctcactga agcttctacc    33600
tcctgggctc cagggatcct cctgtgtcgg ccagggactc caggcgtgaa ccactgttcc    33660
tgggctggcc cagtaaacat tctaattcac ctacaccaac ccctgccgac tctcccaccc    33720 taaccctag gtgaccgctc catatgcagc tggacactga tgatggaccc aggacctaga    33780
cagtatgagg tccctgccac ctagtcccag gggtgtaggt cgggtttata atgagcctct    33840
ggccctgctt aggcggaagg tagcgccacc ttgtggccaa agatgccac atgtttacaa    33900 gagcttttcc ccttttgtgg tgtctggata actcagagcc tgcaaatggt ctctttgtaa    33960
atattacact tacaaaatgc agtactggga aaggacagag aagaggcttt gtcttccata    34020
tgcagccaga aaggagctca ctgcctgatt tttcagctat ttaatctcaa cctttacatt    34080
tatatttcca acccctttg ctatggggta gtaggagaga gtggatggag gtgctttgga    34140
ggggatgctg ctgtcttaat atacctctgc tccgcagact gtcatagagt ggtcccaggt    34200
gcacttcctc agggagatca tcgaggccat gttgaaagcc tatcagcaga agctctttgt    34260
gactcacaca gttgacgaat tgctctgggg ctacaaagat gaaatcttgt cccttatcca    34320
tgttttcagg cccgatatct ctccctattt tggcctattc tatgaggtaa gtagattttt    34380
cttttcagaa cctctttttt tagctgacag tgggttgggg caccccaagc cagattaact    34440
ttgagtttct tctagaaatt gcctagagtt aagttatctt atagagtgtg tgaaaaatgg    34500
agtgtttttt ggaaagaaaa aaaacttgag gccgggtgcg gtggctaatg cctgtaattc    34560
caggactttg ggagaccgag gtgggtggat catttgaggt taagactttg agaccagcct    34620
ggccaacatg gcaaaactct atctctacta aaaatacaaa aattagccag ctgtggtgat    34680
```

```
gtacacctgt aatctcacct actcaggaga ctgaggcagg taagttgcat gaacccagga   34740
ggcagaggtt gcagtgagct gaaattacac cactgtactc cagccagggt gacagagcaa   34800
gactctgtct aaaaaagcca aaaaaaaaac aaaacaaaaa acaaaaacaa aaaccctgga   34860
gtgcagtgga tagttgggaa gttggtaaaa gataaaataa ccccaggaag aggattagat   34920
taggggtgtg ctctgggatt gtgatgggtc tcctcagctt taaatttgta gctgttttct   34980
ggctctgcct gttcaagagt cttaccctct tcatgtaatc ctgtagcatt ccagttttta   35040
tggcaaacag caataattgt gtccctgggc cttcaaggtt atataaaacg tagaaattgt   35100
taaaatagaa ttgtgagcaa gtttttaaaaa attatatgtg tgagagacag gagtcctaaa   35160
agtagggcct caccaactct gaatgcatca ttcgggagaa gcagaccagg caggagttcc   35220
ctagagggtc ctgtctcaga ggaatacagc ttcacaggac cagaggaagc acagatttcc   35280
tgtcaagccc tgactgaacc tcccttctag aaataatttc aggagagcct cctactgaga   35340
gatattatgc aaaggttccc tcgaggccct tttgttccca gtggcttcaa tccatcagcc   35400
aagtagatct tgttgctaat atctcactgt ttctcagata atttgcatta tataactcac   35460
tttttttgtt tttacatcat tgaattcacc agactgatag ccacactatc ttatgtggtt   35520
gtgaggattt catgagatga ttcatgcaaa aattttagaa cagagccagg aatattatac   35580
tcaacaattg ttcactccta ttattataga ggagctacta cctgtgctat ttctgagaaa   35640
tcatagctac atgcccaaat aaagaatttt aggaatgtag tgtctgtatg tgcccttaag   35700
aagtataact tggagagaat atacaattga agaaaccttaa attgaaaata gggctatatt   35760
aataccgtct tcttccagtg tagctattct ggtataattg gtcctggtcc tggacttagg   35820
cttttaaatt tgttattatt gagaaataat tcacttacta taacatttac cattttaaaa   35880
tgtacaattc agtagtcctt agtatagtca caaggttgtg caaccattac tgctaattcc   35940
agaacatttt cattatccca aaaaagaaac tgcatactct cttagcagtc actcctattc   36000
ctgtcttact ctcccaggcc ctggcaacca ctaatctact ttctggctct gtgaatttgc   36060
atattctgga catctcatat aaatggagtc atataatata tgcccttctg tgtctgcttt   36120
ttaaatttag tgtaatgttg tcagggttca tccatgttgt agcatgtatc agtgttccat   36180 tccttttttat aactgaggaa tattccgttg tgtagatata ccacattttg cttatccatt   36240
tatcagttga tggacatttg ggttgtgttc cttcttggct attattagaa gtgctgctat   36300
gaatatttgt tcatacaagc ttttatatga acattgggta tataccttga agtggaattc   36360
tcttgagtat atacataggt gtggaatttt ggagtcctat gaattctgtt taactttgtt   36420
aagaactgac aaactgtttt ctgcagtgac tgcaacattt ttatattcct gctagcaatg   36480
tataaaggtt ccaatttctc cacatcctca ccaacgctta ctatttttct ttttttttt   36540 tttaattgcc ctcctagtgg gtgtgaagtg gtatctcatt gtggttttga tttgcatttc   36600
cctaatgact aatgatgctg aacatgtttt tatgtgctct ctggccatta gtatatttc   36660 ttttcagaaa tgtctcttca aatcctttgc ccattttaaa attgagctcc tactttttaa   36720
aaccataaaa taataatatg gttaatatag tatttagcaa aatagtcact attttctggt   36780
cctggttcag tcttgtgtag cagttaggcc ctagtaggac agttagatga agattaaatt   36840
ttttagttac tgtatcagtt agggttgcca gagaaactga atcaagaggg tgtatatgta   36900
gagatgagaa agagggagag aaagaaattt atattatgga attggcttat gtgattatgg   36960
gagctggtaa gtctgaaatc catagagcag gccagcagct ggaaactcag gtaaaagttg   37020
atgatgtggt cttgagtttg aaatctgtag ggtgggctgc aacctggaaa tccaggcaga   37080
```

```
atttcgatgt tgcagtcttg aggagaattc ctcctctaag aaacctctgt ttttgcttgt    37140
aaggctttga acagattgga gggggcccag ccactcatta ttgagggtaa cctcccttaa    37200
agttaacgga ttgtagatat taatcacacc tacaaaatac cttcaccaca ccatctgggc    37260
tagtgtttga ccaaacaact gggcaccata gtctagccaa gttgtcataa aattatcaca    37320
gttactttaa atgatcatat tcacatattt tcagaaaaat gggactaatg atggagacta    37380 tgttttcta actggagaag acagttacct taactttaca aaaattgtgg aatggaatgg     37440
gaaaacgtaa gtcaaatgat ttatcagtgg aattattttt tcagttttca tttaaactac    37500
atgtctactt ctacattgct taaaaatgtg tttagccttt tttggatgaa aaatataaaa    37560
acatgtaaat agtcttgtaa ttattattct acaaatcaag atggtggtaa aacatcttac    37620
agattaaata ttagtgattt gtagatttat catggccagg catgaattac aggccagtga    37680
aaagtcccac tcttgcttag tagtcattga gtgatgtgta gtagctacag cacaaatact    37740
tttcaaacca ccacatgttt tgggctattt ggccattgcc tctatgaaag ctgatttggg    37800
ccagggacct actttttctc cccctttgatc taattaaaac tgttgtgtct gtgtatgaat    37860
aagatactgt ggatagacag ctccagttaa atcttgcaaa gtcctgacca tttaagagaa    37920
tctaaactca aatgtgatca tctttactct ttcttgtgct tatcaattat aggtcacttg    37980
actggtggat aacagacaag tgcaatatga ttaatgaac agatgGagat tcttttcacc     38040
cactaataac caaagatgag gtcctttatg tcttcccatc tgacttttgc aggtaaaagc    38100
tttaaagata agttctttt caaaataag gtctttcact gcaagaccac caaaagcatg     38160
aggaatatat gcagacacac ttattatgca tggatattta tgcataatca gtgataaatg    38220
ctgatggcac atcgagacag tatagtgtac tggttcacag cacagacttc tgactgttgg    38280
tttgaatctt ggctctacca cttatagctg tgtgaccttg ggcaaattac ttaaccactc    38340
tgtacctcac tttccttatt tgtaaaacaa agatagaaat tgttaactat gttagaggtt    38400
gttatgagga caaatgagtt agtattagtc aaatacttag cccagggccc atcacacagt    38460
aaccaatatt aagtgttggc tcttagttac tatgatatgc tctgtcaagc atcaactgac    38520
ctggtctact tccagtcaat aggtagtctc tacatggaag ccaaataaaa gatactgttg    38580
tccatatttc agcagagtgg tttcctcagg ggaggcagag aaggaatgga atcaagagca    38640
ttacgtagac aggttcagtt atatccataa tataattttt atttgtctaa gtggcagata    38700
caaaggtatt tgttagagta ttttatctct ttctggtgcc taaaatttt cattaaaaaa     38760 tgctgtaggg gtggtttggt ttgtgcagtg aaaccaccta tgttattcac aaccttgcga    38820
gagatgtatc aacagctctg gttcagagat gaaaagtga ggcccagaag gctcttccgg     38880
ccagccttca aggaagggc tgaaggctca gtggtgactg tgtacatcaa agtggttagg     38940
cactatgcag tgtaagcagt ggtcatatta catgggacta tgtttgaaat cagtaagaat    39000
gaaaggcaga attcgttga actccattta aataaatgac tggggcaaaa tatggaatct    39060 gattttctt ggaggggggg attgagtatc aaagtgtgta ttccaataaa gtatctgtcc     39120
aatgtgacac ttttcaagtg cctaagaccc tacgaggcca cggccatcgc tgcctgttct    39180
accttagctt tggctctgcc gtgccctggc ttccctggct ttgccggtgg cccgtccaca    39240
ctggcatatg tccatgcagg tctagagagg cctcttattt cttttttatg tgagtctcca    39300
ttctaaatgt tatcatctta attttgtacc acatattgtt ttttcttgtt tggatgatat    39360
caccgttgct acaataaaca ccttccacta caattcatct tctgctttat tacacgttga    39420
gttgacagaa tgccttccaa acattccttt ctacttaccc tgtgagcttt tggccatgtt    39480
```

```
gtacctgaga actgttgcta acttgcggat tcgggcaga ttacactgac cagagtccac   39540
attcactttt tattcttaca tcctaacagg tcagtgtata ttactttcag tgactatgag   39600
agtgtacagg gactgcctgc ctttcggtat aaagttcctg cagaaatatt agccaatacg   39660
tcagacaatg ccggcttctg tatacctgag ggaaactgcc tgggctcagg agttctgaat   39720
gtcagcatct gcaagaatgg taagaactca gagaggggac atgatagggg tgtcaagaat   39780
gcagaaggat tggagttcaa caaagaatat gtagctgggc gtagtggcgc acacctacag   39840
tcccagctac taaggatgct gaggtgggat gatcacttga gcccaggagt tctcaagtcc   39900
atcctgggca acatggcgag accactgtct ctaaaaaaca aaacaaacaa aaagaatat   39960 attgtcagcc aatagaaaag atcagtttct ttcaagaaca atgtttcata acatggctat   40020
tgaatggtaa aaaaaaatca tggcttttct gtgatgcttt ttatttctag aatgccatgt   40080 tgtgttttt tttctggaca gtggtttaga agtcttaaca gtaataatag ctcatgttta   40140
ctaagcacct gatgtatgcc agtcactgtc ctaagtgctt tacatattta catgtagtta   40200
atgcatgcaa acattaact gatttcatgt tcaaaacaat gctaaggctg gcacggtgg   40260 ctcatgcttg tattcccagc actttgagag gccgagatgt gaggattgct tgaggccagg   40320
ggttcaagat cagcctgggc aacatagcaa gaccctgtct ctacaaaaaa aaaaaaatta   40380
aaaaattagc tgggtgtggc ggcacacacc tgtagttaca gctgctcagg aggctgaggc   40440
agagagattg cttgaaccca ggagttcgag gttgcactgt gctatgattg tgctgctgca   40500
ctccagcctg gcaatagag tgattccgca cctccccacc aaaaaaaaaa aaagctaaa   40560 agaaaaagtg gacaactcag ttttaagaaa gtacgtatca tggcaaagat tctcagtgat   40620
tttgaagcag agttagtttt aaaccctgac acaaatgtcc cagtgtttct taatgtcaga   40680
gctactctgc tcctttccat gaatgaggca gaattatcag tggcacaact gacaaaacta   40740
ttttcttcat cttgaagagt agttttaaca gccacatgtt gcagaattat tcacaatgaa   40800
cttactagat agtagacatt cagcggcctg tttttataat tggggaaact agggctcaga   40860
gagggaacgt gattttgatg cgactcctcc ctctgagcag atccctggcg gaactcaggg   40920
tcttctcata tttgccctgt gattccctct tgggctgtaa ttcctctttta aaatttctct   40980 ggagagctct ctgtgtagtc cctttctcct gaatagtaat gtgctcactt ttgctccctt   41040
atctatctca ttttaaaatc tcctttcagg cctggcatgg tggcgtgtgc ctgtagaccc   41100
agctactcag gaggctatgg tggaagggtc gtttgagccc agtttgattc tagcctgggc   41160
aacatagcga gactccatct tttaaaaaag aaaaaaaaaa aaagaataag atatcatttt   41220
ggaataagtc tgaagtcagc agtataccct ctgatccttg tctgacaggg cagtgacccc   41280
cacacctggc tttacatcag aattatctgg agagttatta aaaatatatt ggtgaggcat   41340
ggtggatcat gcctgtaatc ctaacacttt aggaggctga agcaggaggc tcacttgagg   41400
ccaagaattt agacctgcat gggcaacagg gagacccat ctgaacaaaa aatttaaaaa   41460
ttagctgggc atagtagcat acacctatag ttccagatac ccaggaggct gaggctggag   41520
cgtaggaatt caaggctgca gtgagctatg attgcaacac tgcactccag cctgggcaac   41580
agagtgagac ctggtctcaa aaaacaaaaa aattatatat atataaaaaa ttgtttatat   41640
atacgtatat catatatatg tgtatatata catatatata tacaactgac aaaagtattt   41700
ttcatcttga agactagttt taacagccac atgtatatat ttatgtatgt atatgttaat   41760
atatttgtta atatatgagt atattaacaa atttatagt tatatataaa tatgcatata   41820
tttgcatata cttatatttg ctatattta atatatatgt atatagtata tatatatagg   41880
```

```
tatacacaca cacgtgcgca agtgtgcaca cacactcatg gtgcacacac atgcatgtat    41940
gtcccagggt cccatgttgg atataccagg gccccagaat ctacactttt aacaagtact    42000
ccagctgatt tccataaaga tggcgtctag gtatttgggg accattgtgc aagggaacat    42060
ggtacccttt acctggagat aaagaccaag ggtgaatggg aacaagttcc tggttgtgat    42120
ctcccccatt gccttactgg taatagtcct gaaacagtgt ccctgccccc tcatctggtg    42180
tgcatctggc tcaaagcaaa aatgtagata tattttctct tgctgttttt attaaattct    42240
gtttccttaa gaagctgatg ccagaatcaa cagaagtatt ctactttaca catttaaact    42300
tcttgctaca atccttttcc tcttccctct taacgtattc ccgaatttgg actgaagtga    42360
aactccccag gattatcctc cagtgttttg aattctccag ggaaacattt tggatagcag    42420
gatgagtgtt ctggagtcag gcagattggg tttgagtcct attctatttg ttggtaaatt    42480
ggccaaagtt tattaaggag ggttccagac atcagttttc tcattaataa aatggaggtg    42540
gttatagctt cttgaggttg tgtgagagtt agaaataata tatataaaac actcaggaca    42600 gtagcccta ttaagccctc aacagattta aaaaatacat tttcaaggtc attataggtc    42660
acaaagaagg aagtcatgcc tttgtggaac tattcagcag taaacagcaa aatgcatgtg    42720
catgtgagag atgagggatg agttccttaa gccatgggct ggtgaatatg taagcaaatt    42780
taaataactt gccgacaagc tcctttctcc aaaaatgtat ttccctggca gcaattgttg    42840
ggtccctctc ttcttttcaa tagccagatc tagaataggt ttcctttagt aacttgtttc    42900
cctatttggt tatatatata tatatatata tatatattta aatttacata agcacttatt    42960
tggttcttaa aatgaatagg aaaggaaaaa ccccagaatc tttgtgatct ggttagaggc    43020
tgggtgtata gcacaaccag gctaactctt aaaaaattat gtaggccagg tgtggtggct    43080
caagcctgta atctcagcac tttgggaggc tgaggcgggc agatcacttg aggtaaggag    43140
ttcaagacca gccttgccaa catggtgaaa cgctgtctct actaaaaata caaaaaatt    43200 atccgggtgt ggtggtgcat gcctgtagtc ccagctactt gggaggctga ggcaggagaa    43260
ttgcttgaac ctgggaggcg gaggctgcag tgagctgaga ttatgcctgt ctttggtaaa    43320
aacaaaacaa aacaaaacaa aaaaccacca aaaatttttt tttaattta aaaaggacaa    43380 gaaataaaaa gtcagtccac ttactgatag agaattgtag ttgaaactag tgctttgagg    43440
tacaacaccc ttcattcact tagtattctg ccttcatagc ctgatggcta gctgtccctg    43500
ggtaaatttt gtaacttcta tgaacctcac tttcttcaaa tgcaaagtga ggctaatagt    43560
tctgacttta ctgggctgtt gggagcatta aataaaataa tgtgtatgaa gcacttatac    43620
tttaacttca gtaaatattt gttgaagaat aaataattta gcctgaactt caatatataa    43680
tgtggaataa aaaattgggg gtaaatgaga tgtcagaaaa tgaagtataa atcctgaact    43740
aggaggtaaa ggatggtgtt ttagcctacc caagttaatt tatatgtagc ttttttgttt    43800
ttctttagga accaggctgt ggccaggaac ttttatattc agctcagctt agattttaaa    43860
aacagcatca ttcatttctg ttttccttca aatgcaggtg cacccatcat tatgtctttc    43920
ccacactttt accaagcaga tgagaggttt gtttctgcca tagaaggcat gcacccaaat    43980
caggaagacc atgagacatt tgtggacatt aatcctgtga gtacatactt cctcctggta    44040
aaagagcata tgttttattc tgtctataca ttgttcacca gtttagtcct gagccttctt    44100
taaaaatatc cttactttca tatacatatt caagtgggag aaattcagct cagtgctgat    44160
ggaggcattg tctcatagcc ctgtaattag aaggctgaat tttgtggatt gaatagcaga    44220
aatacgagca aacctgcctt taacaaaaag caacagtgaa aactcagtta ttggaaacta    44280
```

```
ctgatgtacc catataacct ggtcaatctt ctgatgctag ccttggacct caacatatat    44340
ttatttctcc ccttgggaca cagatcgata aggttaaaga tgtccctttg cttcctcact    44400
gccaggaata ttttggttga aatatgaata tgtatattaa cctcagtcac ttttggcaaa    44460
cttctttcta caggttattt gagagtttat tatattatta attgtaaagg tatcagatat    44520
acatagagga gacatacaca cgtgtgtgtg tgtgtgtgtg tgtgtataat acacatttac    44580
tcctgtattc atagacgaga aaaacaaaaa ccatgctaac catgtcttca tttttggaat    44640
ttgaacatta tggaccaata aaaaaaaaaa acaagaacat tcttttagca cagtatttta    44700
tgggtacttc acactcttag ctgcatacat tgcatttgta tctgagaaac cagtgatctt    44760
atgctctggt gaataaaatc gtgtgtggtt ttctcccttt tctcttagcc atcagctgat    44820
cagttccctt ggatcagcca aactgttagc agtgcttgtc accaagggac gaacacagtc    44880
ttataacctt agtgcaaaga tggagctgcc ctaaggatga caagtgctgc agctgtgccc    44940
catggctacg ctaggcgggc cctatactag gatgccactc tctggcagtg accaccaccc    45000
tcttcttagc tctctggaca actgcctgga aatccagacc tgacaggcta tcttttaggc    45060
ctccttcctg ttgatccct tctaaggctg tgctattcag agtggcagca tcctgggagc    45120
ttgttagaaa tggccagtct actgaatcag agcctgcatt ttaacaggat tcccaaggac    45180
ctacattcat actcatgttt gagacacact ggtctatcag ccacctaata caacccatgg    45240
ttctcattct gttctgggga tcactttttac ttgtttccac tctgcctgtc acacatggta    45300
atggtcacct tgtttatgag gactacacag aaatggtgct ctattgaaaa agttgtttgc    45360
agtttaataa atcctaatgt ttccttttca cttctctgat ttgcagttga ctggaataat    45420
cctaaaagca gccaagaggt tccaaatcaa catttatgtc aaaaaattag atgactttgt    45480
gtaagttttg cttctttcta tggaggggac agcagttttg ctccattgcc cgtctggtgg    45540
ggttgatgtc aggaggagta cagcctactt catctaagcc tgctcacccc tgcccttcag    45600
ggatggggca tgatcagcat tttcatgggt gccttggtct tggaatttac ttgttttatt    45660
taatcataca cttacagagt acttcccatg gatcaggtat tgttctcagc accttatgtg    45720
gattcacata taaccttgta ttatccccat tttacagatg aggaaacaga agcagagtgt    45780
ttaggtaact tggctaagcc ttactatcta gtcaactttt atccactcca ctaagccttt    45840
ccctcatgca ccttgactct cttggtgtat tagactgttc ttgtgttgct ataaagaaat    45900
acctggctgg gtacagtggc tcatgcctgt aatcccagca tttgggaggc caaggtgggt    45960
ggatcacaag gtcaggagat caagaccatc ctggccaaca tggtgaaacc tcgtctctac    46020
taaaaataca aaaattagct gggcatggtg gtgggtgcct ataatcccag ctattcggga    46080
ggctgaggca agagaatcgc ttgaaccagg gagtcggagg tcacagtgag ccaagatggt    46140
ggcactgcac tccagtctgg cgacagagca agactgtgtc tcaggaaaaa aaaaaaaagc    46200
gggggggggg agggagggag ggaaaggaaa ggaaatacct gagattggtt aatttataaa    46260
gagatttaat tggcttacag ttctgtaggc tgtacaggaa gcatggtgct ggcatctgct    46320
cagtttctag ggatgcctca gggagctttt gctcatggca gaaggagaag caggaataaa    46380
gcacgtcaca tggggtgagc aggagcaaga gagagaggag gggaggtgcc acacactttt    46440
aaataacaga tctcatgata actcactatc acaaggacag caccaagcga atggtgctaa    46500
accattcatg agaaatccac ccccatgatc cagtcactgc ctaccaagcc ccacctccaa    46560
cactgggggat tacatttcac cctgagattt ggggaacaa gtatccaaac tatatcactc    46620
agagacttga gacagagtct cttcctcttc ctctctctct attcccactg atcccacttg    46680
```

```
gggccagcca tagctctcat ttgtatagtt ataatctctt gagtctagcc ttacttcccc   46740
atgctgcagc ttaatttgga ttccaaagta taatctcctg ctcagacttt tcaatgggaa   46800 tttttttagat atgagaaaat tatgatataa tgttgagtga ataaacagg atgcaaaact   46860 atgcataata tatttatcta taaaacttgg cttgtttacc tcattgaatt tgccagattt   46920
aataccaggt gtcatggctc tttctaagaa gtaggtggtt tacaagaatg catttttgtca   46980 tctgcatatc tatttccgag gcagtataat ttagtagtta agagctggaa tcttagaagc   47040
aaagtggaat tacatttgtg gctccatcac ttacttgtgg tgatcctagg cctctctgag   47100
tcataatttt ctcatctgta aacctgggac agtaatacct actgtaggtg actactctag   47160
gaattgaatg agataatatc ccaaaaacac ccagcacaga gctggcacgt ggtacatgct   47220
cagttggctc ttgttgcaaa gacagtactt cagtggccta gttacaaaac actctgagga   47280
gtgacagttt tgttctgtcg actggagcct tccctgatga ctctaaggag actagtcatc   47340
attttaagga atctgccttc agtatcttgt gttttgataa acgtacagca catggaattg   47400
ctagacagac tggaatctaa cttttggggt acatgtttgc aaagataact aagaaatcag   47460
caaattctgg gtaatttaag aaataagtgt actagaatct tcatataaat gtgtctgtcc   47520
gggaaagtgt gccattgtga tgaggatgtt tctgaaacaa tctcatcctt tgtctttgta   47580
gtgaaacggg agacattaga accatggttt tcccagtgat gtacctcaat gaggtaagtc   47640
ctgagacgga gggagccacg ggtgttttca gactcagaaa aaatccatta tgatgtctac   47700
tgttgtagtt acatgtaagt tatgacagaa gggcaaaaga tttttaaaac ctgttattcc   47760
tcagaaaatt tcacttaaat gttcacatga atctgcctgt gtctgagagc tgatttggag   47820
aaatgatgga aagaaatttt ccttctcaag aacactattt gggcaaaact cccttctggg   47880
gagctgctca cgtaggaaac agaaacaggt aaaaggagcc attggcagac attgttgaag   47940
cagggaaata gctcacactc agatagatgc cagctagccc tttgtctccc ccttctttga   48000
aaccatgctg gtttaagaca cctatgataa attcttttct gaatcacata tcacgtttac   48060
tgtagttata tctcctcagt ttctcctgct tccgcccagt ttgagggaaa aaaaaaaac   48120 gcaggttttt ttcttcaata aattcttgat tggcaaactt ctccttttta ttattttgt   48180 gtttcctaaa aatacttgct gtttgtagaa tattgaataa cagagattag caagaaaaag   48240
aaaaattaaa atcactattc acaaaatctg tgtcagcctg ataatatttt tatttatttt   48300
tactcaatgt gttgtacaat ttttccaat aacaacttta aaaggtaatc taatgttttta   48360 cattttataa aacatgtgct ctttataaaa ttcttagaaa ttttttttaaa aattgattta   48420 aaaagtaaat tactgataag tccctctcta tcagaggcag gtgcagttca gatgtcaact   48480
cctgatattt tctggtcttg atattacata gttgaaatca tacgatagat acaatttat   48540 atctttttc tccatttagc attatattgg tattcacatt tacaaacttt taagggtttg   48600
ttattacaat tctaagatga ggttttatc gtttcatagg aaaaattcaa gcaatattta   48660
ccaatttata ggatctcttt gcaattgctc ctgatcatcc atgttcctgt ttgtgggcag   48720
gggcatgaaa gatctttttg aaaatgcaga agggcccttt tctgccaact tctgttcagt   48780
agtggcatat ttgaagtccc tccaccccca acttctaatt tgcttttttg tgaaagacta   48840
gattaagtcc aggtgtgtgg agtggaacct tgtatttttg ctgcctccta ggaagagcgt   48900
gattattctc ttctctagaa aaataaaata ttagacctgg aagtctggaa gtgacattgg   48960
agactgttgc cacaccacct ttttaccgag gaggaaactc tatccagtta ttggaaaaaa   49020
tgtcttagaa cccaatccac tgactcggtc caatgaaaaa aaatgctttc ttttcttttt   49080
```

```
tttttttttt tgagacaagg tctcactctc accctctaca gtggtgcgat tttggctcac   49140
tgcagcctcg acttcccggg ctcaagtgat cctcccacct ctgccttcca agtagctgga   49200
actacaggtg tgtgccacca tgcccggcta attttttttt tttttcctga gatggagtct   49260
tgctctgttg cccaggctgg agtgcagtgg cccaatctca gctcacggca acctctgcct   49320
cctgggttca agcaattctc gtgcctcggc ctcccaagta gctgggacta caggcgcccg   49380
ccaccacccc tggctaattt ttgtattttt agcagagatg aggtttcacc atgttgaaac   49440
tcatgacctc aagtgatctg cccatctcgg cctcccaaag tgctgggatt acagtcatga   49500
gccaccatgc ccagccccag ctaattttttg tattttttgt agagaggtgg tttcaccaca   49560
ttgctcaggc tggtctcaaa cttttgagct caagcaatcc gcctgccttg gcctcccaaa   49620
gtgctgggat tataggcgtg tgcaactatg ccaggcctcc agtgcaaatt aagcctaaac   49680
taggccagaa ttgttgctca ttatttctat ggaattaagc tcttcagata cctcactcat   49740
tacactaggt ggtaattcct ctgctctgca tacactaagt gttattctag tacatttcct   49800
tctatcagca gtctctggaa ttctagttag cccacaactt tgctgagcac tttctgtaga   49860
gggctgtggt cctgattact atagatgtaa ccaagaaaga aattatactt tccacatacc   49920
atttttgcag tgtttcattt atttattcat ttaatcagcc agcattaatc aagcacctac   49980
tgtgtgctgg gtgctatacc cagtgtgag gtgactgagg ttaagtcttg ccttcaggga   50040
cttcacagcc attgcaagac aaacagttac aatgcagagt gcaaggacaa tgatggaagt   50100
agagagtgag atggaaactt agggaggagg cctttgacta ggcctgaggt agccagaaa   50160 aactttgga aggaagtgat gctgagctgg attttttaagg atgaattgga attatctgac   50220
ataaaacaaa aggtgatact gtctcaatat ttctgaatac attttaccctc cttttttccaa   50280 tctatttaaa gagtaaaaaa aatgtcttca ggagaagaca agatattaat gaataaatgt   50340
cccttctgat tactctgact tataaatgga ttttcagtat gtttggtttg ctaacaggag   50400
gacattccca aattgtatta aacaaaggaa agatatagca aaaaacagtt acacactgga   50460
tgtttagtca tcaagaatac tattttcttg cctctccaga gtgttcacat tgataaagag   50520
acggcgagtc gactgaagtc tatgattaac actactttga tcatcaccaa catacctac    50580 atcatcatgg cgctgggtgt gttctttggt ttggtttta cctggcttgc atgcaaagga   50640
cagggatcca tggatgaggt gagaactggc tgaaggaact tcttccttac tggataactt   50700
tacctgagga attcaactgt acttcactga agggctgtca gctggcttat taggataaat   50760
tctgggattt tatgctgggc atagtgattt cgtgcttatt ttactgctgg accaaatggg   50820
aagcaaagga agtgtgtcaa agaaggtgga gggttagaag gtaccatcta atatttgggg   50880
aatagaatct ctttggatgt atcccctggg agttaacttt atgtctttga aaacaataac   50940
ctgaaagaaa aggaagaata tataacagtt acacatctga tctttggtgt cagactgcct   51000
gagttcaaat cccagttctg ccacttaaca gctatacgac cctagaaact gtgcttcagt   51060
ttcttcatct gtaaaatggg ataataaaag cctcccttat gagttttca tgaggattag    51120 atgatatagt agacttaaag gacttggccc agtgttagca tatagtaaga gctcaataaa   51180
ggtttaagta ttattaaata tgataaaaca gctccaagat tatagagcaa gacagccagg   51240
gtcctgcttg gaaagaatcc ctgatgtatc cgaagatacc tatgatttag gtatcactgc   51300
ataataaatg attggaacat gggtgtagtt actttcctgg aaggctagga taaagagttg   51360
ggttcgcctt tccaagtgac cagcagccca gccaggaacc tgaatacctg caatgagcct   51420
tttctgtaga agcccttctt aaattttctg cagcttcctt ttttttacaa cagtggcctt   51480
```

```
ttttcctcca gtttcctcaa ctaagtgtcc aaggcaaatg tgaagtagaa aataaatacg   51540
tgaaaccatc tgagtaaaat tagctgaatt tccctgactt ccatattctt ccattatttc   51600
tcttatcccc tgccagtcac tttagcctga attagctgtg aggcaaacta ttttgccatt   51660
tctatgtgtg gatcttccag tgtgacttta tgcagtcatt gaaattgtct taagcacaaa   51720
tgaaacctca tggaaatgtt aattactgct cctacaatta accttcctca tatattcaac   51780
aagcaaggaa ttattgagaa ctaataccte tgagcacta ctccttagta ggtttcaaac   51840
caggaaggag gcaagttgaa tagagtctaa gttttataat ccagatcaac acagagaagg   51900
gtactgctct ggtattgagg gtgggagtgg tcagagaagg cctcctggaa aggttaggcc   51960
tgctgaatct tcaagaacaa gcagcagccc aagaggggag gtgagtgaga tgagccacct   52020
tcctataggt ctctcctcct tccatgcccc cactccccac ccaaactttt cacactgggg   52080
agaagtttct gacatgaaca tctaacttgt tttctctctt ctgtgtttca gggaacagcg   52140
gatgaaagag caccccccat tcgaacctaa acattgcctt tgcttggtga agaaactgtg   52200
tgagctgtcc tgacctggac gatgacgtgg ggaaaccctc cacctccttg caggcttgtt   52260
gcctgttgaa agaaggaaaa agacacggcg ctggcaagtg ataggaacat tctggccaga   52320
ggttaaagag caggctgaca tggctggcca ttaagcttta taaaatcatg tgggctctga   52380
aattgttctt ttatgtgtct agcaagtatt taataaaccc ttgtatagta attttgttgt   52440
tgttgggtgc tggtagctcc agaattttgt gaccactatt gtgggtaaaa tgtctctgca   52500
tcacttgtta atgctactgg tctaacttca ttcagtatgc ttcattcacc gaactttgtg   52560
ctcaaaatgc gtatatacca ttttatgttg tattcctcca tttcacttgc aaaacagaag   52620
taaataagag ttcgggaccc agggtaaaat ggtagcttca tccaatatat cattcaaatg   52680
catctgattt ctaaaacata ttacatttta tgctgatctt cagttcataa ttcttccagg   52740
aaaactcagt cttccaactg caataaaata ctgggtagaa tcaaatggga aaggggttgg   52800
gtggggcaat acccatgagt tgatagtgat aagctcctaa ggattttaa cttgtacttt   52860 tgtgaacgaa gagaatgcat aaataatgtt ggtgaggata aagtacagat atttcatgta   52920
gaattaattg ctagttatga tgcttgtgga tagttaactg tttttttttt agtcaaaatg   52980
atcatgctac gaaaagatgc ttctgagaga atgtaatgag taactgattt ttcttcctga   53040
gtcgcccttg ccaaatatgt tactgtatta attaatctaa tattgagtga ttatttgtaa   53100
aattatgaat atgggaaatc catctatcta cagcctaagt tacacataag tttcagaaag   53160
tctgattaga ctaaagagat atttcttctg ggacagccgc cttcttggta attttgaagt   53220 tcttttttaca agttccttcc tcagtttcag ttctttccag tgttttgtag ctcactgtca   53280
ctcactgaat agagaaacgt gtgccctata cttcctgtga caatcatttt gctgacagaa   53340
tgatggatgt ttaaaatatt gcacaaagta ctttaaagaa aggtctgtta ggaccagaag   53400
cagagacacc acttttcaaa ggacttcttg gtttcagcat aacctaagac agggaattgg   53460
gagccatcat atgtcacagt gttcagaatt caagcatatt taagggcatt ttctttgatt   53520
ctcaaagttc agcattcatt ttgaattgag aagcctatac atttagctga caaagtgctt   53580
atagaatttc ttaacaactg aaccattcaa aaggattttt tttgtttaaa actggatttc   53640
aatgtaagca aatgaagaaa aaaatataga tttcatttcc atagcttctt atccctgtat   53700
tgaggtaata aattgttttta ctgacaattt ttccttttc tacactaaaa caatatgtga   53760
tatatttccc ctcttgaaga ggcaattcat taaactctca aattttctat agaatcaaga   53820
tagaaccttt agatactcca actcaccaaa atgtaaaaaa actaacaaaa atatttggtc   53880
```

| | | | | |
|---|---|---|---|---|
| ttcaataatg | ctaaatatct | acattittag | aatttatcaa | catttaacta gataattggg | 53940 |
| catgtcttaa | ttatgcatgt | acttatccat | actaataaaa | ttgacaatgc tagtgcatac | 54000 |
| ttattggttt | agtcctatta | tcaggatata | atcatctgtg | aggaggatat tttaaatact | 54060 |
| gtaaatgata | acagttaatg | atatacacat | ttagactgag | ttgcacactg gcagggagac | 54120 |
| caaaaacatt | acttccatac | ttgtgtcatg | attctttttt | ttttgagaga gtctcactct | 54180 |
| gtcgccaggc | tggagtacag | tggcatgatc | tcggctcact | gcaacctctg cctcccgggt | 54240 |
| tcaagcaatt | ctcctgcctc | agccacccaa | gtagctggga | ctacaggtgc gtgccaccac | 54300 |
| gcccagctaa | attttgtatt | tttagtggag | acggggtttc | accatgttgg ccaggatggt | 54360 |
| ctcaatctcc | tgaccctgcg | atctgccac | ctcagcctcc | caaagtgctg ggattacagg | 54420 |
| cgtaagccac | cgggcctggc | ctgttttatg | attcttaata | gttacttggt ttaaatcaca | 54480 |
| tttgatacta | tccttctgaa | aagtctgaga | cagatctaca | aactacagtc aaaattatag | 54540 |
| attaagagga | atgaatgcac | ctatttggct | ttaagttgaa | gatgaattat ttctcatgct | 54600 |
| cattttcttg | cggcagttat | cttagaaaga | cccccaaagg | ctttgtgatt gtaagcactg | 54660 |
| tcatgatcac | agaatgcaag | cttctggtac | catgatcctc | aacttagaga ggaagaaacc | 54720 |
| aagacagaga | gcttaactca | cttctctcag | ggaaaattag | gagttgagca caggacagga | 54780 |
| aatgggcttt | gccacttta | gctccaggct | tttctaacca | gacttgattt cctcatgttc | 54840 |
| tagaaagatc | actaatggtc | aagtggaaca | agcactacac | gactaacccc tattggggtt | 54900 |
| tttaacttaa | gggaggctaa | ttttaattt | aaactgctcg | agatatgagt tctgcaaaag | 54960 |
| gtggtccgca | tccttggccc | tctggacatt | atcactaaat | tgcttgtgcc tgttaacaag | 55020 |
| aatactgacc | agaatgctct | tcatgtagct | tatacagttg | gttcacttca tgcggttctt | 55080 |
| gacatgttta | tttctaccct | taatgcaatg | aaatgtttca | ttaataaaaa accactttat | 55140 |
| at | | | | | 55142 |

<210> SEQ ID NO 29
<211> LENGTH: 4748
<212> TYPE: DNA
<213> ORGANISM: Homo sapiens

<400> SEQUENCE: 29

| | | | | |
|---|---|---|---|---|
| cctcgcgggg | ttgcggcgag | cccggcccgc | gaacgtcacg | tccctgcgcg ctccctgcac | 60 |
| tctcccgagc | tgcgctaggc | gggcgccacg | gctgcccggc | gaaggaaacc gaaaccgagt | 120 |
| ccgggcccgt | ccctccgcgg | cccatccgc | ccggtgcacc | cggggccgcg ctcgccaggc | 180 |
| cgcggagccc | agagctgcgc | gcacgaaccg | tgcgccggga | gggcgtgggc gtggcgccga | 240 |
| agggtcccgg | gtcttcgacg | cctctgcggc | ggctcctccc | tccttgcagt tggatccctg | 300 |
| gcgggtgcgg | cccggcccgg | cccgtgagcg | gcgcacagaa | tgggccgatg ctgcttctac | 360 |
| acggcgggga | cgttgtccct | gctcctgctg | gtgaccagcg | tcacgctgct ggtggcccgg | 420 |
| gtcttccaga | aggctgtaga | ccagagtatc | gagaagaaaa | ttgtgttaag gaatggtact | 480 |
| gaggcatttg | actcctggga | gaagcccct | ctgcctgtgt | atactcagtt ctatttcttc | 540 |
| aatgtcacca | atccagagga | gatcctcaga | ggggagaccc | ctcgggtgga agaagtgggg | 600 |
| ccatacacct | acagggaact | cagaaacaaa | gcaaatattc | aatttggaga taatggaaca | 660 |
| acaatatctg | ctgttagcaa | caaggcctat | gttttgaac | gagaccaatc tgttggagac | 720 |
| cctaaaattg | acttaattag | aacattaaat | attcctgtat | tgactgtcat agagtggtcc | 780 |
| caggtgcact | tcctcaggga | gatcatcgag | gccatgttga | agcctatca gcagaagctc | 840 |

```
tttgtgactc acacagttga cgaattgctc tggggctaca aagatgaaat cttgtccctt     900
atccatgttt tcaggcccga tatctctccc tattttggcc tattctatga gaaaaatggg     960
actaatgatg gagactatgt ttttctaact ggagaagaca gttaccttaa ctttacaaaa    1020
attgtggaat ggaatgggaa aacgtcactt gactggtgga taacagacaa gtgcaatatg    1080
attaatggaa cagatggaga ttcttttcac ccactaataa ccaaagatga ggtccttat     1140
gtcttcccat ctgacttttg caggtcagtg tatattactt tcagtgacta tgagagtgta    1200
cagggactgc ctgcctttcg gtataaagtt cctgcagaaa tattagccaa tacgtcagac    1260
aatgccggct tctgtatacc tgagggaaac tgcctgggct caggagttct gaatgtcagc    1320
atctgcaaga atggtgcacc catcattatg tctttcccac acttttacca agcagatgag    1380
aggtttgttt ctgccataga aggcatgcac ccaaatcagg aagaccatga gacatttgtg    1440
gacattaatc ctttgactgg aataatccta aaagcagcca agaggttcca aatcaacatt    1500
tatgtcaaaa aattagatga ctttgttgaa cgggagacat tagaaccat ggttttccca     1560
gtgatgtacc tcaatgagag tgttcacatt gataaagaga cggcgagtcg actgaagtct    1620
atgattaaca ctactttgat catcaccaac ataccctaca tcatcatggc gctgggtgtg    1680
ttctttggtt tggttttac ctggcttgca tgcaaaggac agggatccat ggatgaggga    1740
acagcggatg aaagagcacc cctcattcga acctaaacat tgcctttgct tggtgaagaa    1800
actgtgtgag ctgtcctgac ctggacgatg acgtggggaa accctccacc tccttgcagg    1860
cttgttgcct gttgaaagaa ggaaaaagac acggcgctgg caagtgatag gaacattctg    1920
gccagaggtt aaagagcagg ctgacatggc tggccattaa gctttataaa atcatgtggg    1980
ctctgaaatt gttcttttat gtgtctagca agtatttaat aaacccttgt atagtaattt    2040
tgttgttgtt gggtgctggt agctccagaa ttttgtgacc actattgtgg gtaaaatgtc    2100
tctgcatcac ttgttaatgc tactggtcta acttcattca gtatgcttca ttcaccgaac    2160
tttgtgctca aaatgcgtat ataccatttt atgttgtatt cctccatttc acttgcaaaa    2220
cagaagtaaa taagagttcg ggacccaggg taaaatggta gcttcatcca atatatcatt    2280
caaatgcatc tgatttctaa aacatattac atttttatgct gatcttcagt tcataattct    2340
tccaggaaaa ctcagtcttc caactgcaat aaaatactgg gtagaatcaa atgggaaagg    2400
ggttgggtgg ggcaataccc atgagttgat agtgataagc tcctaaggat ttttaacttg    2460
tactttgtg aacgaagaga atgcataaat aatgttggtg aggataaagt acagatattt    2520
catgtagaat taattgctag ttatgatgct tgtggatagt taactgtttt tttttagtc     2580
aaaatgatca tgctacgaaa agatgcttct gagagaatgt aatgagtaac tgattttct     2640
tcctgagtcg cccttgccaa atatgttact gtattaatta atctaatatt gagtgattat    2700
ttgtaaaatt atgaatatgg gaaatccatc tatctacagc ctaagttaca cataagtttc    2760
agaaagtctg attagactaa agagatattt cttctgggac agccgccttc ttggtaattt    2820
tgaagttctt tttacaagtt ccttcctcag tttcagttct ttccagtgtt ttgtagctca    2880
ctgtcactca ctgaatagag aaacgtgtgc cctatacttc ctgtgacaat cattttgctg    2940
acagaatgat ggatgtttaa aatattgcac aaagtacttt aaagaaaggt ctgttaggac    3000
cagaagcaga gacaccactt ttcaaaggac ttccttggttt cagcataacc taagacaggg    3060
aattgggagc catcatatgt cacagtgttc agaattcaag catatttaag ggcatttct     3120
ttgattctca aagttcagca ttcattttga attgagaagc ctatacattt agctgacaaa    3180
gtgcttatag aatttcttaa caactgaacc attcaaaagg attttttttg tttaaaactg    3240
```

```
gatttcaatg taagcaaatg aagaaaaaaa tatagatttc atttccatag cttcttatcc    3300
ctgtattgag gtaataaatt gttttactga caattttttcc ttttttctaca ctaaaacaat   3360 atgtgatata tttcccctct tgaagaggca attcattaaa ctctcaaatt ttctatagaa    3420
tcaagataga acctttagat actccaactc accaaaatgt aaaaaaacta acaaaaatat    3480
ttggtcttca ataatgctaa atatctacat ttttagaatt tatcaacatt taactagata    3540
attgggcatg tcttaattat gcatgtactt atccatacta ataaaattga caatgctagt    3600
gcatacttat tggtttagtc ctattatcag gatataatca tctgtgagga ggatatttta    3660
aatactgtaa atgataacag ttaatgatat acacatttag actgagttgc acactggcag    3720
ggagaccaaa aacattactt ccatacttgt gtcatgattc ttttttttttt gagagagtct    3780 cactctgtcg ccaggctgga gtacagtggc atgatctcgg ctcactgcaa cctctgcctc    3840
ccgggttcaa gcaattctcc tgcctcagcc acccaagtag ctgggactac aggtgcgtgc    3900
caccacgccc agctaaattt tgtattttta gtggagacgg ggtttcacca tgttggccag    3960
gatggtctca atctcctgac cctgcgatct gcccacctca gcctcccaaa gtgctgggat    4020
tacaggcgta agccaccggg cctggcctgt tttatgattc ttaatagtta cttggtttaa    4080
atcacatttg atactatcct tctgaaaagt ctgagacaga tctacaaact acagtcaaaa    4140
ttatagatta agaggaatga atgcacctat ttggctttaa gttgaagatg aattatttct    4200
catgctcatt ttcttgcggc agttatctta gaaagacccc caaaggcttt gtgattgtaa    4260
gcactgtcat gatcacagaa tgcaagcttc tggtaccatg atcctcaact tagagaggaa    4320
gaaaccaaga cagagagctt aactcacttc tctcagggaa aattaggagt tgagcacagg    4380
acaggaaatg ggctttgcca cttttagctc caggctttc taaccagact tgatttcctc    4440
atgttctaga aagatcacta atggtcaagt ggaacaagca ctacacgact aaccccctatt   4500 ggggttttta acttaaggga ggctaatttt taatttaaac tgctcgagat atgagttctg    4560
caaaaggtgg tccgcatcct tggccctctg gacattatca ctaaattgct tgtgcctgtt    4620
aacaagaata ctgaccagaa tgctcttcat gtagcttata cagttggttc acttcatgcg    4680
gttcttgaca tgtttatttc taccccttaat gcaatgaaat gtttcattaa taaaaaacca    4740
ctttatat                                                            4748
```

<210> SEQ ID NO 30
<211> LENGTH: 478
<212> TYPE: PRT
<213> ORGANISM: Homo sapiens

<400> SEQUENCE: 30

```
Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
```

```
                100             105             110
Ser Asn Lys Ala Tyr Val Phe Glu Arg Asp Gln Ser Val Gly Asp Pro
            115             120             125

Lys Ile Asp Leu Ile Arg Thr Leu Asn Ile Pro Val Leu Thr Val Ile
130             135             140

Glu Trp Ser Gln Val His Phe Leu Arg Glu Ile Ile Glu Ala Met Leu
145             150             155             160

Lys Ala Tyr Gln Gln Lys Leu Phe Val Thr His Thr Val Asp Glu Leu
            165             170             175

Leu Trp Gly Tyr Lys Asp Glu Ile Leu Ser Leu Ile His Val Phe Arg
            180             185             190

Pro Asp Ile Ser Pro Tyr Phe Gly Leu Phe Tyr Glu Lys Asn Gly Thr
            195             200             205

Asn Asp Gly Asp Tyr Val Phe Leu Thr Gly Glu Asp Ser Tyr Leu Asn
            210             215             220

Phe Thr Lys Ile Val Glu Trp Asn Gly Lys Thr Ser Leu Asp Trp Trp
225             230             235             240

Ile Thr Asp Lys Cys Asn Met Ile Asn Gly Thr Asp Gly Asp Ser Phe
            245             250             255

His Pro Leu Ile Thr Lys Asp Glu Val Leu Tyr Val Phe Pro Ser Asp
            260             265             270

Phe Cys Arg Ser Val Tyr Ile Thr Phe Ser Asp Tyr Glu Ser Val Gln
            275             280             285

Gly Leu Pro Ala Phe Arg Tyr Lys Val Pro Ala Glu Ile Leu Ala Asn
            290             295             300

Thr Ser Asp Asn Ala Gly Phe Cys Ile Pro Glu Gly Asn Cys Leu Gly
305             310             315             320

Ser Gly Val Leu Asn Val Ser Ile Cys Lys Asn Gly Ala Pro Ile Ile
            325             330             335

Met Ser Phe Pro His Phe Tyr Gln Ala Asp Glu Arg Phe Val Ser Ala
            340             345             350

Ile Glu Gly Met His Pro Asn Gln Glu Asp His Glu Thr Phe Val Asp
            355             360             365

Ile Asn Pro Leu Thr Gly Ile Ile Leu Lys Ala Ala Lys Arg Phe Gln
            370             375             380

Ile Asn Ile Tyr Val Lys Lys Leu Asp Asp Phe Val Glu Thr Gly Asp
385             390             395             400

Ile Arg Thr Met Val Phe Pro Val Met Tyr Leu Asn Glu Ser Val His
            405             410             415

Ile Asp Lys Glu Thr Ala Ser Arg Leu Lys Ser Met Ile Asn Thr Thr
            420             425             430

Leu Ile Ile Thr Asn Ile Pro Tyr Ile Ile Met Ala Leu Gly Val Phe
            435             440             445

Phe Gly Leu Val Phe Thr Trp Leu Ala Cys Lys Gly Gln Gly Ser Met
            450             455             460

Asp Glu Gly Thr Ala Asp Glu Arg Ala Pro Leu Ile Arg Thr
465             470             475
```

MEANS AND METHODS FOR DIAGNOSING AND/OR TREATING A SUBJECT AT RISK OF DEVELOPING HEART FAILURE

The present invention in general relates to the field of medicine, more specifically the field of cardiology. The invention in particular relates to means and methods for diagnosing and/or treating subjects at risk of developing heart failure.

It is generally known that chronic cardiac loading, as occurs during long-standing hypertension, valvular disease or other chronic disorders like diabetes, induces cardiac hypertrophy, which is one of the most important risk factors for heart failure. Congestive heart failure (HF) is a common but severe and complex clinical syndrome, especially among elderly people, characterized by a diminished cardiac contractile function and decreased exercise tolerance. Symptoms of heart failure include, amongst others, pulmonary and peripheral edema, fatigue and/or dyspnea. Severe heart failure may also lead to reduced function in other organs because these are not receiving enough blood.

Not all hypertrophied hearts, however, will ultimately fail. Thus, while an important number of patients progress to developing life-threatening complications, others may remain stable for prolonged periods. Until now, the molecular changes that precede and herald this transition from hypertrophy towards heart failure are incompletely understood.

As early identification of patients at risk for developing hypertensive end organ damage, such as heart failure, may prevent rapid progression, it would be preferable to be able to identify (diagnose) those patients in which heart failure is likely to occur before it actually does so. Early diagnosed patients may thus be treated in order to prevent the onset of heart failure. In addition, it would be preferable to be able to identify those patients suffering from heart failure who are at risk for developing severe complications.

Current methods can reliably exclude the actual presence of heart failure, but cannot reliably prove the existence of heart failure, nor can these methods predict the outcome of established heart failure, or predict the occurrence of heart failure.

A need therefore exists for simple and reliable methods for predicting the likelihood of onset of heart failure and/or for predicting the outcome of already established heart failure. In addition, the development of means and methods for treating patients who are at risk of developing heart failure, before heart failure and/or its complications occur, would be of great clinical importance.

The object of the present invention is to provide diagnostic methods by which patients can be identified who are at particular risk of developing heart failure, and/or who are at particular risk to develop complications of heart failure. It is a further object of the present invention to provide means and methods for treating patients who are at risk of developing heart failure, and/or who are at risk for developing complications of heart failure.

This objective is achieved by the invention by providing a method for diagnosing a subject at risk of developing heart failure, comprising the steps of:
  (a) determining the level of one or more biological markers in a biological sample of said subject;
  (b) comparing the level of said biological marker(s) to a standard level of the same biological marker(s), and
  (c) determining whether the level of the biological marker(s) is indicative of a risk for developing heart failure,
wherein the biological marker is lysosomal integral membrane protein-2 (LIMP-2) and/or Krüppel-like transcription factor 15 (KLF15).

In the research that led to the present invention, a number of genes have been identified that are involved in the development of heart failure. The identified genes have been listed in Table 2. It has furthermore been demonstrated that specific polypeptides encoded by said genes are indeed mechanistically linked to heart failure. It has in particular been demonstrated that specific proteins encoded by the genes from table 2 are involved in the molecular mechanisms that are responsible for the transition from cardiac hypertrophy towards heart failure, and thus can be used as a biological marker for identifying patients at risk of developing heart failure. In addition, these proteins, and/or the genes encoding said proteins, and/or polypeptide and/or polynucleotide fragments or variants of said proteins and/or genes can be used as a target for treating those patients at risk.

According to the present invention, it has in particular been demonstrated that specific intercalated disc components, in particular lysosomal integral membrane protein-2 (LIMP-2) and Krüppel-like transcription factor 15 (KLF15) are involved in the molecular mechanisms that predict the transition from cardiac hypertrophy towards heart failure, and can suitably be used as biological markers (biomarkers) for the identification of individuals who are at risk of developing heart failure.

According to the present invention, it has thus been found that subjects at risk for developing heart failure, can be identified by determining the level of one or more of the identified biological markers in a biological sample of said subject and comparing the level of said marker to a standard level. Said standard level is derived from healthy subjects, i.e. the standard level is the level of said biological marker in said biological sample of healthy persons, i.e. persons free from cardiac disease. If the level of the biological marker tested is altered, e.g. elevated or reduced (depending on the specific biological-marker concerned) compared to said standard level, the subject is at risk for developing HF and/or for developing severe complications of heart failure.

An early diagnosis of heart failure, preferably before clinical symptoms occur, is essential for e.g. successfully addressing underlying diseases, and/or preventing further myocardial dysfunction and clinical deterioration by for example treatment of the diagnosed patients.

In the research that led to the present invention, the gene expression profile of a large number of genes from hearts that were hypertrophied due to high blood pressure, but appeared well functional and compensated by traditional techniques (echocardiography), however, later proved to develop heart failure, was investigated. This expression profile was compared to the gene expression profile obtained from hearts that that were also hypertrophied due to high blood pressure and appeared equally well functional and compensated by traditional techniques (echocardiography), but later proved NOT to develop heart failure and remained stable. This way, genes were identified that predicted the occurrence of later developing heart failure, which, according to the present invention, have been shown to be novel and crucial modulators of hypertrophy and the transition towards heart failure. These genes have been listed in Table 2. Subsequently, specific preferred biological markers, in particular specific intercalated disc related biological markers were identified. The intercalated disc (ID) forms the connection between cardiac myocytes making up the cardiac fibers in the heart. The intercalated disc thus is a specialized cell-cell junction providing mechanical and electrical coupling between the cells and supporting synchronized contraction of cardiac tissue.

According to the present invention it has thus been demonstrated that increased cardiac expression of LIMP-2, as compared to standard levels of expression, identifies those hypertrophied hearts that are prone to progress to overt heart failure. Thus, while cardiac development is normal in LIMP-2 null mice (Gamp et al., 2003), hypertension induced dilated cardiomyopathy in these mice. It was shown that LIMP-2 binds to the vital cardiac adherens junction protein N-cadherin and is essential to secure proper interactions between N-cadherin and β-catenin. It has further been found that expression of LIMP-2 is increased in hypertrophied rat hearts that are on the brink to progress to heart failure, thus suggesting that increased LIMP-2 expression by cardiac myocytes heralds their inability to normalize mechanical forces. As such, increased LIMP-2 expression may be seen as a desperate attempt of the myocyte to respond to worsening loading and be indicative of imminent failure. It has moreover been shown that LIMP-2 expression is significantly increased in patients with clinically severe pressure loading. By determining the level of LIMP-2 protein and/or the level of expression of the gene coding for LIMP-2 in hypertensive subjects, and comparing said level(s) with a standard level, and subsequently determining whether the level is indicative of a risk for developing heart failure, it thus is possible to identify in a very early stage the myocardium that is about to succumb to the pressure. In particular, an increased level of LIMP-2 protein and/or an increased level of LIMP-2 gene expression as compared to a standard level is indicative of a risk for developing heart failure and/or heart-failure relates complications.

In the research that led to the present invention it has further been shown that the gene coding for Krüppel Like Factor 15 (KLF15) characterised hypertrophied hearts that quickly progressed to heart failure. This was confirmed by real-time PCR, which showed that KLF15 was down-regulated in compensated LVH, but that KLF-15 was significantly further suppressed in the hypertrophied hearts that quickly progressed to failure. It was further shown that KLF15 has a role in cardiac myocytes as a suppressor of cardiac hypertrophy. Determining the level of the KLF15 protein and/or the level of expression of the gene coding for KLF15 in hypertensive subjects, and comparing said levels to standard levels thus also is useful for identifying in a very early stage those patients that are likely to develop heart failure. In the case of KLF15, a decreased level of KLF15 protein and/or decreased KLF15 gene expression in a biological sample, as compared to standard levels, is indicative for the development of heart failure.

The present invention relates both to in vivo methods, i.e. methods wherein the level of the biological marker is determined in a biological sample in vivo and to in vitro methods.

In a preferred embodiment of the invention, the level of the biological marker is determined in vitro in a biological sample obtained from an individual. For in vitro determining the level of the biological markers of the present invention, any suitable biological sample of any bodily fluid that may comprise a biological marker identified by this research may be used. Preferably, the biological sample is selected from the group consisting of blood, plasma, serum, cardiac tissue. More preferably, the biological sample is a peripheral blood sample, or a plasma or serum sample derived from peripheral blood. Peripheral blood samples can e.g. easily be taken from the patients and do not need complex invasive procedures such as catheterization. The biological sample may be processed according to well-known techniques to prepare the sample for testing.

For measuring the level of the biological markers of the invention use can be made of conventional methods known in the art.

When the biological marker is a protein and/or a fragment and/or a variant thereof, several conventional methods for determining the level of a specific protein, and/or fragments and/or variants thereof, which are well-known to the skilled person, may be used. The level of the marker may for example be measured by using immunological assays, such as enzyme-linked immunosorbent assays (ELISA), thus providing a simple, reproducible and reliable method. Antibodies for use in such assays are available, and additional (polyclonal and monoclonal) antibodies may be developed using well-known standard techniques for developing antibodies. Other methods for measuring the level of the biological protein markers may furthermore include (immuno)histochemistry, Western blotting, flow-cytometry, RIA, competition assays, etc. and any combinations thereof. In vivo, the level of for example non-secreted proteins can be determined by labeling and tagging specific antibodies against one of the proteins of interest. This allows visualization of the amount of protein in the heart by so called 'molecular imaging' techniques.

When the biological marker is a gene, and/or a polynucleotide fragment and/or variant thereof, e.g. DNA, cDNA, RNA, mRNA etc., such as a gene coding for a specific protein, or mRNA that is transcribed, the biological marker can be measured in e.g. cardiac biopsies, by e.g. well-known molecular biological assays, such as in situ hybridization techniques using probes directed to the specific polynucleotides. Other nucleic-acid based assays which may be used according to the invention include RT-PCR, nucleic acid based ELISA, Northern blotting etc, and any combinations thereof.

In order to enhance the specificity and/or sensitivity of the diagnostic method, the method of the invention may include the detection of the level of one or more other (biological) markers, i.e. the detection of the biological markers of the present invention may suitably be combined with the detection of other markers which are indicative for the development of heart failure.

The present invention further relates to kits for performing the diagnostic methods as described above. The invention in particular relates to such diagnostic kits for identifying a subject at risk of developing heart failure, comprising means for receiving one or more biological samples of said subject, and means for determining the level of the biological marker(s) in said biological sample of said subject. Thus a kit is provided which can be used as a reliable and easy diagnostic tool. The means for receiving the biological sample may for example comprise a well of a standard microtiter plate. The means for determining the level of an intercalated disc related biological marker in said biological sample of said subject may for example comprise one or more specific antibodies, polynucleotide probes, primers etc. suitable for detecting the biological marker(s), identified according to the present invention. The kits may further also comprise calibration means and instruction for use.

The invention also relates to the use of the biological markers of the present invention and/or fragments and/or functional variants thereof in a screening method for identifying compounds for the prevention and/or treatment of heart failure. In a particular embodiment, the method for identifying a compound for prevention and/or treatment of heart failure comprises:

(a) contacting one or more compounds with a polypeptide encoded by a polynucleotide listed in table 2, preferably KLF15 and/or LIMP-2, and/or fragments, and/or variants thereof;
(b) determining the binding affinity of the compound to said polypeptide;
(c) contacting a population of mammalian cells with the compound that exhibits a binding affinity of at least 10 micromolar; and
(d) identifying the compound that is capable of prevention and/or treatment of heart failure.

The polypeptides to be tested in the screening method of the present invention may be tested in vitro, e.g. free in solution, affixed to a solid support, borne on a cell surface, or located intracellularly, or in vivo.

To perform the methods it is feasible to immobilize either the polypeptide of the present invention or the compound to facilitate separation of complexes from uncomplexed forms of the polypeptide, as well as to accommodate automation of the assay. Interaction (e.g., binding of) of the polypeptide of the present invention with a compound can be accomplished in any vessel suitable for containing the reactants. Examples of such vessels include microtiter plates, test tubes, and microcentrifuge tubes.

The binding affinity of the compound with the polypeptide can e.g. be measured by methods known in the art, such as using surface plasma resonance biosensors (Biacore), by saturation binding analysis with a labeled compound (e.g. Scatchard and Lindmo analysis), via displacement reactions, by differential UV spectrophotometer, fluorescence polarisation assay, Fluorometric Imaging Plate Reader (FLIPR®) system, Fluorescence resonance energy transfer, and Bioluminescence resonance energy transfer. The binding affinity of compounds can also be expressed in a dissociation constant (Kd) or as IC50 or EC50. The IC50 represents the concentration of a compound that is required for 50% inhibition of binding of another ligand to the polypeptide. The EC50 represents the concentration required for obtaining 50% of the maximum effect in vitro. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, IC50 and EC50 values, i.e. in the range of 100 nM to 1 pM; a moderate to low affinity binding relates to a high Kd, IC50 and EC50 values, i.e. in the micromolar range.

The present invention also relates to the use of the genes and/or proteins listed in table 2, preferably of the KLF15 and/or LIMP-2 gene and/or protein, for the preparation of a medicament for a prophylactic and/or therapeutic medicament for the prevention and/or treatment of heart failure.

Preferably, the present invention relates to the use of a modulator of the genes and/or proteins listed in table 2, preferably of the KLF15 and/or LIMP-2 gene and/or protein, for the preparation of a prophylactic and/or therapeutic medicament for the prevention and/or treatment of heart failure.

In the present application a modulator may be any compound that stimulates the expression of and/or increases the level of one or more of the biological markers which are found to be reduced according to the invention (e.g. an agonist), or any compound that suppresses the expression and/or reduces the level of one or more of the biological markers which are found to be increased according to the invention (e.g. an antagonist).

The medicament may be a protein-based molecule, such as for example an antibody directed against the protein marker, and/or fragments and/or variants thereof. The present invention also includes chimeric, single chain and humanized antibodies, as well as Fab fragments and the products of a Fab expression library and Fv fragments and the products of a Fv expression library.

Alternatively, the medicament may be a nucleic-acid based molecule. The down-regulation of a gene can for example be achieved at the translational or transcriptional level using e.g. antisense nucleic acids. Antisense nucleic acids are nucleic acids capable of specifically hybridizing with all or a part of a nucleic acid encoding a protein and/or the corresponding mRNA. The preparation of antisense nucleic acids, DNA encoding antisense RNAs is known in the art. The medicament may also comprise small interfering (hairpin) RNA (siRNA). SiRNAs mediate the post-translational process of gene silencing by double stranded DNA (dsDNA) that is homologous in sequence to the silenced RNA. The preparation of siRNAs is known in the art. Similarly, the up-regulation of a gene (or over-expression) may be achieved by several methods that are known in the art.

In a preferred embodiment of the present invention, the modulator is an inhibitor of TGFβ. According to the present invention, it has been shown that suppression of KLF-15 is a crucial step in the development of failure prone forms of hypertrophy and that TGFβ strongly suppresses KLF-15. Inhibitors of TGFβ, which are currently being developed in different fields, thus may suitably be used for the development of a prophylactic and/or therapeutic medicament for the prevention and/or treatment of heart failure. Examples of suitable inhibitors of TGFβ which can be used according to the invention are TGFβ receptor inhibitors as made by Scios Inc., Los Angeles, U.S.A., who indicate on their website (http://www.sciosinc.com/scios/tgf): "Scios has developed novel and potent small molecule inhibitors designed to inhibit the action of TGF-beta at its receptor. These small molecules have been shown to be effective in reducing scar formation (fibrosis) when given orally to animals. Scios expects to advance two lead molecules, representing different chemical classes, into preclinical development that could potentially be used to treat disease conditions in patients with significant unmet medical needs."

The present invention further relates to the use of the proteins identified according to the invention for generating diagnostic means for use in (molecular) imaging of one or more of the identified proteins to assess the level of the protein and thus identify a subject at risk of developing heart failure. The diagnostic means may for example comprise labeled antibodies directed against the biological protein markers.

The present invention is further illustrated by the following Figures and Examples.

FIGURES

FIG. 1: Increased expression of LIMP-2 in Ren-2 rats. (a) A left ventricular cardiac biopsy was taken at age 10 weeks, when Ren-2 rats exhibit comparable cardiac hypertrophy and fractional shortening cannot distinguish rats that will progress to heart failure or stay compensated. Between 15 and 18 weeks of age, part of the Ren-2 rats developed heart failure and the remainder stayed compensated until sacrifice at 21 weeks of age. *, $P<5e^{-6}$. (b) LIMP-2 mRNA was found by microarray analysis in 10 weeks-old hypertrophic Ren-2 rats to be specifically overexpressed in failure-prone rats (HF-prone LVH, n=4), as compared to the hypertrophied LVs that remained compensated (comp LVH, n=6) and to controls (n=4). (c) LIMP-2 protein was up-regulated in end-stage failing Ren-2 rats (HF, n=9), as compared to compensated Ren-2 rats (comp, n=6). Both failing and compensated Ren-2 rats had significantly-elevated levels of LIMP-2 protein as compared to control rats (n=6). *, P<0.05 versus control; **, P<0.01 versus control; $, P<0.05 versus comp; Mwm, molecular weight marker; au, arbitrary units.

FIG. 2 AngII-treated LIMP-2 KO (KO Ang) mice have dilated cardiomyopathy. (a) WT Ang mice (n=14) significantly increased their LV weight, while KO Ang (n=14) mice did not (*, P<0.0 versus WT (n=8) and KO Ang). In KO Ang mice, individual myocytes failed to increase their volume (WT and KO, n=4; WT Ang and KO Ang, n=5; myocyte area (au): 264±42, versus 308±14 in WT Ang; *, P<0.01). Bars represent 50 μm. (b) LIMP-2 KO (n=3) and WT (n=4) mice showed comparable blood pressure responses to AngII. (c) AngII-treated WTs (n=8) and KOs (n=8) showed comparable increases in BNP and ANF mRNA expression (*, P<0.05 versus baseline (n=4)), while aska mRNA expression was induced to a significantly lesser extend in KO Ang mice, consistent with their reduced myocyte volume (*, P<0.05 versus KO (n=4); $, P<0.05 versus WT Ang). (d) Baseline echocardiographic parameters were similar for WT (n=10) and KO (n=11) mice (day 0). After 14 and 28 days of AngII, wild-type LV walls were significantly hypertrophied, while knockouts did not show hypertrophy and were even dilated (*, P<0.005 versus baseline and versus KO Ang; $, P<0.005 versus baseline and vs WT Ang). (e) Beta-adrenergic response to dobutamin was decreased in KO Ang mice (WT and KO, n=4; WT Ang, n=14; KO Ang, n=9; *, P<0.005). LVW/BW, LV weight corrected for body weight.

Figure 3:
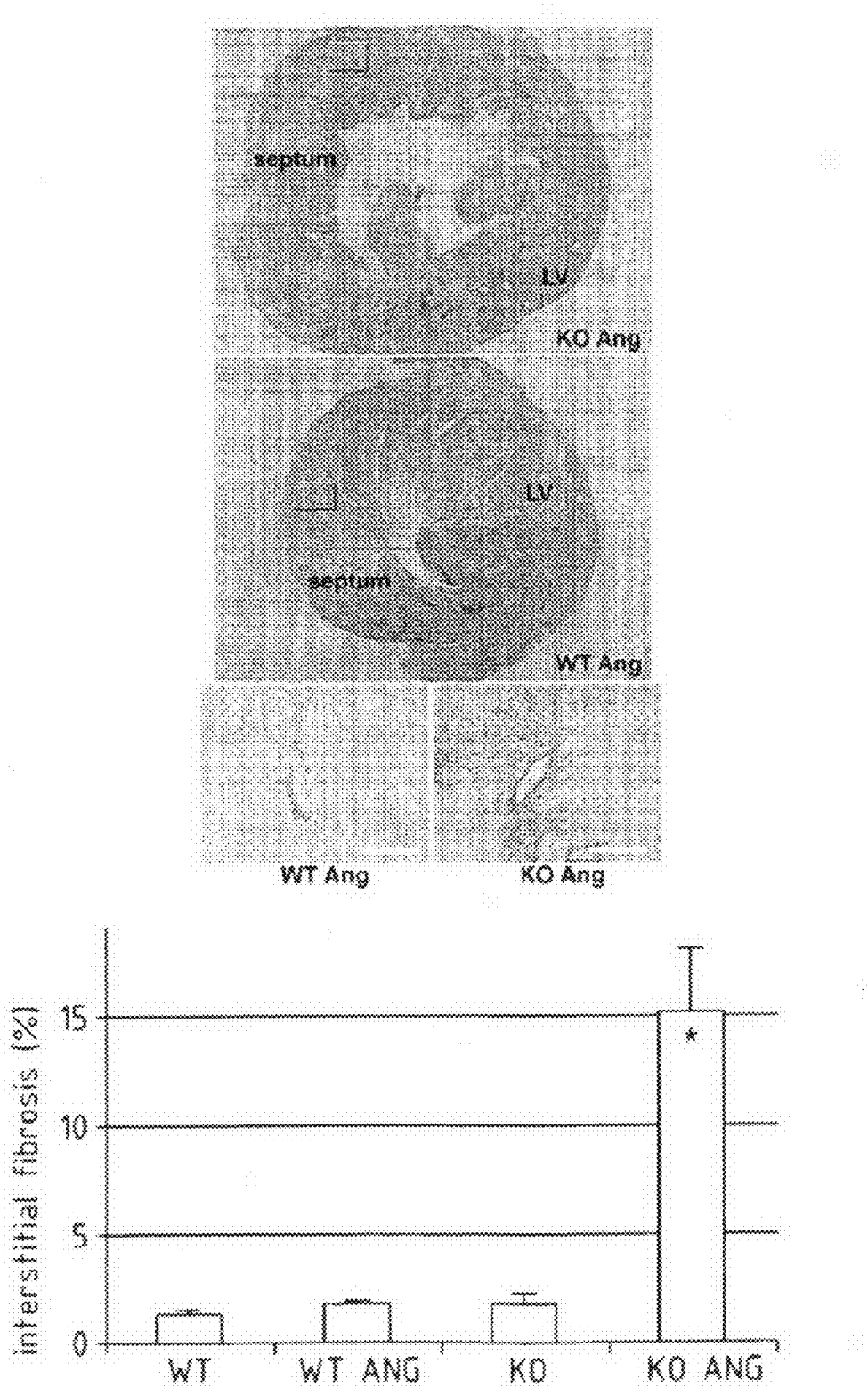

FIG. 3 AngII-treated LIMP-2 KO mice have massive interstitial fibrosis. Sirius red staining of LVs of AngII-treated LIMP-2 knockout (n=4) and wild-type (n=5) mice shows marked interstitial fibrosis in knockout mice (*, P<0.02 versus WT Ang and KO baseline), while both knockout and wild-type mice treated with AngII show similar degree of perivascular fibrosis. Bars represent 250 μm.

Figure 4:
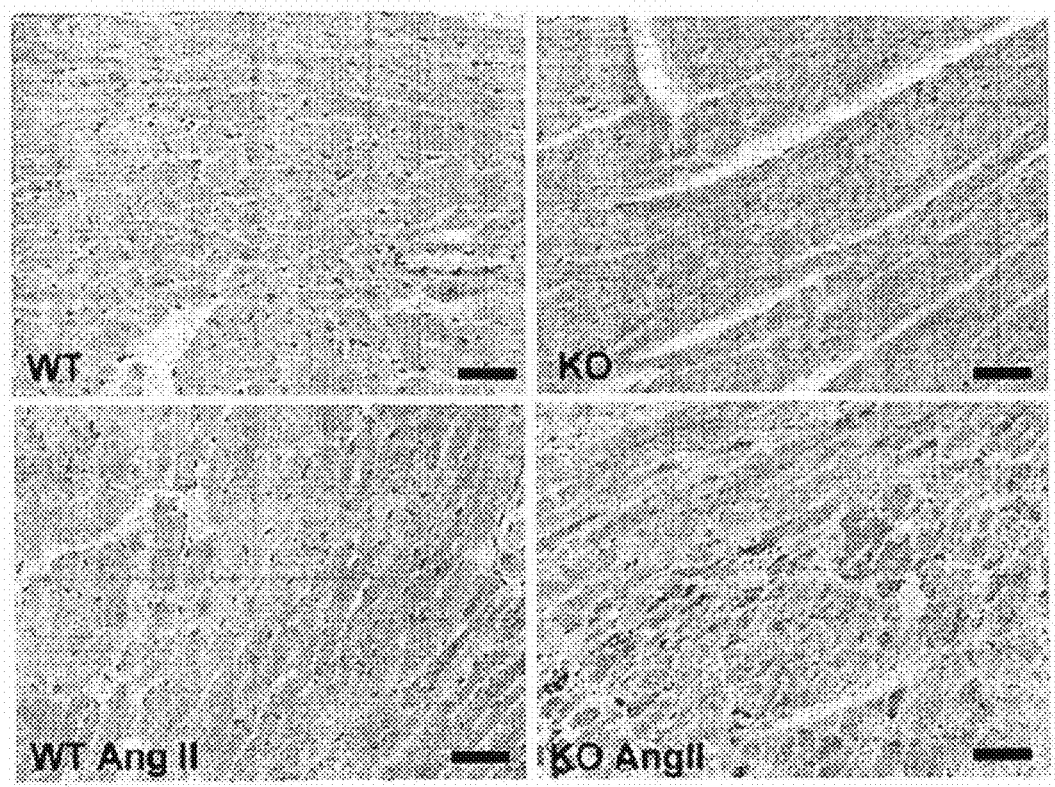

FIG. 4 AngII-treated LIMP-2 KO mice show myocyte disarray. Desmin-stained cardiac myocytes of AngII-treated LIMP-2 KO mice show disarray and have a disturbed internal structure, as shown by the higher and more capricious desmin-expression in these mice. Bars represent 250 μm.

Figure 5A:
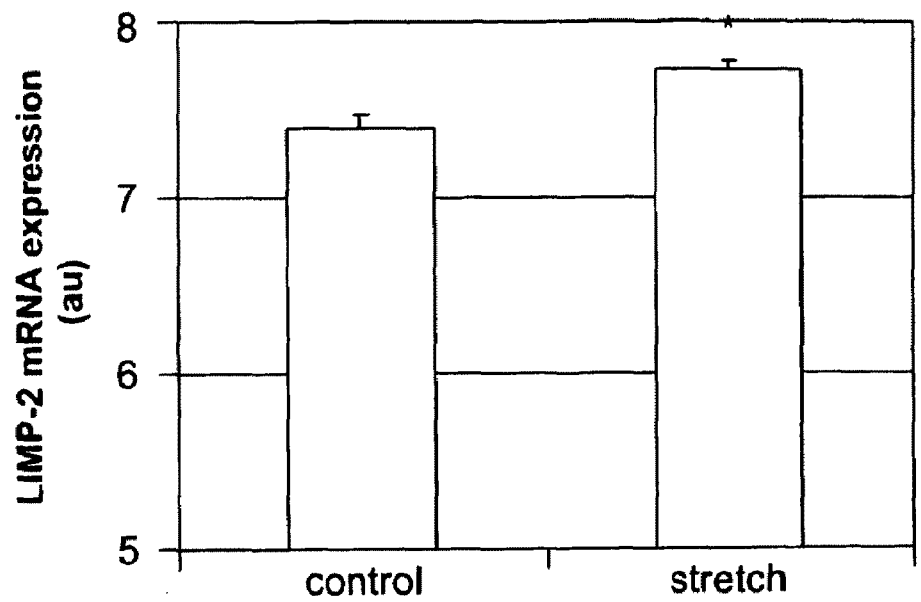
Figure 5B:
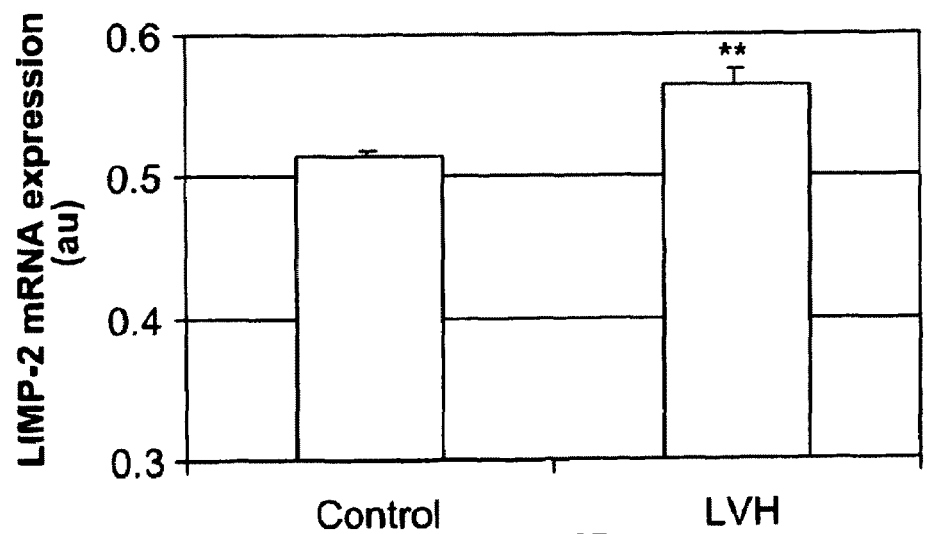

FIG. 5 LIMP-2 expression is up-regulated in other forms of cardiac stress. (a) In neonatal rat cardiac myocytes, 6 hours stretch elevated LIMP-2 mRNA expression (n=4 per group). LIMP-2 mRNA was also up-regulated in hypertrophic myocardium (b) from rats that had undergone exercise training for 10 weeks (5 days per week, n=6) as compared to non-hypertrophic control rats (n=7) and (c) from patients suffering from aortic stenosis (LVH, n=20) as compared to non-hypertrophic control patients (n=7). *, P<0.05 versus control; **, P<0.01 versus control; LVH; LV hypertrophy.

FIG. 6 LIMP-2 is present at the plasma membrane of cardiac myocytes and is important for intercalated disc function. (a) Paraffin-embedded tissue section of pressure-overloaded mouse LV immunostained with anti-LIMP-2 shows positive staining not only in intracellular compartments (*) but also on plasma membranes of cardiac myocytes (▶). Scale bar represents 250 μm. (b) Immuno-electron microscopy with anti-LIMP-2 in pressure-overloaded rat LV tissue sections also shows the presence of LIMP-2 at the plasma membrane (▶). Scale bar represents 1 μm. (c) Electron microscopy shows normal intercalated discs in AngII-treated wild-type mice, while in AngII-treated LIMP-2 KO mice the intercalated discs have a higher degree of convolution and a higher concentration of adherens junctions (appreciate the dark black spots in the right panel), which is paralleled by the dilated cardiomyopathy in these mice. Bars represent 2 μm. M, mitochondrion; ID, intercalated disc; a, adherens junction; d, desmosome.

FIG. 7 LIMP-2 regulates cadherin distribution. (a) LIMP-2 binds to cadherin in neonatal rat ventricular myocytes. LIMP-2 was immunoprecipitated (IP), and cadherin was immunoblotted (IB) in the total cell lysate (input), the supernatant (sup) and the precipitated protein lysate (IP). Part of the cadherin protein content of cardiac myocytes is bound by LIMP-2. (b) Tissue sections of control subject and 2 heart failure patients were immunofluorescently stained with anti-pan-cadherin (red) and anti-LIMP-2 (green). Arrows (▶) show co-localisation of LIMP-2 and cadherin at the ID of cardiac myocytes. Bars represent 50 μm. (c) Tissue sections of AngII-treated LIMP-2 knockout and wild-type LVs were immunostained with anti-pan-cadherin. In wild-type mice the cadherin distribution is confined to the intercalated discs yielding a regular appearance of cadherin, while in LIMP-2 KO mice the localisation of cadherin has lost the typical pattern produced by a strict location at the intercalated disc. Bars represent 250 μm.

FIG. 8 LIMP-2 regulates intercalated disc integrity by regulating the binding of phosphorylated beta-catenin to cadherin. (a) Immunoblot (IB) of lysates of neonatal rat cardiac myocytes that were treated either with shRNA against LIMP-2 (shLIMP-2) or with control shRNA. After 10 days of culture cardiac myocytes show a 92% knockdown of LIMP-2 protein. Equal protein loading was confirmed by GAPDH. (b) Immunoblot (IB) shows diminished levels of P-beta-catenin after immunoprecipitation (IP) with anti-pan-cadherin in shLIMP-2 lysates as compared to control lysates. Cadherin loading was comparable in control and shLIMP-2 IP-lysates. Phosphorylation of beta-catenin in total shLIMP-2 and control protein lysates was comparable. *, P=0.0006. (c) Immunoblot showing the specificity of the immunoprecipitation with anti-pan-cadherin. When adding IgG instead of pan-cadherin antibody to the protein lysates, no P-beta-catenin is bound.

FIG. 9 a. KLF15 expression assessed by real-time CR in left ventricular biopsies from Ren-2 rats at the age of 10 weeks. After biopsy, rats were allowed to recover and followed to determine whether they would progress to failure or remain compensated. Expression of KLF15 is significantly down-regulated in hypertrophied hearts that remained compensated, but significantly further suppressed in the hypertrophied hearts that quickly progressed to overt failure, indicating that the level of KLF15 suppression identifies failure prone forms of cardiac hypertrophy; b. In situ hybridisation for KLF15 in a normotensive control heart compared to hypertrophic myocardium. The widespread nuclear staining in the normal heart is lost in a large number of myocytes, while there is residual staining in non-myocyte nuclei, indicating that KLF15 expression occurs specifically in cardiac myocytes; c. Stable knock-down of KLF15 by lentiviral introduction of short hairpin RNA, induced expression of BNP in cultured NRVM.

FIG. 10 a. Addition of TGFβ (10 ng/ml) to cultured cardiac myocytes almost completely suppressed KLF15 mRNA expression. Stable knock-down of the TGFβ type I receptor by lentiviral introduction of short hairpin RNA abolished this effect, demonstrating that TGFβ via its TGFβ type I receptor is capable of suppressing KLF15 expression; b. Whole heart homogenate immunoblotted against the Tgfβ type I receptor shows a substantial and significant reduction in expression of Tgfβ type I receptor, but no compete loss of the receptor; c. Immunohistochemistry demonstrates that the myocyte specific activation of cre resulted in a clear and robust loss of TGFβ type I receptors from cardiac myocytes when comparing WT hearts to the MerCreMer-TGFβ type I mice; d. Angiotensin II infusion induced a significant hypertrophic response in Wt mice, which was blunted in MerCreMer-TGFβ type I mice; e. Angiotensin II infusion induced a significant loss in fractional shortening as an indicator of loss of cardiac function, which was blunted in MerCreMer-TGFβ receptor mice; f. Angiotensin II infusion and subsequent hypertrophy induced a down-regulation of KLF15, which was blunted in the MerCreMer-TGFβ receptor mice.

Figure 11:
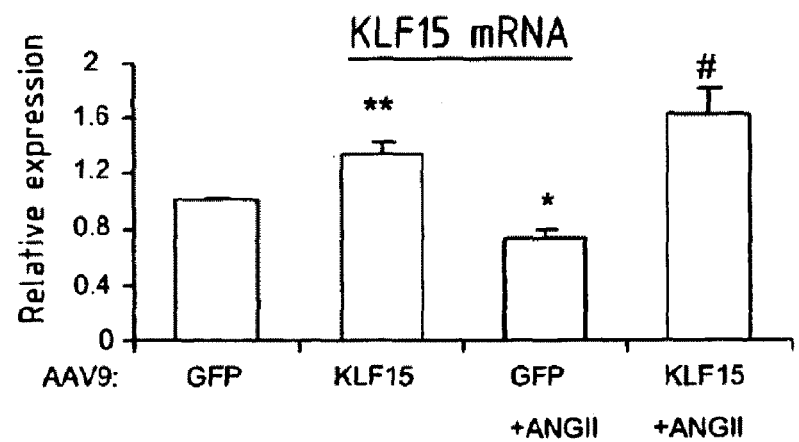
Figure 11:
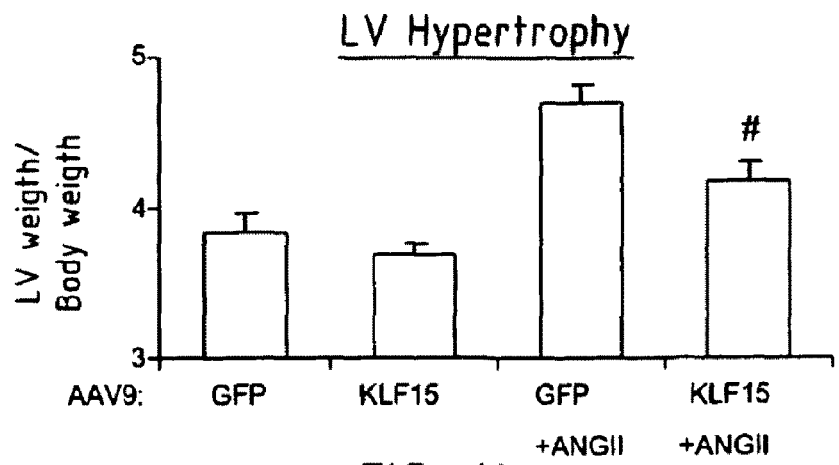

FIG. 11 The upper panel shows significantly upregulated KLF15 mRNA in the mouse heart after AAV9-KLF15 injection, compared to green fluorescent protein (AAV9-GFP) injection. **: p<0.05 camp to GFP group. *: p<0.05 compared to GFP group. #: p<0.05 compared to GFP+AngII group. The lower panel shows significantly less hypertrophy in the AAV9-KLF15 group after AngII stimulation compared to the AAV9-GFP group with AngII (#: p<0.05). Statistical analysis with student's t-test, n=3-5 animals/group.

EXAMPLES

Example 1

Lysosomal Integral Membrane Protein-2 is a Novel Component of Intercalated Discs and Prevents Cardiomyopathy Materials and Methods
Ren-2 Rats, Microarray Analysis and Immunoblotting From 10-weeks old Ren-2 and Sprague-Dawley (SD) rats (Möllegard, Lille Skensveld, Denmark), a biopsy of the LV was taken as described previously (Van Haaften et al., 2006). Rats were followed by serial echocardiography at 10, 12, 15, 16, 18, 19 and 21 weeks of age and sacrificed at 15-18 weeks upon clinical signs of heart failure (heart failure-prone/HF-prone rats) or at 21 weeks when clinical signs of failure had not appeared (compensated/comp rats). Total RNA was isolated from LV biopsies and amplified as previously described (Schroen et al., 2004; Heymans et al., 2005), hybridized to Affymetrix rat 230 2.0 GeneChips and analyzed with Microarray Analysis Suite Software 5.0. LV protein extracts (50 μg) were immunoblotted with polyclonal rabbit anti-LIMP-2 (Novus Biologicals, Littleton, Colo., 1:500) and polyclonal rabbit anti-GAPDH (Abcam, Leusden, Netherlands; 1:10,000).

LIMP-2 Knockout Mice, RNA Isolation and Quantitative PCR Analysis

Ten to twelve weeks-old male LIMP-2 KO and WT C57/B16 mice weighing 20-25 grams were used. To study blood pressure effects of AngII, arterial pressures were monitored during intravenous infusions at doses of 0.5, 1.5, 5, 15, and 50 ng per minute. To study development of LV hypertrophy, AngII (1.5 μg/g/day) was infused subcutaneously by osmotic minipump 2004 (Alzet osmotic pumps, Cupertino, Calif.) for 28 days.

Echocardiography was performed at day 0, day 14 and day 28. At day 28 mice were hemodynamically monitored (dP/dt) using Millar® under basal and dobutamin stimulated conditions, where after LVs were removed. RNA was isolated with RNeasy mini kit (Qiagen, Valencia, Calif.) and SYBR Green quantitative PCR analysis was performed on a BioRad iCycler to determine BNP, ANF and alpha-skeletal actin (aska) expression (Table 1). LV sections were stained with hematoxylin-eosin (HE) and Picro serious red (SR) as described before (Junqueira et al., 1979), or were immunohistochemically stained with monoclonal mouse anti-pan-cadherin (Sigma, Saint Louis, USA; 1:500) and monoclonal mouse anti-human desmin (Dako Cytomation, Denmark, 1:50). Ultrastructural-analysis was performed by transmission electron microscopy as described previously (Schroen et al., 2004).

LIMP-2 in Aortic Stenosis and Heart Failure Patients

RNA was isolated from transmural biopsies obtained from 20 aortic stenosis patients and 7 non-hypertrophic control patients as described before (Heymans et al., 2005), and SYBR Green quantitative PCR analysis was performed to determine LIMP-2 expression (Table 1).

Double immunofluorescent stainings with rabbit anti-LIMP-2 (1:250, Cy2) and mouse anti-pan-cadherin (1:500, Cy3) were done on sections of 1 control subject and 2 patients that died of overt heart failure, as defined by an ejection fraction of less than 35%. Nuclear counterparts were stained with Topro-3 (Invitrogen, Breda, The Netherlands). Sections were imaged with a laser scanning confocal system (Leica, Rijswijk, The Netherlands), digitized at a final magnification of ×126 and analyzed with Leica Confocal Software. The ethics committees of the Academic Hospital Maastricht and of University Hospital Leuven approved the study, and all patients gave informed consent.

Cell Culture and Lentiviral Vector

A rat-LIMP-2 shRNA expressing lentiviral vector was generated by annealing complementary shLIMP-2 oligonucleotides (Table 1) and ligating them into HpaI XhoI digested pLL3.7 puro vector DNA (modified from a kind donation by Luk van Parijs, Massachusetts Institute of Technology, Cambridge, USA). Lentiviral production was performed by co-transfection of 3 μg shLIMP-2/pLL3.7 puro or empty pLL3.7puro and packaging vectors into 293FT cells by Lipofectamine 2000 (Invitrogen) and virus-containing supernatant was harvested after 48 hours.

Rat ventricular cardiac myocytes (RCMs) were isolated by enzymatic disassociation of 1- to 2-day-old neonatal rats as described previously (De Windt et al., 1997). For lentiviral infection, RCMs were plated on gelatinized 6-wells plates with $5*10^5$ cells per well, cultured overnight in DMEM/M199 (4:1) media supplemented with 10% horse serum, 5% newborn calf serum, glucose, gentamycin and AraC, and next day infected with shLIMP-2 or empty lentivirus, facilitated by Polybrene (Sigma). After puromycin selection (3 μg/ml), infection efficiencies were above 80%. After 10 culture days, cellular protein was isolated for immunoprecipitation (IP) with anti-LIMP-2 (1:100), monoclonal mouse anti-pan-cadherin (Sigma, 1:100) or IgG. IP lysates were immunoblotted with monoclonal anti-pan-cadherin (1:5000), polyclonal anti-phospho-beta-catenin (Ser33/37/Thr41; Cell Signaling Technology, Danvers, Mass., USA, 1:1000) and monoclonal anti-beta-catenin (BD Transduction Laboratories, Franklin Lakes, USA, 1:1000).

For stretch experiments, RCMs were cultured on a collagen type I-coated silastic membrane (Specialty Manufacturing, Inc, USA) and subjected to static, equibiaxial stretch during 6 hours. RNA was isolated with RNeasy mini kit (Qiagen) for LIMP-2 SYBR Green quantitative RT-PCR (Table 1). All study protocols involving animal experiments were approved by the Animal Care and Use Committee of the Universiteit Maastricht, and were performed according to the official rules formulated in the Dutch law on care and use of experimental animals, highly similar to those of the NIH.

Statistical Analyses

Data are presented as average±SEM. The data for each study group were compared using Mann Whitney or student's t-test where appropriate. P<0.05 was considered to be statistically significant.

Results

In Table 2, a list is presented of genes differentially expressed in failure-prone as compared to compensated Ren-2 rats. The differential expression of these genes precedes the development of heart failure in Ren-2 rats, because it is derived from cardiac biopsies taken at 10 weeks of age, when all rats still have compensatory hypertrophy.

In Table 3, elaborate echocardiographic data are presented of LIMP-2 WT and KO mice at baseline, and after 14 and 28 days of AngII treatment.

Gene Expression Profile of Failure-Prone LV Hypertrophy

Figure 1B:
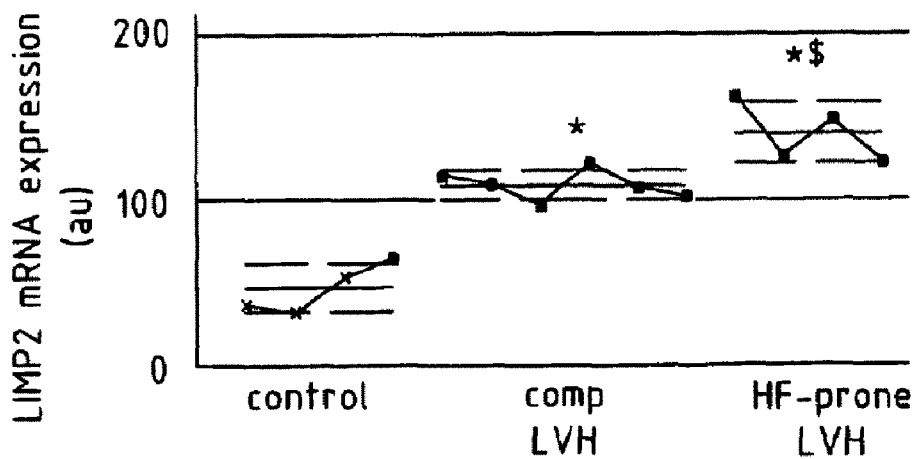
Figure 1C:
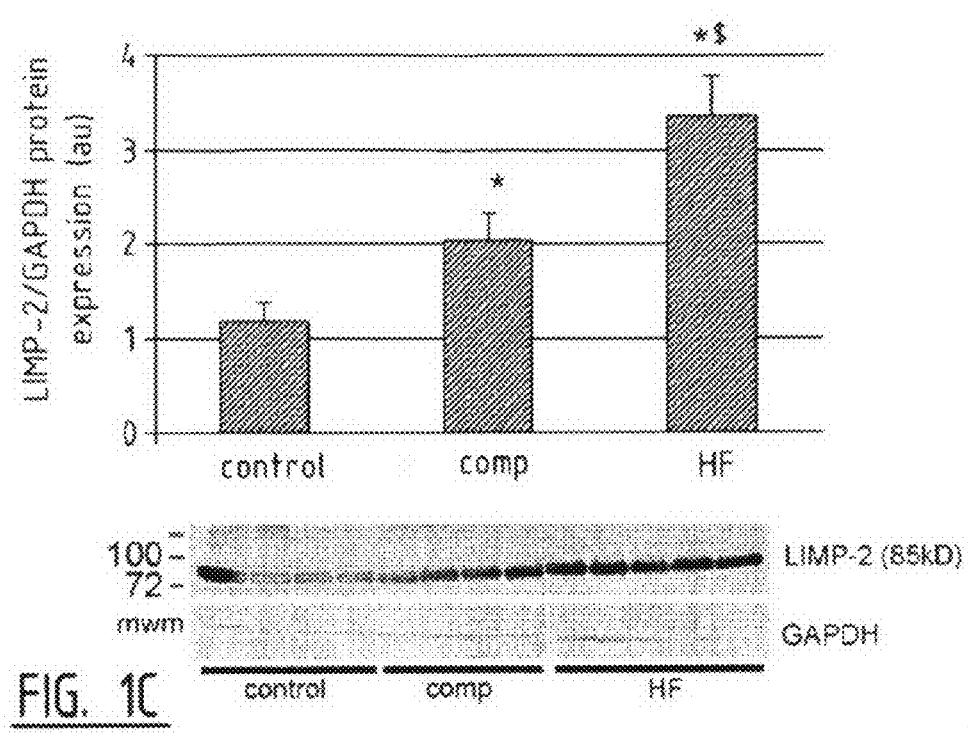

Cardiac biopsies in 10 homozygous Ren-2 rats were obtained at a stage of compensated LV hypertrophy at 10 weeks of age. Four rats rapidly progressed towards heart failure within five weeks after the biopsy was taken, while the remaining 6 rats remained compensated for 11 weeks after biopsy (FIG. 1a). After linear T7 based amplification and subsequent Affymetrix 230 2.0 gene expression analysis in these biopsies (GEO number GSE4286), 143 differentially expressed genes that were up- or downregulated only in the hypertrophied hearts that progressed towards heart failure were identified (Table 2). LIMP-2, a lysosomal membrane protein, was one of the up-regulated mRNAs in heart failure-prone rats (FIG. 1b), and of particular interest given its ability to interact with thrombospondins (TSP) 1 (Crombie et al., 1998) and 2 (data not shown), the latter has been shown earlier to be crucial in the transition from hypertrophy towards heart failure. FIG. 1c shows that LIMP-2 protein also has a role in end-stage heart failure in Ren-2 rats.

Angiotensin II Induces Dilated Cardiomyopathy in LIMP-2 Knockout Mice

Since loss-of-function mutations in lysosomal proteins have been linked to heart failure (Eskelinen et al., 2003; Nishino et al., 2000; Stypmann et al., 2002), the role of LIMP-2 in a mouse model of angiotensin II (AngII) induced hypertension was further investigated. AngII was given subcutaneously for 4 weeks to LIMP-2 knockout and control mice. AngII treatment resulted in a 30% increase in LV mass index in wild-type mice, but the hypertrophic response was attenuated in the AngII-treated LIMP-2 knockout mice (14% increase in LV mass index; $P<0.01$) (FIG. 2a). This was confirmed by measurement of individual cardiac myocyte area. LV myocyte area was significantly smaller in AngII-treated knockout mice than in AngII-treated WT controls (myocyte area in arbitrary units: 264±42 in AngII-treated knockout mice, versus 308±14 in AngII-treated wild-types; $P<0.01$). In addition, while AngII induced comparable increases in perivascular fibrosis in LIMP-2 knockout and wild-type mice (data not shown), AngII induced a massive interstitial fibrotic response in the LV of LIMP-2 knockout mice as opposed to wild-type control littermates (interstitial fibrosis: 15.0±6.0% in AngII-treated knockout mice versus 1.8±0.1% in AngII-treated controls; $P<0.002$) (FIG. 3).

Immunohostochemical staining for desmin showed myocyte disarray in AngII-treated LIMP-2 null mice (FIG. 4).

Figure 2B:
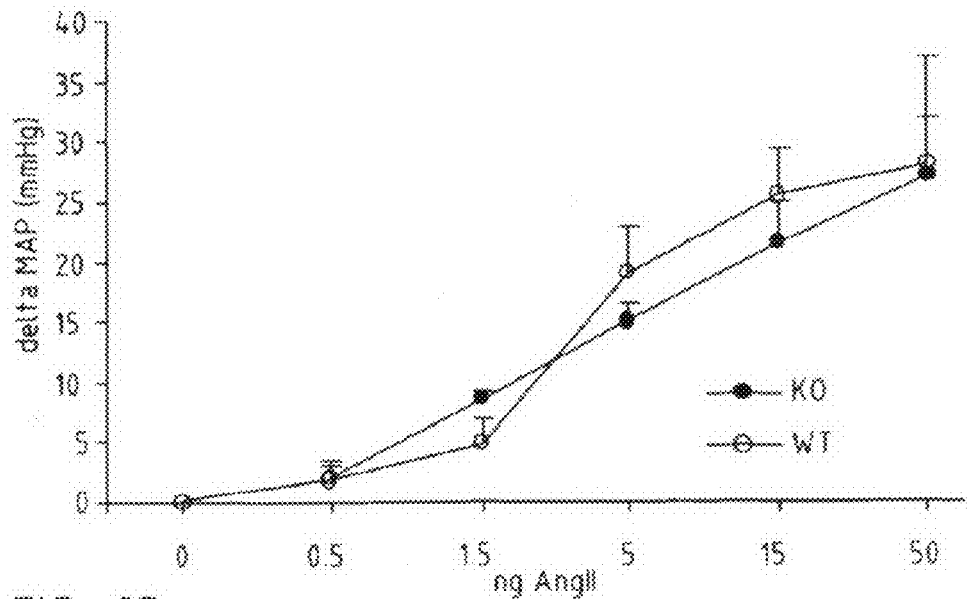
Figure 2A:
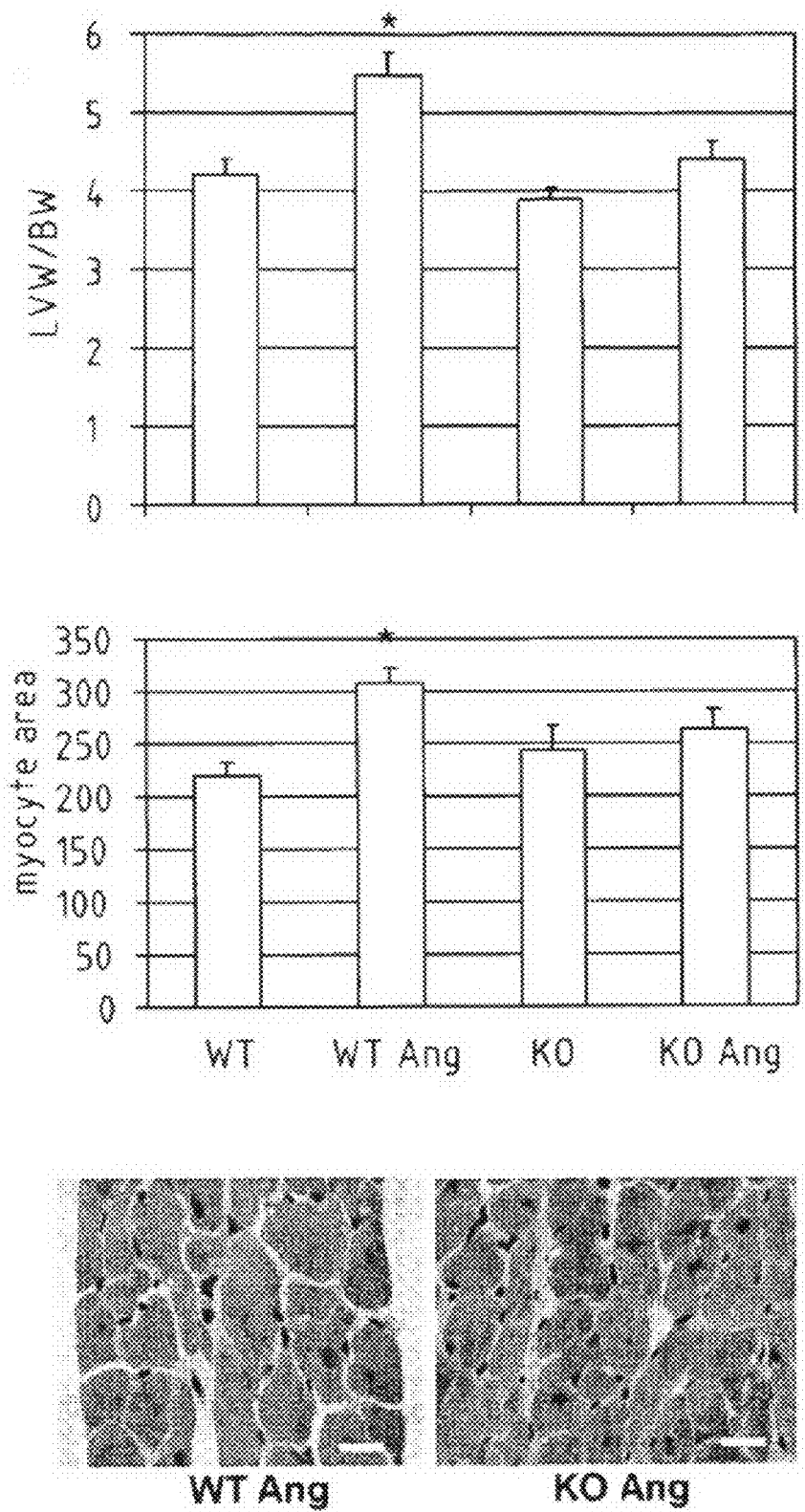
Figure 2C:
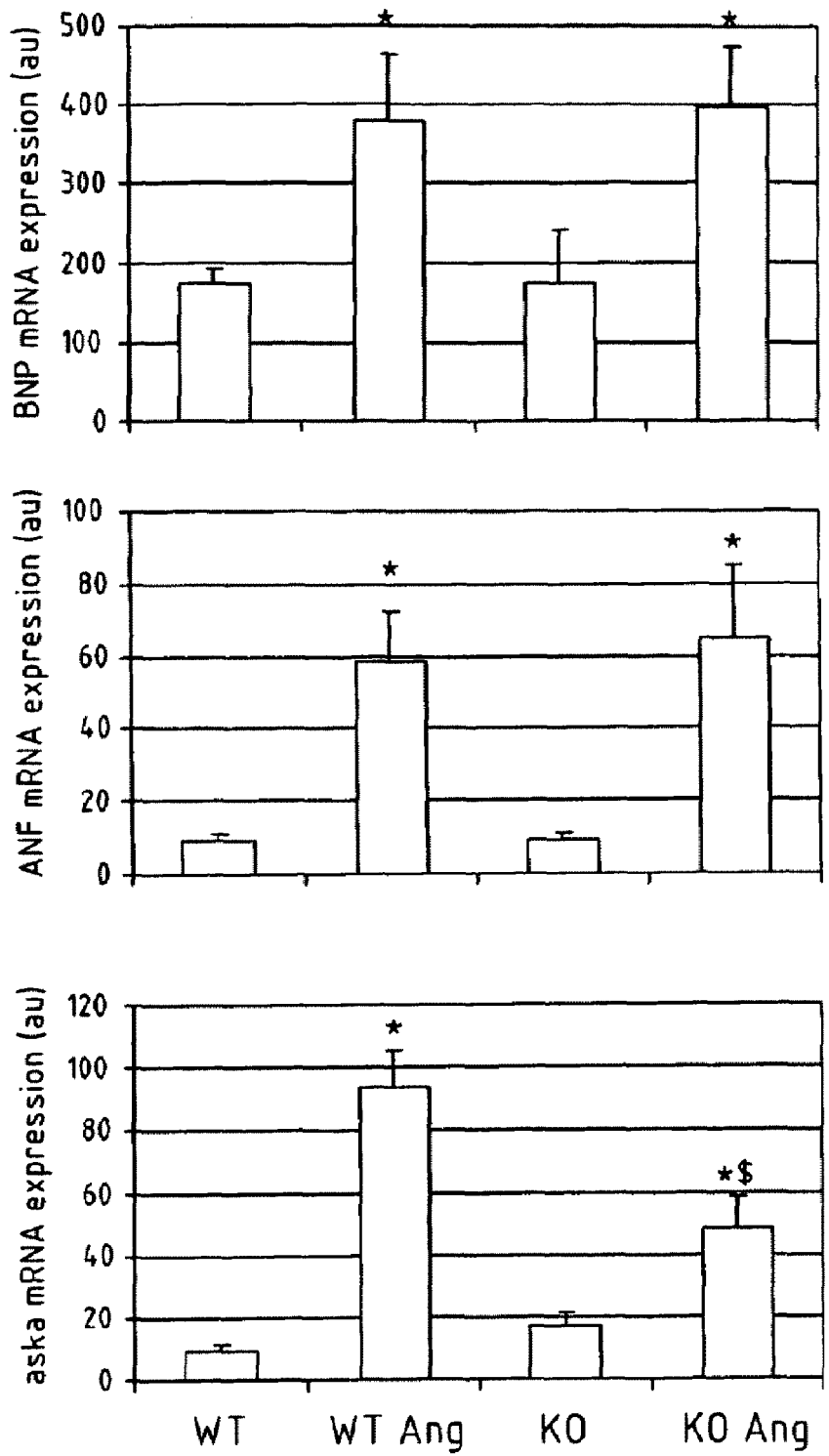
Figure 2D:
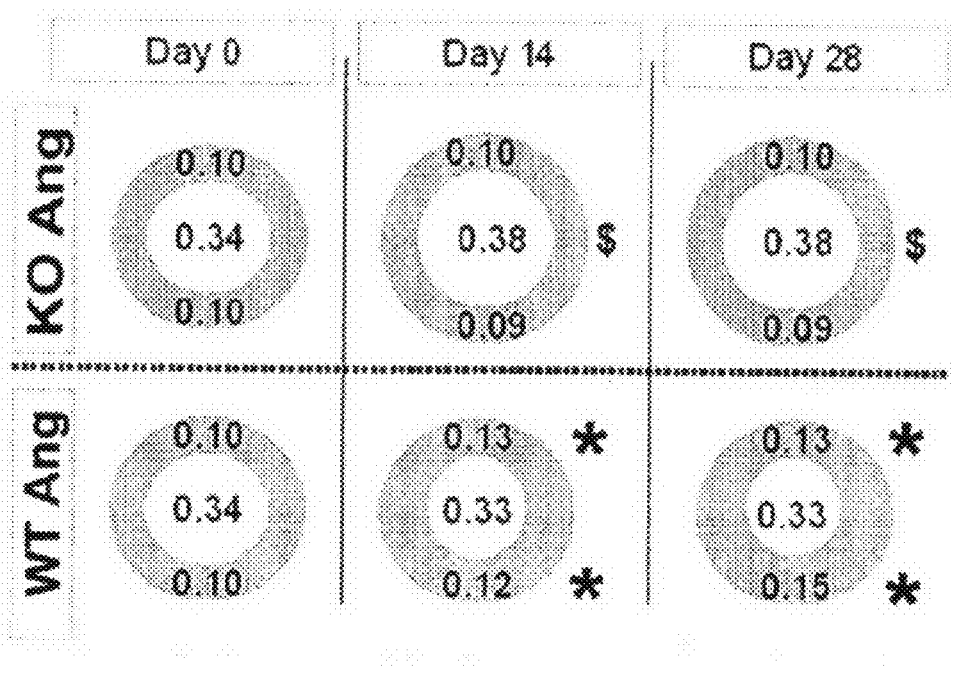
Figure 2E:
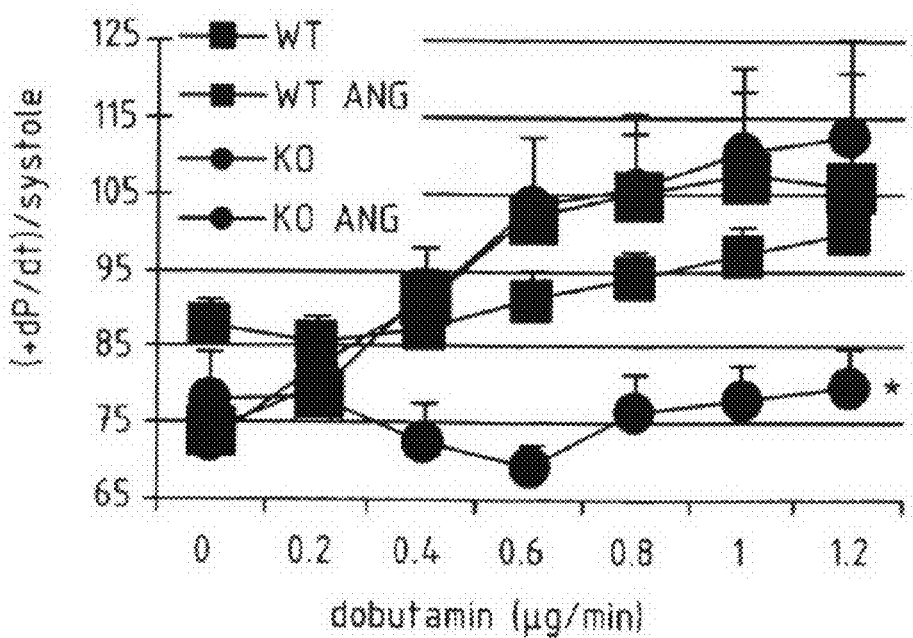

It was confirmed that AngII induced a similar blood pressure response in both wild-type and knockout mice (FIG. 2b). Despite decreased LV hypertrophy, LIMP-2 null mice demonstrated a normal response of the classical markers for hypertrophy Brain Natriuretic Peptide (BNP) and Atrial Natriuretic Factor (ANF) (FIG. 2c), suggesting that the hypertrophic gene expression program was normally initiated upon AngII-treatment. In contrast, the structural cellular hypertrophy marker alpha-skeletal actin was induced to a significantly lesser extent in AngII-treated LIMP-2 knockouts as compared to AngII-treated wild-types (FIG. 2c), reflecting the reduced hypertrophic response of cardiac myocytes (Stilli et al., 2006). Serial echocardiography revealed that AngII induced significant cardiac dilatation in Ang-II treated LIMP-2 null mice, whereas AngII-treated wild-types showed concentric LV hypertrophy without dilatation (FIG. 2d and Table 3). In addition, AngII induced loss of contractile reserve in LIMP-2 null mice as demonstrated by a reduced contractile response to dobutamine infusion (+dP/dt 79.8/second±5.1 in AngII-treated knockout mice versus 100.0/second±4.0 in AngII-treated controls; $P<0.005$) (FIG. 2e).

Taken together, in LIMP-2 null mice hypertension did not induce the normal hypertrophic response but rather dilated cardiomyopathy with reactive interstitial fibrosis and loss of cardiac function.

LIMP-2 Expression is Regulated by Cardiac Stress

The finding that AngII-treated LIMP-2 null mice failed to mount a hypertrophic response, yet normally induced expression of BNP and ANF suggested that LIMP-2 is a crucial part of the normal response to mechanical loading. Indeed it was also shown that LIMP-2 expression increased significantly after cardiac myocyte stretch in vitro ($P=0.02$) and also increased in exercise-induced physiological hypertrophy ($P=0.04$) (FIGS. 5a and b). To ascertain that LIMP-2 is also involved in the human adaptation to cardiac pressure loading, the expression of LIMP-2 was analyzed by quantitative RT-PCR in cardiac biopsies of 20 aortic stenosis patients with overt cardiac hypertrophy and 7 controls. This experiment showed a significant LIMP-2 upregulation in the hypertrophic hearts of aortic stenosis patients as compared to controls by Mann-Whitney test (1.23-fold; $P=2.3e^{-4}$).

LIMP-2 is Present at the Cardiac Intercalated Disc

Figure 6A:
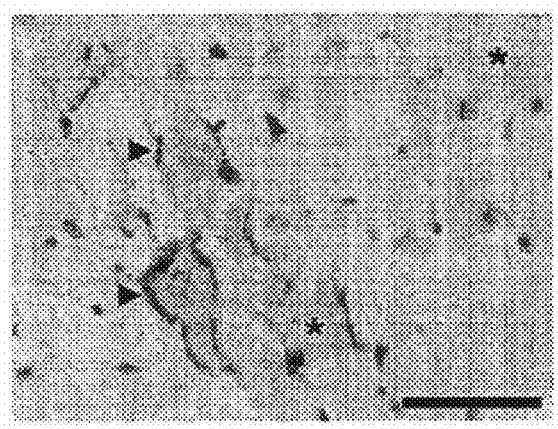
Figure 6B:
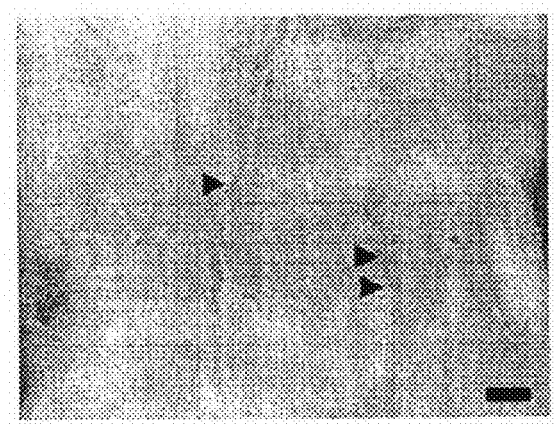
Figure 6C:
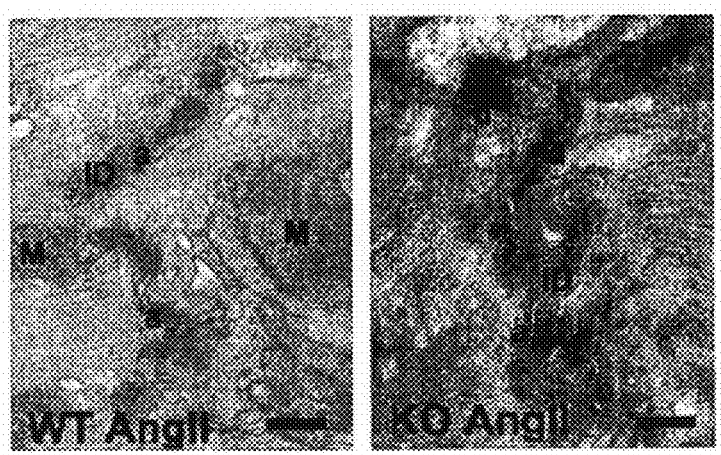

Next the expression pattern of LIMP-2 in pressure overloaded murine myocardium was analysed by immunohistochemistry. The protein is expressed, as expected, in intracellular vacuole-shaped compartments of cardiac myocytes and endothelial cells, but was also found to be atypically distributed on the plasma membrane of cardiac myocytes (FIG. 6a). Immuno-electron microscopy confirmed this finding (FIG. 6b). Strikingly, electron-microscopy of AngII-treated LIMP-2 knockout and control left ventricular sections revealed abnormal morphology of the ID in LIMP-2 null mice, suggesting that LIMP-2 may be involved in normal ID biology. At cell-cell contacts, the membrane at the AngII-treated KO-ID showed a higher degree of convolution with a higher concentration of adherens junction proteins (FIG. 6c), indicative of disturbed ID architecture (Perriard et al., 2003). Since alterations in the ID have been shown to cause dilated cardiomyopathy (Periard et al., 2003), it was surmised that LIMP-2 may be crucial for proper functioning of the ID.

Figure 7A:
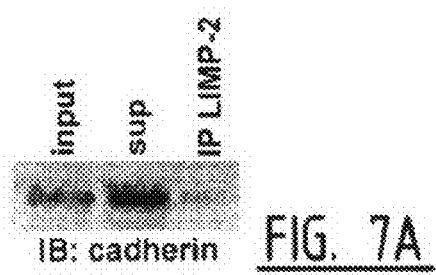
Figure 7B:
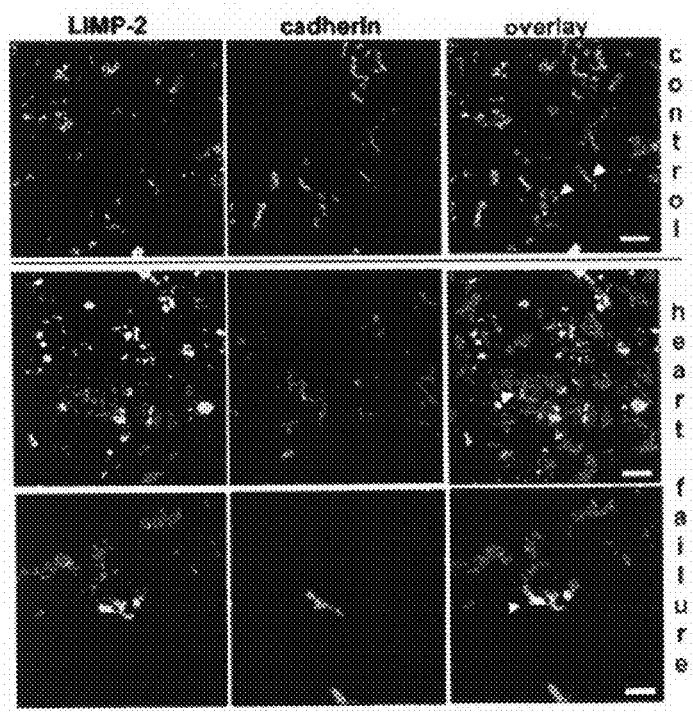
Figure 7C:
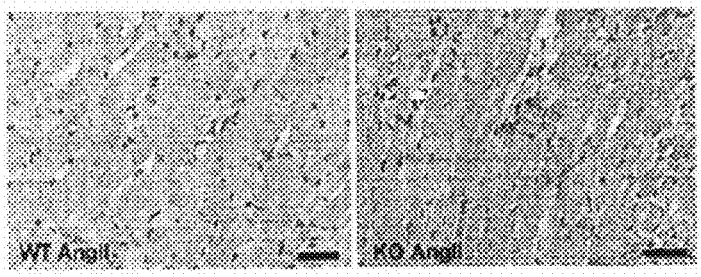

Immunoprecipitation of neonatal rat cardiac myocytes protein showed that LIMP-2 physically interacts with N-cadherin, a vital constituent of adherens junctions (FIG. 7a). This finding was translated to the human situation as confocal microscopy of control as well as failing human myocardium confirmed the interaction between cadherin and LIMP-2 and showed that this interaction takes place at the site of the ID, where cadherin and LIMP-2 co-localize (FIG. 7b). This suggested that LIMP-2 may be important for proper ID function by mediating the role of cadherin. Indeed, histochemical analysis of cadherin in hearts of LIMP-2 null mice showed aberrant cadherin distribution (FIG. 7c), but normal distribution in AngII-treated wild-types. AngII-treated wild-type mice show cadherin expression at the contact sites between two longitudinal cardiac myocytes, while this expression is less organized and more diffuse in cardiac myocytes of AngII-treated LIMP-2 knockout mice. These data establish that LIMP-2 is crucial for the proper structural organization of the intercalated disc.

LIMP-2 Regulates Intercalated Disc Integrity

Figure 8A:
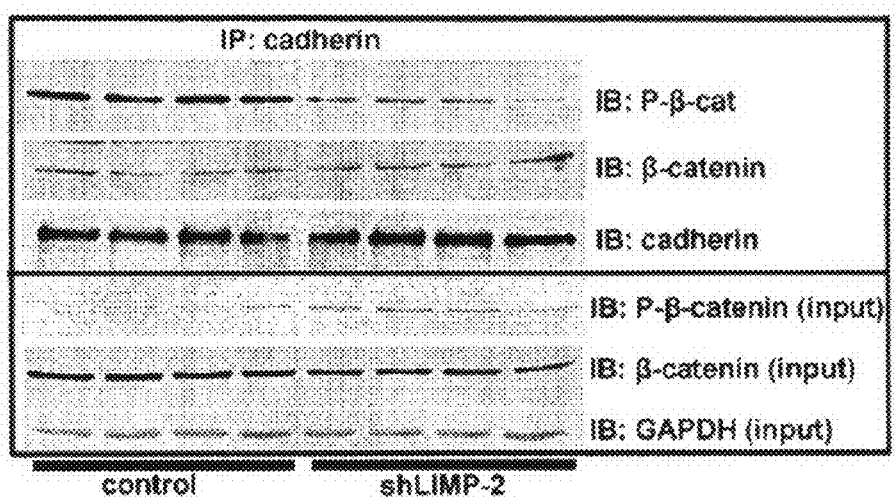

To identify which regulatory mechanism depends on LIMP-2, lentivirally introduced short-hairpin RNA against LIMP-2 (shLIMP-2) was used to obtain a separate model of LIMP-2 inactivation in neonatal rat cardiac myocytes. After 10 days of culture, LIMP-2 protein expression was diminished by 92% in shLIMP-2 treated cardiac myocytes as compared to control treated cardiac myocytes (FIG. 8a). It has been reported that the functional integrity of the intercalated disc depends on the proper interaction between P(Ser37)-β-catenin and cadherin. Therefore, it was investigated whether the absence of LIMP-2 affected the binding of P-β-catenin to cadherin.

Figure 8B:
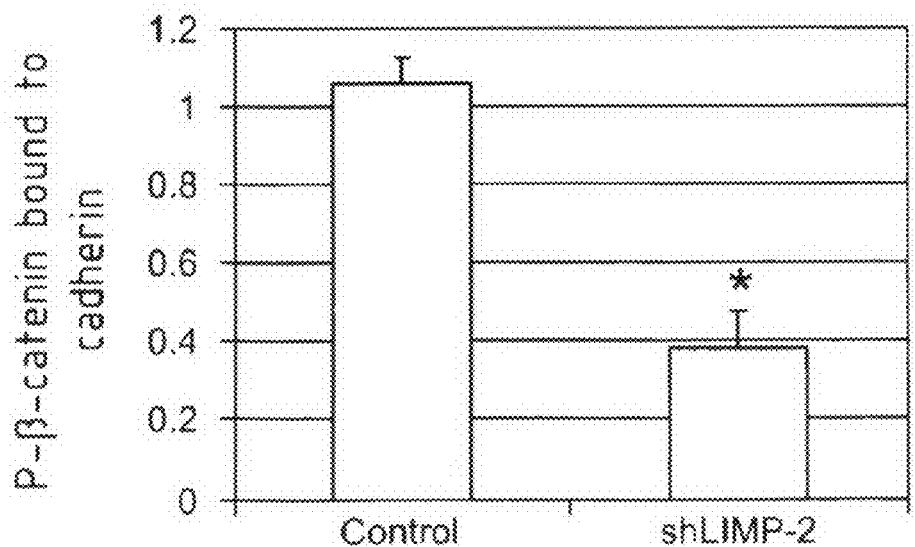
Figure 8C:
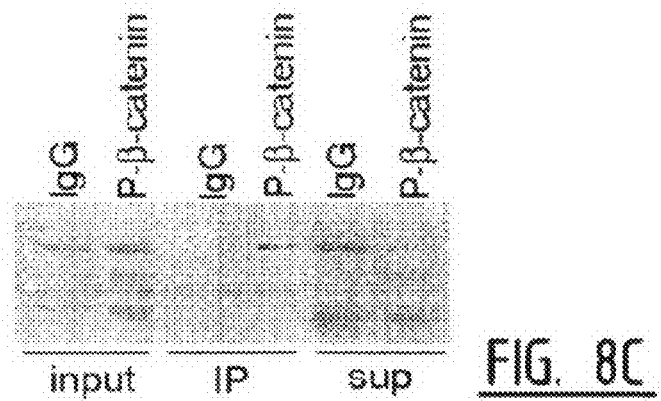

Immunoprecipitation of cadherin in lysates of cardiac myocytes showed that knock-down of LIMP-2 indeed diminished the interaction between P-β-catenin and cadherin (FIG. 8b). Immunoprecipitation was specific for cadherin (FIG. 8c).

It was demonstrated in this study that the lysosomal protein LIMP-2 is an, important and novel component of the cardiac myocyte intercalated disc, in particular adherens junctions. According to the present invention, it has been shown that LIMP-2 binds to N-cadherin, and that LIMP-2 null mice develop dilated cardiomyopathy upon AngII-induced hypertension, accompanied by disturbed localisation of N-cadherin in the heart. Confirming this in-vitro it was shown that knock-down of LIMP-2 in cultured myocytes disturbs interactions between N-cadherin and β-catenin. This suggests that LIMP-2, which was initially known as a lysosomal protein, is an important part of the intercalated disc.

LIMP-2 has a Role in the Heart During Pressure Overload

LIMP-2 stands out among ID proteins. Complete loss of other major constituents of the ID (cadherin, β-catenin, plakoglobin) results in lethal developmental cardiac derangements, suggesting that these components of the ID are essential for normal cardiac development. In contrast, according to the invention it was found that LIMP-2 null mice have normal cardiac development, but that its loss only affects postnatal cardiac remodeling. This suggests that LIMP-2 represents a different type of ID protein, whose role is essential mainly under increased loading conditions. This specific role for LIMP-2 is underlined by the finding that expression of LIMP-2 further rises in hypertrophied rat hearts that are on the brink to progress to failure, which suggests that LIMP-2 expression particularly increases in cardiac myocytes which seem unable to normalize loading conditions. Taken together, it was suggested that LIMP-2 is a novel mediator of ID function, and represents a hitherto unidentified class of mediators that are essential for the ID and the myocyte to respond to increased loading conditions.

LIMP-2 Null Mice Respond Abnormally to Increased Loading

LIMP-2 increased particularly in those hypertrophied hearts that would later progress to failure, in comparison to the hypertrophied hearts that remained compensated. This indicates that cardiac LIMP-2 expression may be an early molecular sign of excessive loading. That LIMP-2 constitutes a defensive mechanism against excessive loading is suggested by the finding that when LIMP-2 null mice were subjected to pressure loading by chronic angiotensin II infusion, they developed cardiac dilatation and fibrosis, yet very little cardiac myocyte hypertrophy. Natriuretic peptides were normally induced, which suggests that the cardiac myocytes of LIMP-2 null mice do sense increased loading conditions, yet fail to mount an adequate hypertrophic response, as evidenced by the attenuated expression of alpha-skeletal actin. This suggests that LIMP-2 is essential for a normal response to cardiac loading, and that LIMP-2 expression is strongly increased when loading conditions exceed compensatory mechanisms. These findings were translated to the human situation, which showed that LIMP-2 is also robustly increased in patients with clinically severe pressure loading. Taken together, LIMP-2 is a novel constituent of the ID and seems to represent a novel type of ID protein, essential for the response to loading rather than for normal cardiac function.

Mechanisms of LIMP-2 Response to Loading

Intercalated disc abnormalities were documented in pressure-loaded LIMP-2 null mice, characteristic of a disturbed cardiac intercalated disc, which normally acts to organise adjoining myocytes. Remodelling of the intercalated disc has been shown previously during the transition from compensated LV hypertrophy towards heart failure, while structural perturbations of the intercalated disc have been linked to dilated cardiomyopathy in humans, hamsters and pigs. It was shown that LIMP-2 binds N-cadherin, suggesting a role for LIMP-2 via this ID constituent. Indeed, pressure overloaded LIMP-2 KO mice show abnormal intercalated discs on electron microscopy and their N-cadherin distribution is disturbed, suggesting a defect in the adherens junctions. The strength of adherens junctions is determined by the binding affinity between N-cadherin and β-catenin (Gumbiner et al., 2000), which is regulated by phosphorylation of the latter. It was shown in-vitro, by knock-down of LIMP-2 in cultured myocytes, that loss of LIMP-2 disturbs this N-cadherin/β-catenin complex. Given the linkage of adherens junctions to myofibrils, a loss of LIMP-2 is expected to lead to less efficient force transduction across the plasma membrane (Ferreira et al., 2002).

It has been suggested that LIMP-2 is essential for the proper binding of N-cadherin to β-catenin, and that this role is particularly important under loading conditions. However, the precise way by which LIMP-2 assures binding of N-cadherin to β-catenin remains to be elucidated. LIMP-2 contains two transmembrane domains, a cytoplasmic loop and two luminal glycosylated domains. It is known that lysosomal membrane proteins can shuttle between lysosomal and plasma membranes, where LIMP-2 can bind to TSP1 and -2 (data not shown). This latter is intriguing, as it has been documented earlier that TSP2 is also essential for the response to cardiac pressure loading and increases in failure prone forms of LV hypertrophy (Schroen et al., 20040. This suggests that both LIMP-2 and TSP2 may be part of a complex that is needed for the cardiac myocyte to mount an adaptive response to loading.

Implications

According to the present invention, a novel role for LIMP2 has been uncovered as an important mediator of the ID when the myocardium faces increased loading conditions. Apart from this novel biological insight, the finding that expression of LIMP-2 rises in hypertrophied rat hearts that are on the brink to progress to failure, makes it tempting to speculate that increased LIMP-2 expression by cardiac myocytes demonstrates their inability to normalize loading conditions. As such, increased LIMP-2 expression may signify imminent failure. Since it has been shown that LIMP-2 expression is also robustly increased in patients with clinically severe pressure loading, and is located at the plasma membrane, LIMP-2 may be an attractive target for molecular imaging to identify already in a very early stage, the myocardium that is about to succumb to the pressure.

Example 2

TGF-Beta Promotes Cardiac Hypertrophy by Suppressing Krüppel Like Factor 15, a Novel Inhibitor of Cardiac Hypertrophy Materials and Methods
Transgenic Rats, Left Ventricular Biopsies and Hemodynamic Studies Eighteen male homozygous Ren-2 rats and 5 age-matched Sprague-Dawley (SD) (Möllegard Breeding Center, Lille Skensveld, Denmark) were studied. Three Ren-2 rats were sacrificed at 10 to 12 weeks of age upon clinical signs of heart failure and excluded from the study. From the remaining healthy 15 Ren-2 rats and 5 SD controls a biopsy of the left ventricle was taken at 10 weeks of age, as described previously. Rats were followed by serial echocardiography at 10, 12, 15, 16, 18, 19 and 21 weeks of age as described above. Nine Ren-2 rats were sacrificed at 15 to 18 weeks of age upon clinical signs of heart failure and designated 'heart failure-prone' rats. The remaining 6 Ren-2 rats were monitored and sacrificed at 21 weeks when clinical signs of failure had not appeared, and they were designated 'compensated' rats.

Microarray Analysis

Total RNA was isolated and amplified as previously described from LV biopsies taken at 10 weeks of age of 4 SD controls, of 6 rats that remained compensated and of 4 heart failure-prone rats. Amplified cRNA was then hybridized to Affymetrix rat 230 2.0 GeneChips. Gene transcript levels of SD controls, compensated and HF rats were determined with Microarray Analysis Suite Software version 5.0 (MAS5.0).

Lentiviral shKLF15 Production

Lentiviral vectors were generated by annealing complementary shKLF-15 oligonucleotides (sense 5'-GATGTA-CACCAAGAGCAGC-3' (SEQ ID NO:1) and antisense 5'-GCTGCTCTTGGTGTACAT-3' (SEQ ID NO:2)) and cloning them into digested pLL3.7 puro vector DNA (kindly donated by Luk van Parijs, Department of Biology, Massachusetts Institute of Technology, Cambridge, USA) using E. Coli DH5a competent cells. Constructs were purified using Qiagen Plasmid Midi kit. 293 FT cells were cultured in DMEM with 10% FCS, 2 mM L-Glut, 10 mM non essential amino acids, 1 mM sodium pyruvate and pen/strep antibiotics. Lentiviral production was performed by co-transfection of 3 µg shKLFl5 or shTgfbr1/pLL3.7 puro or empty pLL3.7 puro and packaging vectors into 293FT cells by Lipofectamine 2000 (Invitrogen Life Technology, Breda, The Netherlands) and virus containing supernatant was harvested, filtrated and snap-frozen after 48 hours.

Neonatal Rat Ventricular Myocyte Experiments

Neonatal rat ventricular myocytes (NRVM) were isolated by enzymatic disassociation of 1-3-day-old neonatal rat hearts as previously described (Schroen et al., 2004). NRVMs were cultured in DMEM/M199 (4:1) media supplemented with 10% horse serum (HS), 5% new born calf serum (NBCS), glucose, gentamycin and 2% antibiotic/antimycotic on a gelatinized 6-well plate with $5*10^5$ cells per well. For shKLF15 infection, NRVM were cultured overnight and the next day infected with shKLF15 and an empty lentiviral control vector, facilitated by polybrene (Sigma). After 48 hours cells were washed free of vector and placed under puromycin selection for another 48 hours. Then, cells were kept under quiescent conditions overnight in DMEM/M199 (4:1), glucose, gentamycin and 10% antibiotic/antimycotic. The next day, medium was replaced by medium containing DMEM/M199, glucose, gentamycin, 5% antibiotic/antimycotic, insulin, L-carnitin and BSA. After 1 hour TGF-b (10 ng/ml medium) was added for 1 hour and whereafter RNA was isolated using the RNeasy mini protocol (Qiagen) for SYBR Green quantitative PCR with KLF15 or BNP primers (F 5'-GCT GCT TTG GGC AGA AGA TAG A-3' (SEQ ID NO:3), R 5'-GCC AGG AGG TCT TCC TAA AAC A-3' (SEQ ID NO: 4)). Knock-down efficiency of shKLF15 is about 80% compared to levels in NRVM infected with an empty lentiviral vector.

MEF2 Luciferase Promotor Assay

NRVM were isolated as described above. Cells were cultured in DMEM/M199 (4:1) media supplemented with 10% horse serum (HS), 5% new born calf serum (NBCS), glucose, gentamycin and 2% antibiotic/antimycotic on a gelatinized 6-well plate with $5*10^5$ cells per well. For shKLF15 infection, NRVM were cultured overnight and the next day infected with shKLF15 and an empty lentiviral control vector, facilitated by polybrene (Sigma). After 48 hours cells were washed free of vector and placed under puromycin selection for another 48 hours. A Mef2 reporter plasmid (pGL2-3xMEF2-luciferase) containing three Mef2 binding sites cloned upstream of the Tata-box and luciferase in the cells via transient transfection. Cells were washed and per well, 1.6 µg of the MEF2 construct was added together with Opti-MEM I media (Invitrogen) and lipofectamine 2000, and antibiotics free media. The next morning, cells were washed and placed under normal culture media for another two days. Cells were kept overnight under low serum conditions (see above) and the next morning AngII (x grams/ml) was added for 4 hours. The luciferase assay was performed using the Luciferase Assay Protocol (Promega).

Generation of Double Transgenic Mice

TGFβRI$^{f/f}$ mice (C57Bl/6 background) generated by flanking exon 3 of TGFβRI with lox-P site (Sohal et al., 2001) were crossed with mice (C57Bl/6 FVB background) containing cre-recombinase under the control of α-MHC promoter (MerCreMer$^{cre/wt}$ (Larsson et al.) to generate heterozygous double transgenic mice that contained TGFβRI$^{fl/wtcre}$ genes. These mice were then back-crossed with TGFβRI$^{f/f}$ mice resulting in a colony with TGFβRI$^{f/cre}$ and TGFβRI$^{f/wcre}$ in a mixed background of C57Bl/6 FVB, and C57BL/6.

DNA Isolation and Genotyping

DNA was isolated from the mouse tail using genomic DNA Purification kit (Promega) according to the manufacturer's instruction. We used PCR to assess the genotype of TβRI flox mice, using the 3 primers, 5-ATG AGT TAT TAG AAG TTG TTT (SEQ ID NO:5), 3'-ACC CTC TCA CTC TTC CTG AGT (SEQ ID NO:6), and 3'-GGA ACT GGG AAA GGA GAT AAC (SEQ ID NO:7) as previously described (Sohal et al., 2001).

Cre Recombination Protocol

To induce α-MHC-coupled cre recombinase in cardiomyocytes, adult TGFβRI$^{f/fcre}$ and TGFβRI$^{f/wtcre}$ double transgenic mice were treated with tamoxifen (Sigma) at a dose of 20 mg/kg per day for 7 days by subcutaneous insertion of mini-osmotic pumps (ALZET, model 200 l). A group of wild type mice was treated with tamoxifen to check whether tamoxifen itself had any effects on cardiac morphology and function. Tamoxifen was dissolved in 10% ethanol and 90% polyethyleneglycol-400 followed by a brief sonification. Mice were allowed to recover for 2 weeks prior to treatment with Ang II or vehicle.

Subcutaneous Implantation of Mini-Osmotic Pumps and Ang II Infusion

Mice of either sex weighing 24-32 g were anesthetized with 2.5% isofluorane. Under sterile conditions, a midscapular incision was made, a pocket was created in the subcutaneous tissue by a blunt dissection and a mini-osmotic pump (ALZET model 2004; ALZACorp., Palo Alto, Calif., USA) filled with saline or Ang II (0.5 mg/kg/day) was inserted. The contents of the mini-osmotic pump were delivered into the local subcutaneous space at a rate of 0.25 µl/hour for 4 weeks. In each group, 7 to 9 mice were recruited for experiments and at least 5 mice from each group completed the experiments. All the dropouts were due to death from anaesthesia except 3 animals in which LV catheterisation did not succeed.

Echocardiography

Transthoracic echocardiography was performed preoperatively and after 4-week of angII infusion in wild type, TGF-βRI−/− and TGFβRI−/+ mice under 2.5% isofluorane anaesthesia. Standard views were obtained in 2D-echocardiography, end-diastolic and end-systolic internal diameters were measured and ejection fraction and fractional shortening were calculated.

Hemodynamic Measurements

Mice were anaesthetized with intraperitoneal injection of urethan. A Millar (1.4 F) catheter (Millar Instruments Inc., Houston, Tex., USA) was placed in the right common carotid artery and advanced into the left ventricle for the measurement of left intraventricular pressure. Body temperature was maintained at 37° C. using a thermally controlled surgical table and monitored with a rectal probe. The mice were then allowed to stabilize for 30 minutes prior to hemodynamic measurements.

Tissue Procurement and Myocardial Morphometry

Following hemodynamic measurements, hearts were rapidly excised, washed in 0.9% sodium chloride solution, atria were removed and the ventricles were cut into pieces. For RNA and protein isolation, samples were snap frozen in liquid nitrogen and stored in −80° C. For histological analysis, left ventricles were fixed in paraformaldehyde (1%) and embedded in paraffin. For the visualization of total collagen, picrosirius staining was performed as described previously. P38 was localized by immunostaining using anti-P38 antibody according to the manufacturer's instruction (Cell Signaling Technology, Leusden, the Netherlands).

Protein Isolation and Western Blotting

Frozen ventricles were crushed and homogenized in radioimmunoassay buffer according to the standard protocol (Santa Cruz Biotechnology, Leiden, the Netherlands). Western blotting was performed using specific antibodies against TβRI (1:1000), total and phospho (P)-Smad2, total and P-P38 (1:1000, Cell Signaling Technology, Leusden, the Netherlands), P-Smad3 (I: 5000, a kind gift from Professor E. Leof and Dr M. Wilkes, Mayo Clinic Cancer Research, Rochester, Minn., USA), collagen I (1:3000) and III (1:500) antibodies (Abcam, Leusden, the Netherlands).

TGFβ Type 1 Receptor Immunohistochemistry

Cardiac tissue sections were deparaffinised and rehydrated and antigen retrieval tissue was incubated overnight with the primary antibody (rabbit anti TGFβ receptor 1 (Santa Cruz SC-398) and subsequently the secondary antibody (Goat anti Rabbit-Biotine (DakoCytomation E0432), whereafter they were treated with Streptavidin-Horseradish Peroxidase (Renaissance TSA TM Biotin System, Perkin Elmer Precisely, Tyramide Signal Amplification kit).

All study protocols described above involving animal experiments were approved by the Animal Care and Use Committee of the Maastricht University, and were performed according to the official rules formulated in the Dutch law on care and use of experimental animals, highly similar to those of the NIH.

Statistical Analyses

Data are shown as mean±SEM. Unpaired t-test was performed to compare the difference between the means of Ang II/TGFβ/shKLF15 and vehicle treated animals and cells. P-values of ≦0.05 were considered statistically significant.

Results

It has previously been shown that the outbred homozygous hypertensive TGR(mRen2)27 rat (Ren-2) allows to study the transition from hypertrophy towards heart failure (Schroen et al., 2004). Myocardial biopsies obtained at the age of 10 weeks were used to investigate whether altered gene expression can predict which rat later will later progress to heart failure.

Figure 9A:
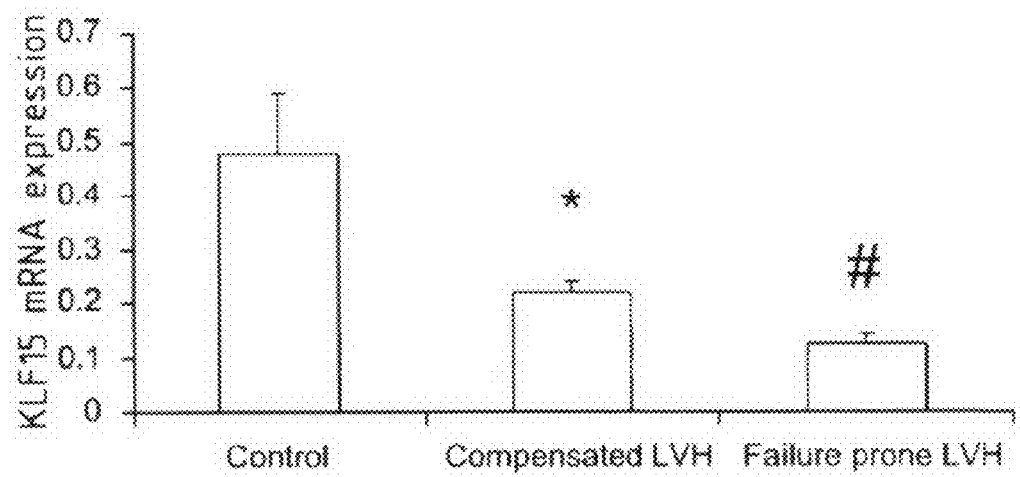
Figure 9B:
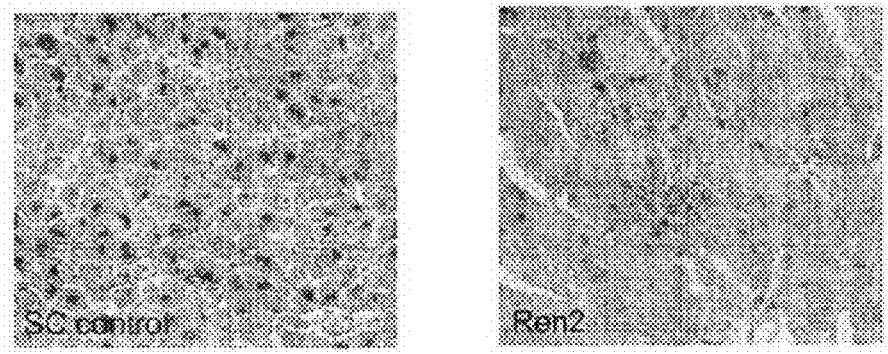
Figure 9C:
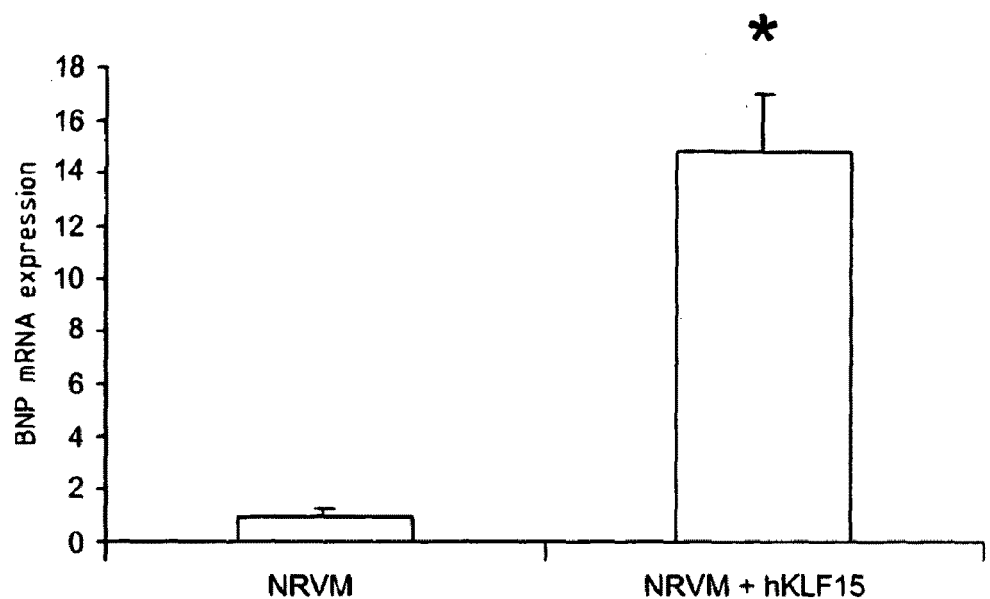
Figure 9D:
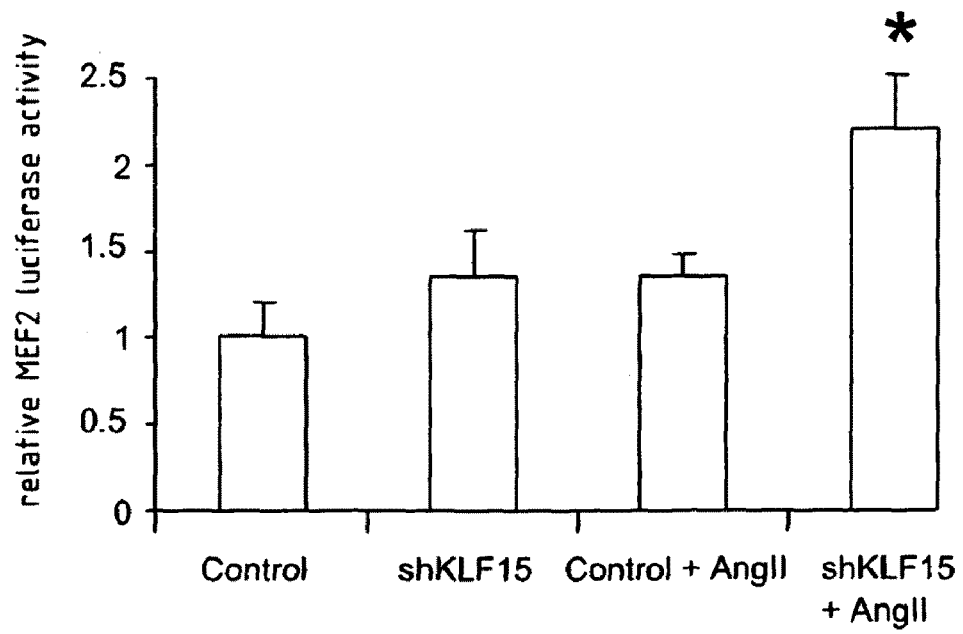

Expression profiling of these biopsies revealed that suppression of the gene coding for Krüppel-like factor 15 (KLF15) characterised the hypertrophied hearts that would quickly progress to failure. This was confirmed by real-time PCR which showed that KLF15 was down-regulated in compensated LVH, but that it was significantly further suppressed in the hypertrophied hearts that quickly progressed to failure (FIG. 9a). In-situ hybridisation showed that expression of KLF15 was particularly down-regulated in cardiac myocytes (FIG. 9b). These findings extend earlier observations that KLF15 is constitutively expressed in the heart, but down-regulated in hypertrophy. That more intense suppression of KLF15 preceded the transition towards heart failure, has led to the suggestion that KLF15 has important protective properties. To explore the functional role of KLF15, a short hairpin RNA (shRNA) against KLF15 was stably introduced. Spontaneous expression of BNP, a molecular hallmark of the hypertrophy gene program, was induced more than 10-fold upon shRNA mediated suppression of KLF15 in cultured cardiac myocytes (FIG. 9c). This suggests that the constitutive presence of KLF15 is important to prevent the expression of the hypertrophy gene program.

In a parallel study, it has been shown that KLF15 null mice develop hypertrophy and cardiac function loss upon pressure loading, underlining that constitutively expressed KLF15 is essential to protect against maladaptive forms of LVH.

To explore the mechanism by which KLF15 can repress the hypertrophy gene program, its role in activation of MEF2 was studied. MEF2 is a target for hypertrophic signalling conveyed by the calcineurin and the MAPK pathway and is recognized as one of the crucial transcriptional activators of the hypertrophy gene program. A MEF2 reporter construct was used to address whether altered levels of KLF15 affect MEF2 activity in cardiac myocytes. This reporter only weakly responds to stimulation by MEF2 (Creemers, Olson unpublished data). Indeed only minor increases in MEF2 activity were observed in response to angiotensin II. However, knockdown of KLF15 significantly increased MEF2 activity (FIG. 9c) suggesting that KLF15 acts as a repressor of MEF2.

It was next sought to explore which mechanism suppresses KLF15 in cardiac myocytes. Therefore known mediators of cardiac hypertrophy were screened for their ability to inhibit KLF15 expression in cardiac myocytes. In cultured cardiac myocytes, TGFβ very robustly suppressed KLF15, so that expression of KLF15 was almost completely abolished after addition of TGFβ. Knockdown of the TGFβ type I receptor by inhibitory RNA prevented the suppression of KLF15 by TGFβ (FIG. 10a) demonstrating that classical TGFβ signalling involving its type I receptor is essential for this effect.

Figure 10A:
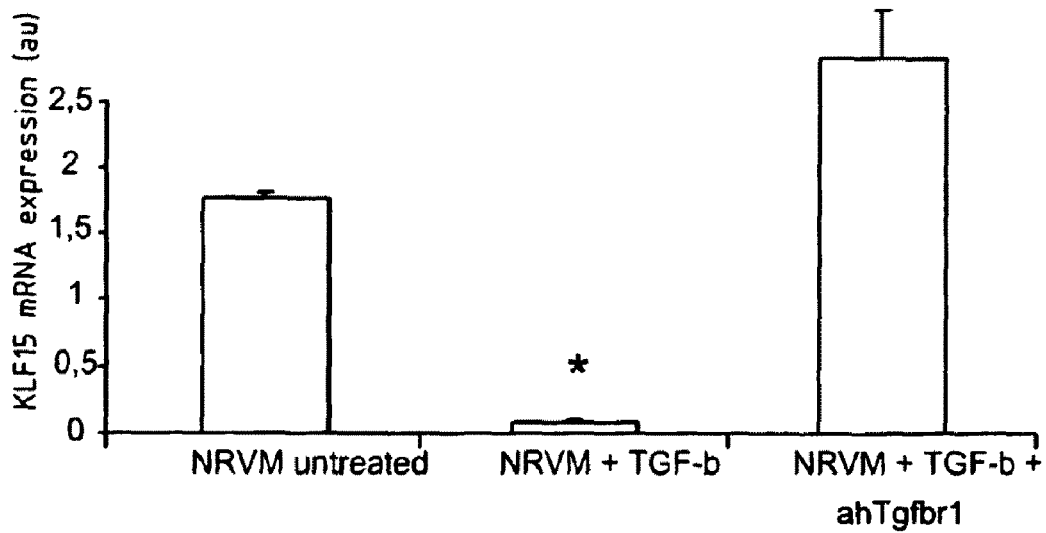
Figure 10B:
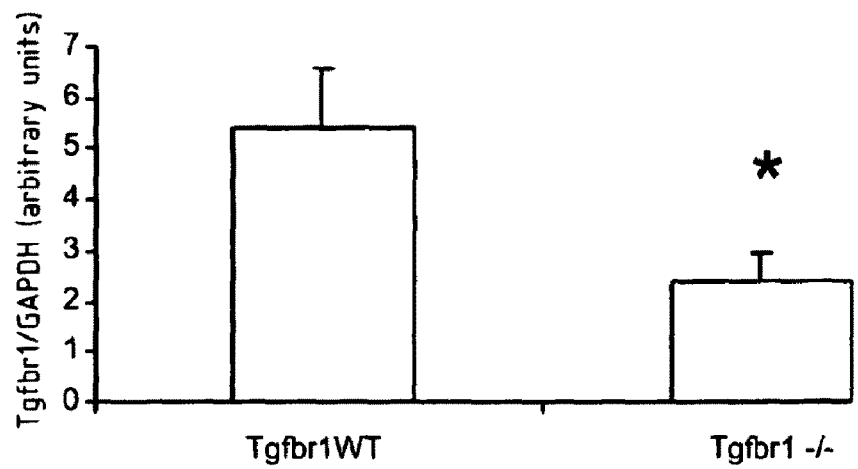
Figure 10C:
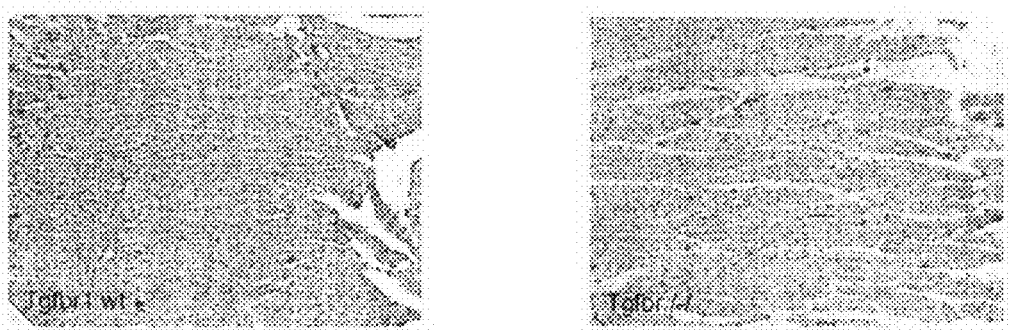
Figure 10D:
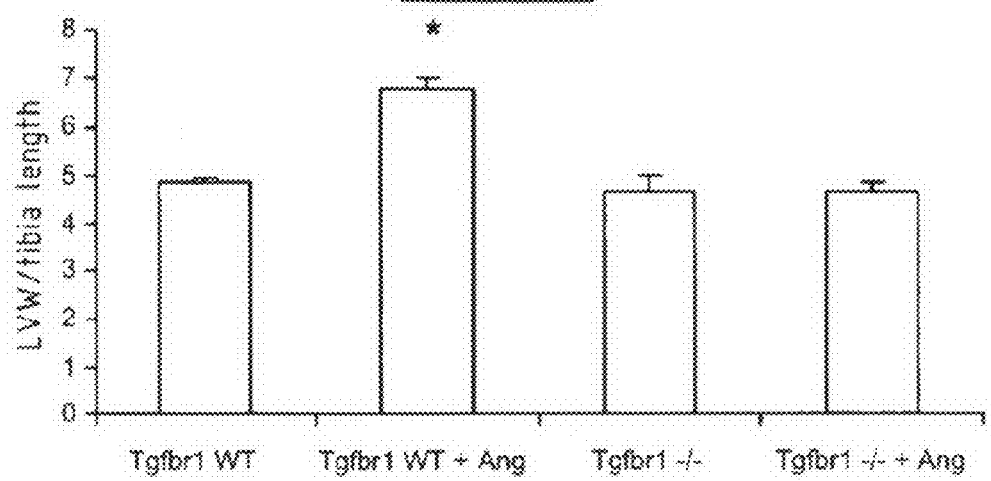
Figure 10E:
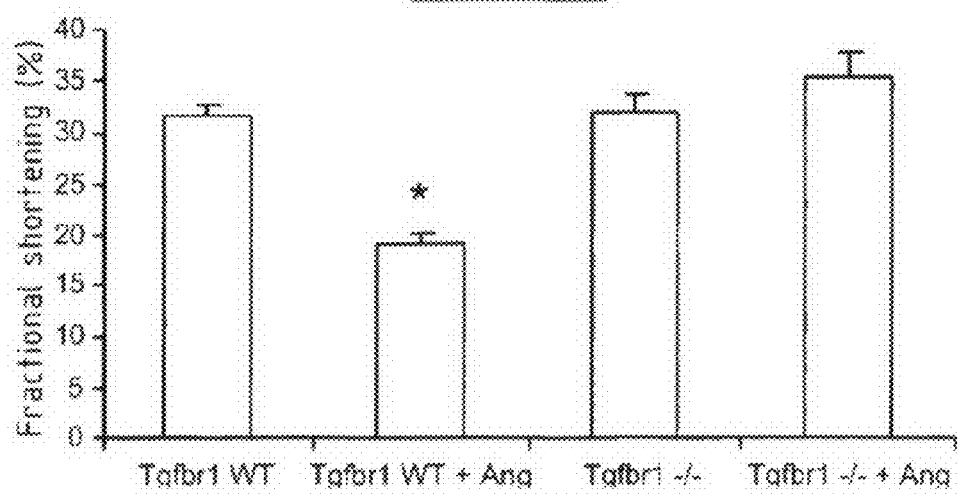
Figure 10G:
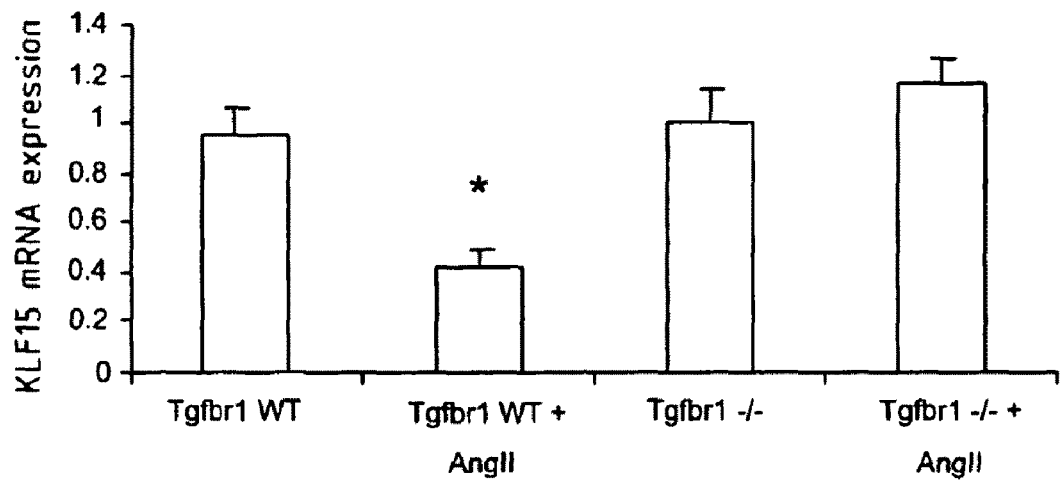

Therefore, to address the regulation of KLF15 by the TGFβ type I receptor in-vivo mice carrying a floxed TGFβ receptor type I gene combined with the MerCreMer allele were generated which allows to activate cre specifically in cardiac myocytes by administration of tamoxifen (Larsson et al., Sohal et al., 2001). This allowed to delete the TGFβ type I receptor specifically in cardiac myocytes in adult mice, avoiding the developmental effects of an embryonic loss of the TGFβ I receptor. Hypertension was induced by chronic angiotensin II infusion as described above in these mice to provoke hypertrophy and down-regulation of KLF15. Western blotting of whole heart homogenate revealed a significant down-regulation of the TGFβ type I receptor (FIG. 10b). Immunohistochemistry confirmed the myocyte specific down-regulation of the TGFβ type I receptor, and showed the expression of this receptor in other cell types explaining the residual signal of the TGFβ type I receptor found in the whole heart homogenate (FIG. 10c). Angiotensin II induced LVH in wild type mice, but the development of LVH was prevented in the MerCreMer-TGFβ type I mice (FIG. 10f). While in WT mice angiotensin II decreased fractional shortening, fractional shortening remained preserved in the MerCreMer-TGFβ type I mice. This indicates that loss of the TGFβ type I receptor from cardiac myocytes can prevent hypertension induced hypertrophy and function loss. As expected, the expression of KLF15 was suppressed in the hypertrophied hearts from WT mice, but this suppression was absent in the hearts of MerCreMer-TGFβ type I mice (FIG. 10g). This shows that the TGFβ type I receptor on cardiac myocytes is important for the development of hypertensive hypertrophy, and at the same time for the suppression of KLF15.

Taken together, KLF15 is the first Krüppel Like Factor to have a role in cardiac myocytes as a suppressor of cardiac hypertrophy. KLF15 inhibits MEF2 and parallel work shows it inhibits other prohypertrophic transcription factors like GAT4 as well. Consequently, it is conceivable that loss of KLF15 very robustly induces hypertrophic gene expression and is related to an adverse outcome. Suppression of KLF15 may therefore be a novel and crucial step in the development of failure prone forms of hypertrophy. It has been shown that TGFβ very robustly can suppress KLF15. Inhibitors of TGFβ, which are currently being developed in different fields, thus may have unexpected therapeutic potential as to prevent cardiac hypertrophy from progressing towards heart failure.

Conclusion

The heart hypertrophies in response to loading and injury, which often progresses towards overt heart failure. According to the present invention, a novel mechanism in this process is unveiled, where the cytokine TGFβ suppresses a novel inhibitor of hypertrophy, Krüppel Like factor 15 (KLF-15). Loss of the TGFβ type I receptor in-vivo and in-vitro prevents the suppression of KLF-15 and the development of cardiac hypertrophy and failure. The finding that TGFβ can hinder this novel mechanism that suppresses cardiac hypertrophy, opens exciting possibilities for inhibition of TGFβ signalling to prevent adverse forms of cardiac hypertrophy.

Example 3

Krüppel-Like Factor 15, a Transcriptional Repressor of Cardiac Hypertrophy

According to the invention it has been shown that the zinc-finger transcription factor, Krüppel-like factor-15 (KLF-15) is a potent transcriptional repressor of LV hypertrophy. Gene-targeting studies showed that KLF15 null mice develop normally, but in response to pressure overload, develop an exaggerated form of cardiac hypertrophy, characterized by increased heart weight, increased expression of hypertrophic genes, left ventricular cavity dilatation with increased myocyte size and reduced left ventricular systolic function. All together, these studies demonstrate a role for KLF15 in LV hypertrophy, in vivo.

Interestingly, KLF15 is down-regulated in several forms of pathological but not physiological hypertrophy, indicating that KLF15 is a regulator of pathological hypertrophy, but not of physiological hypertrophy. The fact that KLF15 counteracts hypertrophy and the additional observation that KLF15 is significantly down-regulated in pathological hypertrophy and heart failure led to the exciting possibility that interventions aimed at preventing the decrease of KLF15 levels could prevent or even reverse pathological growth.

In Vivo Experiment

To test the intriguing possibility that preventing the loss of KLF15 during pathological hypertrophy may limit pathological growth of the heart, KLF15 was overexpressed specifically in the mouse heart using recombinant adeno-associated virus (rAAV)-mediated gene delivery under the control of the cardiac troponin I promoter (Vandedriessche et al., 2007). In particular, rAAV9 vectors have been shown to achieve a robust increase of transgene expression in cardiac tissue for several weeks following intravenous administration.

Mice were intravenously injected with $1\times10^{10}$ vg AAV9-KLF15 or AAV9-GFP, after which hypertrophy was induced by Angiotensin II (AngII) treatment (4 weeks, through osmotic minipumps). As shown in FIG. 11 (upper panel) KLF15 was overexpressed in the heart. Strikingly, mice allocated to AAV9-KLF15 gene transfer developed significantly less hypertrophy upon AngII stimulation, compared to AngII treated mice that received AAV9-GFP. (see FIG. 11, lower panel). Together, these-data show that forced expression of KLF-15 in cardiac myocytes suffices to reduce cardiac hypertrophy.

Conclusion

Loss of KLF15 is a vital step in the development of hypertrophy and the transition towards heart failure. The observation that cardiac overexpression of KLF15 inhibits the development of pathological hypertrophy opens exciting possibilities for strategies that prevent the down-regulation of KLF15 in vivo to prevent hypertrophy and subsequent heart failure

TABLE 1

List of primers for SYBR Green PCR and for shLIMP-2 production

| Gene | | Primer Sequence |
|------|---|-----------------|
| Mouse-BNP | F | 5'-GTTTGGGCTGTAACGCACTGA-3' (SEQ ID NO: 8) |
| | R | 5'-GAAAGAGACCCAGGCAGAGTCA-3' (SEQ ID NO: 9) |
| Mouse-ANF | F | 5'-ATTGACAGGATTGGAGCCCAGAGT-3' (SEQ ID NO: 10) |
| | R | 5'-TGACACACCACAAGGGCTTAGGAT-3' (SEQ ID NO: 11) |
| Mouse-aska | F | 5'-TGAGACCACCTACAACAGCA-3' (SEQ ID NO: 12) |
| | R | 5'-CCAGAGCTGTGATCTCCTTC-3' (SEQ ID NO: 13) |
| Mouse-PPIA[a] | F | 5'-CAAATGCTGGACCAAACACAA-3' (SEQ ID NO: 14) |
| | R | 5'-GCCATCCAGCCATTCAGTCT-3' (SEQ ID NO: 15) |
| Human-LIMP-2 | F | 5'-GTTTGGGCTGTAACGCACTGA-3' (SEQ ID NO: 16) |
| | R | GAAAGAGACCCAGGCAGAGTCA-3' (SEQ ID NO: 17) |
| Human-GAPDH[a] | F | 5'-ACCCACTCCTCCACCTTTGAC-3' (SEQ ID NO: 18) |
| | R | 5'-ACCCTGTTGCTGTAGCCAAATT-3' (SEQ ID NO: 19) |
| Rat-LIMP-2 | F | 5'-TGCGTCCAAACAAGGAAGAAC-3' (SEQ ID NO: 20) |
| | R | 5'-AATCTCTTGGCCCCTCTTAAAATAA-3' (SEQ ID NO: 21) |
| Rat-PGK-1[a] | F | 5'-CGGAGACACCGCCACTTG-3' (SEQ ID NO: 22) |
| | R | 5'-AAGGCAGGAAAATACTAAACATTGC-3' (SEQ ID NO: 23) |
| Rat-shLIMP-2[b] | Sense | 5'-GGAAGAACATGAGTCATTT *GTCAAGAGA* AAATGACTCATGTTCTTCCTTTTTC-3' (SEQ ID NO: 24) |
| | Antisense | 5'-TCGAGAAAAAGGAAGAACATGAGTCATT T*TCTCTTGAC*AAATGACTCATGTTCTTC C-3' (SEQ ID NO: 25) |

[a]Housekeeping genes: cyclophilin A (PPIA), glyceraldehyde 3-phosphate dehydrogenase (GAPDH), phosphoglycerate kinase 1 (PGK-1)
[b]Rat-shLIMP-2 oligonucleotides; hairpin structure in bold italic

TABLE 2

Genes that are differentially expressed in biopsies of failure-prone Ren-2 rats as compared to compensated Ren-2 rats.

| Probe Set ID[a] | p-value[b] | Fold Change[c] | Gene Name[d] |
|---|---|---|---|
| 1374153_at | 0.000052 | 4.64 | Transcribed locus |
| 1393098_at | 0.000074 | −1.39 | similar to Lethal giant larvae homolog 2 |
| 1374120_at | 0.000116 | −1.89 | similar to KIAA1126 protein (predicted) |
| 1382598_at | 0.000201 | 1.49 | heat shock factor 2 |
| 1385234_at | 0.000237 | −1.67 | Transcribed locus |
| 1389074_at | 0.000515 | 1.36 | FCH and double SH3 domains 2 (predicted) |
| 1376763_at | 0.000520 | 1.23 | Transcribed locus |
| 1369722_a_at | 0.000529 | −1.31 | xylosyltransferase II |
| 1377000_at | 0.000593 | −3.11 | similar to junction-mediating and regulatory protein; p300 transcriptional cofactor JMY |
| 1374560_at | 0.000652 | 1.56 | similar to RIKEN cDNA 3110038B19 |
| 1379466_at | 0.000692 | −1.50 | Shadow of prion protein |
| 1385586_at | 0.000774 | −1.41 | Solute carrier family 2 (facilitated glucose transporter), member 6 (predicted) |
| 1370265_at | 0.000784 | 1.82 | Arrestin, beta 2 |
| 1375827_at | 0.001303 | 2.46 | similar to zinc-finger protein |
| 1370102_at | 0.001335 | −1.89 | potassium intermediate/small conductance calcium-activated channel, subfamily, N, member 1 |
| 1384938_at | 0.001399 | −1.28 | Rho GTPase activating protein 1 (predicted) |
| 1375415_at | 0.001433 | 1.22 | similar to U7 snRNP-specific Sm-like protein LSM10 |
| 1380961_at | 0.001458 | −1.59 | CCAAT/enhancer binding protein (C/EBP), gamma |
| 1392644_s_at | 0.001475 | −2.35 | similar to RIKEN cDNA 2610019F03 |
| 1377928_at | 0.001490 | −1.95 | similar to RIKEN cDNA 1810018L02 |
| 1368950_a_at | 0.001579 | −2.06 | glutamate receptor, ionotropic, NMDA2D |
| 1368553_at | 0.001633 | 1.47 | activin A receptor type II-like 1 |
| 1389569_at | 0.001702 | 1.31 | similar to BRIX (predicted) |
| 1374495_at | 0.001744 | −1.30 | LPS-responsive beige-like anchor (predicted) |
| 1397694_at | 0.001928 | −2.94 | potassium channel modulatory factor 1 (predicted)///similar to RNA binding motif and ELMO domain 1 |
| 1397750_at | 0.001951 | 1.36 | Transcribed locus |
| 1373541_at | 0.002074 | −1.29 | Rho guanine nucleotide exchange factor (GEF) 17 (predicted) |
| 1368998_at | 0.002089 | −1.93 | NK6 transcription factor related, locus 1 (*Drosophila*) |
| 1382183_at | 0.002205 | 1.62 | Transcribed locus |
| 1381635_at | 0.002217 | −1.60 | Collagen, type XVIII, alpha 1 |
| 1374536_at | 0.002228 | −1.15 | LOC499569 |
| 1385494_at | 0.002248 | −2.24 | similar to RIKEN cDNA 4930451A13 (predicted) |
| 1390663_at | 0.002310 | −1.36 | Transcribed locus |
| 1395547_at | 0.002465 | −2.57 | Guanine nucleotide binding protein, alpha q polypeptide |
| 1390818_at | 0.002500 | −1.29 | ATPase, Na+/K+ transporting, beta 3 polypeptide |
| 1381396_s_at | 0.002502 | −2.02 | Kruppel-like factor 15 |
| 1374216_at | 0.002528 | −1.25 | Transcribed locus |
| 1386857_at | 0.002661 | 1.23 | Stathmin 1 |
| 1372140_at | 0.002774 | −1.33 | similar to chromosome 6 open reading frame 80; chemokine C-C motif receptor-like 1 adjacent (predicted) |
| 1379930_at | 0.002805 | −3.02 | Transcribed locus |
| 1376179_at | 0.002832 | −1.51 | Transcribed locus |
| 1399140_at | 0.002847 | 1.14 | Transcribed locus |
| 1387923_at | 0.002922 | −1.47 | zinc finger protein 179 |
| 1372789_at | 0.002997 | 1.35 | zinc finger protein 1 |
| 1395400_at | 0.003131 | −2.65 | similar to hypothetical protein MGC23280 |
| 1390600_at | 0.003208 | −1.42 | alpha-2,6-sialyltransferase ST6GalNAc IV |
| 1368024_at | 0.003228 | −1.32 | Quiescin Q6 |
| 1387555_at | 0.003235 | −1.90 | amiloride-sensitive cation channel 2, neuronal |
| 1395863_at | 0.003299 | 1.34 | nuclear receptor subfamily 2, group F, member 2 |
| 1394609_at | 0.003309 | −1.58 | actin-binding LIM protein 2 |
| 1381045_at | 0.003350 | 1.54 | Transcribed locus |
| 1377956_at | 0.003355 | −1.67 | Cofilin 2, muscle (predicted) |
| 1392061_at | 0.003497 | −1.89 | minichromosome maintenance deficient 10 (*S. cerevisiae*) (predicted) |
| 1394986_at | 0.003538 | −1.42 | Similar to KIAA1838 protein (predicted) |
| 1397855_at | 0.003753 | 2.68 | Similar to cysteine sulfinic acid decarboxylase |

TABLE 2-continued

Genes that are differentially expressed in biopsies of failure-prone Ren-2 rats as compared to compensated Ren-2 rats.

| Probe Set ID[a] | p-value[b] | Fold Change[c] | Gene Name[d] |
|---|---|---|---|
| 1375291_at | 0.003813 | −1.76 | Transcribed locus, strongly similar to NP_733751.1 myeloid/lymphoid or mixed-lineage leukemia 3; myeloid/lymphoid or mixed-lineage leukemia3; ALR-like protein [*Homo sapiens*] |
| 1370720_at | 0.003856 | −2.07 | Putative pheromone receptor VN6 |
| 1373533_at | 0.003878 | 1.25 | EST |
| 1391763_at | 0.003988 | −1.33 | Transcribed locus, weakly similar to XP_516348.1 PREDICTED: similar to glycerol-3-phosphate dehydrogenase 1-like [*Pan troglodytes*] |
| 1379258_at | 0.004084 | 1.30 | kelch-like 5 (*Drosophila*) (predicted) |
| 1372855_at | 0.004101 | 1.80 | Bromodomain containing 4 (predicted) |
| 1377342_s_at | 0.004128 | 1.46 | Rapostlin |
| 1372030_at | 0.004292 | −1.12 | zinc finger, FYVE domain containing 21 (predicted) |
| 1385789_at | 0.004371 | −2.09 | EST |
| 1378878_at | 0.004442 | −2.84 | similar to hypothetical protein FLJ25530 (predicted) |
| 1369748_at | 0.004471 | −1.63 | serine (or cysteine) proteinase inhibitor, clade I, member 2 |
| 1385103_at | 0.004588 | −1.29 | fused toes (predicted) |
| 1384518_at | 0.004619 | −1.32 | similar to PHD finger protein 14 isoform 1 |
| 1368323_at | 0.004645 | 1.38 | tissue factor pathway inhibitor |
| 1387230_at | 0.004717 | −1.64 | solute carrier family 12, member 3 |
| 1383457_at | 0.005114 | −1.86 | similar to hypothetical protein DKFZp761N1114 |
| 1392702_at | 0.005181 | 1.41 | EST |
| 1370866_at | 0.005191 | 1.41 | Ribosomal protein L41 |
| 1371958_at | 0.005199 | −1.36 | poly(A) binding protein, nuclear 1 |
| 1390189_at | 0.005346 | 1.15 | similar to Zinc finger protein 277 |
| 1374029_at | 0.005356 | 1.66 | EST |
| 1386917_at | 0.005360 | −1.50 | Pyruvate carboxylase |
| 1373245_at | 0.005366 | 1.22 | procollagen, type IV, alpha 1 (predicted) |
| 1385709_x_at | 0.005519 | −1.24 | Progressive ankylosis homolog (mouse) |
| 1394995_at | 0.005638 | −1.83 | Cobl-like 1 (predicted) |
| 1383147_at | 0.005643 | 1.31 | Transcribed locus |
| 1397631_at | 0.005720 | −1.34 | Ubiquitin specific protease 8 (predicted) |
| 1398290_at | 0.005734 | 1.27 | Potassium channel, subfamily K, member 13 |
| 1371572_at | 0.005800 | 1.26 | amyloid beta (A4) precursor protein |
| 1379651_at | 0.005994 | −1.30 | Forkhead box P1 (predicted) |
| 1387215_at | 0.006008 | −1.51 | alanine-glyoxylate aminotransferase |
| 1379418_at | 0.006108 | −1.53 | LOC501008 |
| 1375358_at | 0.006302 | 1.38 | Transcribed locus |
| 1394163_at | 0.006408 | 2.23 | SNF related kinase |
| 1372025_at | 0.006485 | −1.45 | Paternally expressed 3 (predicted) |
| 1386016_at | 0.006532 | −2.45 | EST |
| 1376964_at | 0.006542 | 1.56 | similar to Ofd1 protein |
| 1367750_at | 0.006592 | 1.22 | phosphoribosyl pyrophosphate synthetase-associated protein 1 |
| 1388755_at | 0.006685 | 1.22 | SEC23A (*S. cerevisiae*) (predicted) |
| 1390854_at | 0.006734 | 1.41 | transmembrane protein 24 (predicted) |
| 1376014_at | 0.006832 | −1.55 | Transcribed locus |
| 1379754_at | 0.006998 | −1.31 | Staufen, RNA binding protein, homolog 2 (*Drosophila*) |
| 1395327_at | 0.007147 | 1.29 | Lysosomal integral membrane protein-2 (LIMP-2) |
| 1373262_at | 0.007220 | 1.27 | Similar to 2310014H01Rik protein (predicted) |
| 1391108_at | 0.007232 | 2.13 | Transcribed locus |
| 1387938_at | 0.007304 | −2.17 | brain and acute leukemia, cytoplasmic |
| 1391819_at | 0.007324 | −1.68 | similar to hypothetical protein ET (predicted) |
| 1383216_at | 0.007326 | −1.44 | Cohen syndrome homolog 1 (predicted) |
| 1367744_at | 0.007456 | 1.58 | Melanoma antigen, family D, 2 |
| 1395869_at | 0.007484 | 1.20 | Similar to RIKEN cDNA A230063L24 gene |
| 1384147_at | 0.007519 | 1.43 | eukaryotic translation initiation factor 1A (predicted) |
| 1372476_at | 0.007698 | 1.37 | fatty acid desaturase 3 |
| 1387836_at | 0.007703 | 1.62 | Prenylated SNARE protein |

TABLE 2-continued

Genes that are differentially expressed in biopsies of failure-prone Ren-2 rats as compared to compensated Ren-2 rats.

| Probe Set ID[a] | p-value[b] | Fold Change[c] | Gene Name[d] |
|---|---|---|---|
| 1378958_at | 0.007759 | 1.22 | EST |
| 1385885_at | 0.007837 | −1.48 | Transcribed locus, moderately similar to XP_418312.1 PREDICTED: similar to Snf7 homologue associated with Alix 3 [*Gallus gallus*] |
| 1372621_at | 0.007920 | 1.44 | similar to 2610027C15Rik protein (predicted) |
| 1386228_at | 0.007970 | −2.39 | Similar to PHD finger protein 20-like 1 isoform 1 |
| 1388798_at | 0.007986 | −1.26 | ubiquitin-conjugating enzyme E2E 2 (UBC4/5 homolog, yeast) (predicted) |
| 1373584_at | 0.008209 | −1.29 | similar to hypothetical protein A430031N04 |
| 1383237_at | 0.008308 | 1.25 | Myoneurin (predicted) |
| 1394721_at | 0.008493 | −1.38 | similar to TTF-I interacting protein 5 |
| 1378315_at | 0.008560 | 1.82 | Transcribed locus |
| 1381519_at | 0.008621 | −1.76 | AT rich interactive domain 1A (Swi1 like) (predicted) |
| 1376059_at | 0.008765 | −1.53 | similar to hypothetical protein MGC38689 |
| 1388377_at | 0.008789 | 1.10 | coatomer protein complex subunit alpha (predicted) |
| 1374247_at | 0.008841 | 1.31 | Stabilin 1 (predicted) |
| 1373077_at | 0.008994 | 1.39 | similar to hypothetical protein D11Ertd497e (predicted) |
| 1376484_at | 0.009158 | −1.56 | Transcribed locus |
| 1388910_at | 0.009255 | −1.13 | mitochondrial ribosomal protein S24 (predicted) |
| 1393574_at | 0.009262 | −1.55 | Similar to Ccl-6 |
| 1393164_at | 0.009350 | −1.45 | mitochondrial ribosomal protein S27 (predicted) |
| 1373697_at | 0.009502 | 1.66 | myosin binding protein C, fast-type (predicted) |
| 1390317_at | 0.009509 | 2.80 | Transcribed locus |
| 1397642_at | 0.009553 | 1.27 | RAD50 homolog (*S. cerevisiae*) |
| 1397352_at | 0.009668 | −2.04 | Transcribed locus |
| 1392557_at | 0.009692 | 1.26 | Transcribed locus |
| 1384672_at | 0.009749 | −2.83 | similar to RIKEN cDNA 4930434E21 |
| 1396724_at | 0.009932 | −1.29 | EST |
| 1393135_at | 0.009960 | −1.24 | Transcribed locus |
| 1388478_at | 0.009986 | 1.27 | Transcribed locus |
| 1393318_at | 0.010526 | −1.32 | EST |
| 1394773_at | 0.010614 | −1.31 | Transcribed locus, moderately similar to XP_580018.1 PREDICTED: hypothetical protein XP_580018 [*Rattus norvegicus*] |
| 1397268_at | 0.010662 | −1.67 | similar to solute carrier family 17 (sodium phosphate), member 4; Na/PO4 cotransporter |
| 1371289_at | 0.011056 | −1.77 | nitric oxide synthase 2, inducible |
| 1390885_at | 0.011168 | 1.34 | Transcribed locus |
| 1392299_at | 0.011420 | −1.56 | C-terminal PDZ domain ligand of neuronal nitric oxide synthase |
| 1394767_at | 0.012694 | −1.52 | EST |
| 1373120_at | 0.019354 | −1.40 | Spermatogenesis associated 2 |

[a] Probe Set ID, Affymetrix probe set number

[b] p-value, P < 0.05 is considered statistically significant

[c] Fold-change, fold-change in gene expression of failure-prone Ren-2 rats as compared to compensated Ren-2 rats. For example, negative sign means down-regulated in failure-prone Ren-2 rats.

[d] Gene Name, name of gene associated with the Probe Set ID

TABLE 3

Echocardiographic parameters in LIMP-2 KO and WT mice at baseline, and after 14 and 28 days of AngII treatment

|  |  | Baseline | Day 14 | Day 28 |
|---|---|---|---|---|
| IVSd[a] (cm) | KO(n = 11) | 0.10 ± 0.00 | 0.10 ± 0.01[$] | 0.10 ± 0.01[$$] |
|  | WT(n = 10) | 0.10 ± 0.01 | 0.13 ± 0.01 | 0.13 ± 0.00* |
| LVIDd[a] (cm) | KO(n = 11) | 0.34 ± 0.01 | 0.38 ± 0.01[$$] | 0.38 ± 0.01[$$,*] |
|  | WT(n = 10) | 0.34 ± 0.01 | 0.33 ± 0.02 | 0.33 ± 0.01 |
| LVPWd[a] (cm) | KO(n = 11) | 0.10 ± 0.01 | 0.09 ± 0.01[$$] | 0.09 ± 0.00[$$] |
|  | WT(n = 10) | 0.10 ± 0.00 | 0.12 ± 0.01 | 0.15 ± 0.01* |
| LVAd[b] (cm) | KO(n = 11) | 0.21 ± 0.01 | 0.27 ± 0.01[$,*] | 0.28 ± 0.02[$,*] |
|  | WT(n = 10) | 0.21 ± 0.01 | 0.23 ± 0.01 | 0.22 ± 0.00 |
| LVLd[b] (cm) | KO(n = 11) | 0.73 ± 0.01 | 0.85 ± 0.02[$,*] | 0.84 ± 0.03[$$,*] |
|  | WT(n = 10) | 0.73 ± 0.01 | 0.79 ± 0.02[,*] | 0.79 ± 0.02 |
| FS[a] (%) | KO(n = 11) | 28.7 ± 1.9 | 20.1 ± 3.1 | 22.2 ± 3.0 |
|  | WT(n = 10) | 27.4 ± 2.1 | 25.8 ± 1.9 | 25.5 ± 2.9 |

Averages ± SEM
*P < 0.005 vs baseline KO or WT
[$]P < 0.05 vs age-matched WT
[$$]P < 0.001 vs age-matched WT
[a]Measured from short axis: IVSd, Interventricular septum in diastole; LVIDd, Left ventricular inner diameter in diastole; LVPWd, Left ventricular posterial wall thickness in diastole; FS (%), Percentage fractional shortening
[b]Measured from long axis: LVAd, Left ventricular area in diatole; LVLd, Left ventricular length in diastole

LITERATURE

Gamp et al., Hum. Mol. Genet. 12: 631-646, 2003.
Van Haaften et al., BMC Bioinformatics 7: online, 2006-09-21.
Schroen et al., Circ. Res. 110: 3121-3128, 2004.
Heymans et al., Circulation 112: 1136-1144, 2005.
Junqueira et al., Histochem. J. 11: 447-455, 1979.
De Windt et al., J. Mol. Cell. Cardiol. 29: 2095-2106, 1997.
Crombie et al., J. Biol. Chem. 273: 4855-4863, 1998.
Eskelinen et al., Trends Cell. Biol. 13: 137-145, 2003.
Nishino et al., Nature 406: 906-910, 2000.
Stypmann et al., Proc. Natl. Acad. Sci. USA 99: 6234-6239, 2002.
Stilli et al., Exp. Physiol. 2006.
Perriard et al., Trends Cardiovasc. Med. 13: 30-38, 2003.
Gumbiner, J. Cell. Biol. 148: 399-404, 2000.
Ferreira-Cornwell et al., J. Cell. Sci., 115: 1623-1634, 2002.
Sohal et al., Circ. Res. 89: 20-25, 2001.
Larsson et al., Embo J. 20: 1663-1673
Vandendriessche et al., J. Thromb. Haemost. 5(1): 16-24, 2007.

---

The invention claimed is:

1. A method for identifying a subject at risk of developing heart failure, comprising:
   (a) determining a level of one or more biological markers in a biological sample of said subject;
   (b) comparing the level of said biological marker to a standard level of the same biological marker; and
   (c) determining whether the level of the biological marker is indicative of a risk for developing heart failure, wherein the biological marker is a gene coding for a protein selected from the group consisting of KLF15 (SEQ ID NO: 27) and LIMP-2 (SEQ ID NO:30).

2. The method claimed in claim 1, wherein the method is performed in vitro.

3. The method claimed in claim 1 or 2, wherein the biological sample is selected from the group consisting of blood, plasma, serum, and cardiac tissue.

4. The method claimed in claim 1, wherein a decreased level of KLF15 gene expression, as compared to a standard level, is indicative of a risk of developing heart failure.

5. The method claimed in claim 1, wherein an increased level of LIMP-2 gene expression, as compared to a standard level, is indicative of a risk of developing heart failure.

* * * * *